United States Patent
Rothberg et al.

(10) Patent No.: US 11,712,221 B2
(45) Date of Patent: Aug. 1, 2023

(54) UNIVERSAL ULTRASOUND DEVICE AND RELATED APPARATUS AND METHODS

(71) Applicant: BFLY OPERATIONS, INC., Burlington, MA (US)

(72) Inventors: Jonathan M. Rothberg, Guilford, CT (US); Susan A. Alie, Stoneham, MA (US); Nevada J. Sanchez, Guilford, CT (US); Tyler S. Ralston, Clinton, CT (US); Christopher Thomas McNulty, Guilford, CT (US); Jaime Scott Zahorian, Guilford, CT (US); Paul Francis Cristman, New Haven, CT (US); Matthew de Jonge, New York, NY (US); Keith G. Fife, Palo Alto, CA (US)

(73) Assignee: BFLY OPERATIONS, INC., Burlington, MA (US)

( * ) Notice: Subject to any disclaimer, the term of this patent is extended or adjusted under 35 U.S.C. 154(b) by 897 days.

(21) Appl. No.: 15/626,711

(22) Filed: Jun. 19, 2017

(65) Prior Publication Data
US 2017/0360399 A1     Dec. 21, 2017

Related U.S. Application Data

(63) Continuation-in-part of application No. 15/415,434, filed on Jan. 25, 2017, now Pat. No. 10,856,840.
(Continued)

(51) Int. Cl.
*A61B 8/00*     (2006.01)
*B06B 1/02*     (2006.01)
(Continued)

(52) U.S. Cl.
CPC .......... *A61B 8/4477* (2013.01); *A61B 8/0883* (2013.01); *A61B 8/0891* (2013.01);
(Continued)

(58) Field of Classification Search
None
See application file for complete search history.

(56) References Cited

U.S. PATENT DOCUMENTS

| 4,389,601 A | 6/1983 | Sullivan |
| 4,814,637 A | 3/1989 | Roessler et al. |

(Continued)

FOREIGN PATENT DOCUMENTS

| CN | 101919710 A | 12/2010 |
| CN | 102027386 A | 4/2011 |

(Continued)

OTHER PUBLICATIONS

Lacefield, Chapter 13 Ultrasound Imaging, "Diagnostic Radiology Physics, A Handbook for Teachers and Students International" edited by Dance et al., Atomic Energy Agency, Vienna, 2014 (Year: 2014).*

(Continued)

*Primary Examiner* — Colin T. Sakamoto
(74) *Attorney, Agent, or Firm* — Osha Bergman Watanabe & Burton LLP

(57) ABSTRACT

A system comprising a multi-modal ultrasound probe configured to operate in a plurality of operating modes associated with a respective plurality of configuration profiles; and a computing device coupled to the handheld multi-modal ultrasound probe and configured to, in response to receiving input indicating an operating mode selected by a user, cause the multi-modal ultrasound probe to operate in the selected operating mode.

17 Claims, 22 Drawing Sheets

Related U.S. Application Data

(60) Provisional application No. 62/352,337, filed on Jun. 20, 2016.

(51) Int. Cl.
*A61B 8/08* (2006.01)
*A61B 8/12* (2006.01)
*B06B 1/06* (2006.01)

(52) U.S. Cl.
CPC ............. *A61B 8/12* (2013.01); *A61B 8/4236* (2013.01); *A61B 8/4427* (2013.01); *A61B 8/4444* (2013.01); *A61B 8/4472* (2013.01); *A61B 8/4494* (2013.01); *A61B 8/465* (2013.01); *A61B 8/467* (2013.01); *A61B 8/483* (2013.01); *A61B 8/485* (2013.01); *A61B 8/488* (2013.01); *A61B 8/5207* (2013.01); *A61B 8/54* (2013.01); *A61B 8/56* (2013.01); *B06B 1/0292* (2013.01); *B06B 1/0622* (2013.01)

(56) References Cited

U.S. PATENT DOCUMENTS

| | | | |
|---|---|---|---|
| 5,301,674 A * | 4/1994 | Erikson | A61B 8/488 600/447 |
| 5,315,999 A | 5/1994 | Kinicki et al. | |
| 5,417,218 A * | 5/1995 | Spivey | A61B 8/463 600/448 |
| 5,435,312 A * | 7/1995 | Spivey | A61B 8/13 600/448 |
| 5,640,960 A | 6/1997 | Jones et al. | |
| 5,744,898 A | 4/1998 | Smith et al. | |
| 5,833,614 A | 11/1998 | Dodd et al. | |
| 5,913,823 A | 6/1999 | Hedberg et al. | |
| 6,135,963 A | 10/2000 | Haider | |
| 6,795,374 B2 | 9/2004 | Barnes et al. | |
| 6,856,175 B2 | 2/2005 | Wodnicki | |
| 7,022,074 B2 | 4/2006 | Kristoffersen et al. | |
| 7,118,531 B2 | 10/2006 | Krill | |
| 7,382,366 B1 | 6/2008 | Klock et al. | |
| 7,549,961 B1 | 6/2009 | Hwang | |
| 7,612,483 B2 | 11/2009 | Degertekin | |
| 7,615,834 B2 | 11/2009 | Khuri-Yakub et al. | |
| 7,824,335 B2 | 11/2010 | Wodnicki | |
| 7,846,102 B2 | 12/2010 | Kupnik et al. | |
| 7,892,176 B2 | 2/2011 | Wodnicki et al. | |
| 8,079,966 B2 | 12/2011 | El-Bialy et al. | |
| D657,361 S | 4/2012 | Goodwin et al. | |
| 8,147,409 B2 | 4/2012 | Shifrin | |
| 8,277,380 B2 | 10/2012 | Daft et al. | |
| 8,292,834 B2 | 10/2012 | El-Bialy et al. | |
| 8,309,428 B2 | 11/2012 | Lemmerhirt et al. | |
| 8,399,278 B2 | 3/2013 | Lemmerhirt et al. | |
| 8,852,103 B2 | 10/2014 | Rothberg et al. | |
| 8,891,334 B2 | 11/2014 | Degertekin et al. | |
| 9,067,779 B1 | 6/2015 | Rothberg et al. | |
| 9,229,097 B2 | 1/2016 | Rothberg et al. | |
| 9,242,275 B2 | 1/2016 | Rothberg et al. | |
| 9,275,630 B2 * | 3/2016 | Blalock | G01S 7/52085 |
| 9,505,030 B2 | 11/2016 | Rothberg et al. | |
| 9,521,991 B2 | 12/2016 | Rothberg et al. | |
| 9,533,873 B2 | 1/2017 | Rothberg et al. | |
| 9,592,030 B2 | 3/2017 | Rothberg et al. | |
| 9,592,032 B2 | 3/2017 | Rothberg et al. | |
| 10,856,840 B2 | 12/2020 | Rothberg et al. | |
| 11,311,274 B2 | 4/2022 | Rothberg et al. | |
| 2003/0020810 A1 | 1/2003 | Takizawa et al. | |
| 2003/0048698 A1 * | 3/2003 | Barnes | G01S 7/52038 367/181 |
| 2003/0097071 A1 | 5/2003 | Halmann et al. | |
| 2003/0139661 A1 | 7/2003 | Kimchy et al. | |
| 2003/0149363 A1 | 8/2003 | Dreschel et al. | |
| 2004/0039283 A1 | 2/2004 | Banjanin et al. | |
| 2004/0064043 A1 | 4/2004 | Reilly et al. | |
| 2004/0085858 A1 | 5/2004 | Khuri-Yakub et al. | |
| 2004/0254459 A1 | 12/2004 | Kristoffersen et al. | |
| 2005/0101867 A1 * | 5/2005 | Johnson | G01S 15/8915 600/459 |
| 2005/0113689 A1 * | 5/2005 | Gritzky | A61B 5/0037 600/440 |
| 2006/0036176 A1 | 2/2006 | Angelsen et al. | |
| 2006/0173342 A1 * | 8/2006 | Panda | G01S 15/8959 600/459 |
| 2007/0035204 A1 | 2/2007 | Angelsen et al. | |
| 2007/0232921 A1 | 10/2007 | Lee | |
| 2008/0015441 A1 | 1/2008 | Kanda et al. | |
| 2009/0048520 A1 * | 2/2009 | Marteau | A61B 8/4455 600/459 |
| 2009/0069686 A1 | 3/2009 | Daft et al. | |
| 2009/0182237 A1 | 7/2009 | Angelsen et al. | |
| 2009/0240148 A1 | 9/2009 | Jeong et al. | |
| 2009/0250729 A1 | 10/2009 | Lemmerhirt et al. | |
| 2010/0137716 A1 * | 6/2010 | Liu | A61B 8/54 600/447 |
| 2010/0256488 A1 * | 10/2010 | Kim | G01S 15/8956 600/439 |
| 2010/0268081 A1 | 10/2010 | Asafusa et al. | |
| 2010/0286527 A1 * | 11/2010 | Cannon | A61B 8/56 600/459 |
| 2011/0055447 A1 | 3/2011 | Costa | |
| 2011/0071397 A1 | 3/2011 | Wodnicki et al. | |
| 2011/0213248 A1 | 9/2011 | Murakami et al. | |
| 2011/0306886 A1 | 12/2011 | Daft et al. | |
| 2011/0319735 A1 * | 12/2011 | Hill | A61B 8/0858 600/365 |
| 2012/0095347 A1 | 4/2012 | Adam et al. | |
| 2012/0115757 A1 | 5/2012 | Adams | |
| 2012/0194107 A1 * | 8/2012 | Kandori | B06B 1/0246 318/116 |
| 2012/0206014 A1 | 8/2012 | Bibi et al. | |
| 2012/0209150 A1 | 8/2012 | Zeng et al. | |
| 2012/0215109 A1 | 8/2012 | Kubota et al. | |
| 2012/0226161 A1 * | 9/2012 | Pelissier | A61B 8/4477 600/443 |
| 2013/0261466 A1 | 10/2013 | Owen et al. | |
| 2014/0000371 A1 | 1/2014 | Engl et al. | |
| 2014/0005521 A1 | 1/2014 | Köhler et al. | |
| 2014/0117812 A1 | 5/2014 | Hajati | |
| 2014/0187934 A1 | 7/2014 | Urness | |
| 2014/0264660 A1 | 9/2014 | Rothberg et al. | |
| 2014/0276069 A1 | 9/2014 | Amble et al. | |
| 2014/0288428 A1 | 9/2014 | Rothberg et al. | |
| 2014/0343378 A1 | 11/2014 | Ameson et al. | |
| 2015/0025378 A1 | 1/2015 | Susumu | |
| 2015/0032002 A1 | 1/2015 | Rothberg et al. | |
| 2015/0084053 A1 | 3/2015 | Rothberg et al. | |
| 2015/0087991 A1 | 3/2015 | Chen et al. | |
| 2015/0257733 A1 | 9/2015 | Corbett, III et al. | |
| 2015/0257740 A1 | 9/2015 | Horinaka | |
| 2016/0004330 A1 | 1/2016 | Sundaran et al. | |
| 2016/0007965 A1 | 1/2016 | Murphy et al. | |
| 2016/0157828 A1 * | 6/2016 | Sumi | G01N 29/46 702/189 |
| 2016/0179355 A1 | 6/2016 | K S | |
| 2016/0199030 A1 | 7/2016 | Patil et al. | |
| 2016/0262726 A1 * | 9/2016 | Yoon | A61B 8/5207 |
| 2016/0331353 A1 | 11/2016 | Ralston et al. | |
| 2017/0043375 A1 | 2/2017 | Weekamp et al. | |
| 2017/0188942 A1 | 7/2017 | Ghaffari et al. | |
| 2017/0360397 A1 | 12/2017 | Rothberg et al. | |
| 2017/0360405 A1 | 12/2017 | Rothberg et al. | |
| 2017/0360413 A1 | 12/2017 | Rothberg et al. | |
| 2017/0360414 A1 | 12/2017 | Rothberg et al. | |
| 2017/0360415 A1 | 12/2017 | Rothberg et al. | |
| 2018/0070917 A1 | 3/2018 | Rothberg et al. | |
| 2019/0000418 A1 | 1/2019 | Rothberg et al. | |

(56) References Cited

U.S. PATENT DOCUMENTS

| | | | |
|---|---|---|---|
| 2019/0129026 A1* | 5/2019 | Sumi | G01S 15/8915 |
| 2020/0191928 A1* | 6/2020 | Hope Simpson ... | G01S 7/52034 |

FOREIGN PATENT DOCUMENTS

| | | | |
|---|---|---|---|
| CN | 102149428 A | 8/2011 | |
| CN | 102755175 A | 10/2012 | |
| CN | 103221093 A | 7/2013 | |
| CN | 103284754 A | 9/2013 | |
| CN | 103347564 A | 10/2013 | |
| CN | 104168837 A | 11/2014 | |
| CN | 104271265 A | 1/2015 | |
| CN | 104756521 A | 7/2015 | |
| CN | 104905822 A | 9/2015 | |
| CN | 104970825 A | 10/2015 | |
| CN | 105431749 A | 3/2016 | |
| EP | 2 805 672 A1 | 11/2014 | |
| JP | 2007-260188 A | 10/2007 | |
| JP | WO 2010/055820 A1 | 4/2012 | |
| JP | 2015-100404 A | 6/2015 | |
| JP | 2016-508429 A | 3/2016 | |
| KR | 10-2013-0004854 A | 1/2013 | |
| WO | WO 2009/135255 A1 | 11/2009 | |
| WO | 2009/149499 | 12/2009 | |
| WO | WO 2013/170053 A1 | 11/2013 | |
| WO | WO 2015/028314 A1 | 3/2015 | |
| WO | WO 2015/028945 A2 | 3/2015 | |
| WO | WO 2016/075586 A1 | 5/2016 | |

OTHER PUBLICATIONS

Moiyadi, "Intraoperative Ultrasound Technology in Neuro-Oncology Practice—Current Role and Future Applications" World Neurosurgery 93: 81-93, 2016 (Year: 2016).*
"Probecraft" MED-PoCUS, Middlemore Hospital Emergency Medicine Education (MMHEME), http://www.mmheme.org/knobology retrieved on Mar. 10, 2023 (Year: 2023).*
Dinh, "Ultrasound Machine Basics—Knobology, Probes, and Modes" POCUS101, https://www.pocus101.com/ultrasound-machine-basics-knobology-probes-and-modes/ retrieved on Mar. 10, 2023 (Year: 2023).*
Whittingham, "Medical diagnostic applications and sources" Progress in Biophysics and Molecular Biology. vol. 93, Issues 1-3, Jan.-Apr. 2007, pp. 84-110 available online 2006 (Year: 2006).*
International Search Report and Written Opinion dated Aug. 29, 2017 in connection with International Application No. PCT/US2017/038100.
International Search Report and Written Opinion dated Nov. 2, 2017 in connection with International Application No. PCT/US2017/049027.
STMicroeletronics, STHV748 Quad +/−90 V, +/- 2 A, 3/5 levels, high speed ultrasound pulser. Datasheet. Jan. 2016. 29 pages.
Supertex Inc., MD1712 High Speed, Integrated Ultrasound Driver IC. Datasheet. 2012. 12 pages.
Texas Instruments, TX734 Quad Channel, 3-Level RTZ, +/−75-V, 2-A Integrated Ultrasound Pulser. Datasheet. Nov. 2008. 6 pages.
Agarwal et al., Single-Chip Solution for Ultrasound Imaging Systems: Initial Results. 2007 IEEE Ultrasonics Symposium. Oct. 1, 2007;1563-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Kobe, Japan. Nov. 12-14, 2012;173-6.
Chen et al., Ultrasonic Imaging Transceiver Design for CMUT: A Three-Level 30-Vpp Pulse-Shaping Pulser With Improved Efficiency and a Noise-Optimized Receiver. IEEE J Solid-State Circ. Nov. 2013;48(11):2734-45.
Cheng et al., CMUT-in-CMOS ultrasonic transducer arrays with on-chip electronics. IEEE Transducers 2009. Denver, CO. Jun. 21-25, 2009;1222-5.
Daft et al., A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;493-6.
Gurun et al., Front-end CMOS Electronics for Monolithic Integration with CMUT Arrays: Circuit Design and Initial Experimental Results. 2008 IEEE International Ultrasonics Symposium Proceedings. 2008;390-3.
Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. Doi: 10.1109/IEMBS.2010.5627580. Epub Dec. 6, 2010. 13 pages.
Kim et al., Design and Test of a Fully Controllable 64×128 2-D CMUT Array Integrated with Reconfigurable Frontend ASICs for Volumetric Ultrasound Imaging. 2012 IEEE International Ultrasonics Symposium Proceedings. Oct. 7-10, 2012;77-80.
Kupnik et al., Wafer-Bonded CMUT Meets CMOS. 2010 CMOS Emerging Technology Workshop. Whistler, Canada. May 21, 2010;1-22.
Noble et al., A Cost-effective and Manufacturable Route to the Fabrication of High-Density 2D Micromachined Ultrasonic Transducer Arrays and (CMOS) Signal Conditioning Electronics on the same Silicon Substrate. 2001 IEEE Ultrasonics Symposium. 2001;941-5.
Zahorian et al., Single chip CMUT arrays with integrated CMOS electronics: Fabrication Process Development and Experimental Results. 2008 IEEE International Ultrasonics Symposium Proceedings. 2008;386-9.
International Search Report and Written Opinion dated Nov. 13, 2014 in connection with International Application No. PCT/US2014/032803.
Fairbanks et al., Ocular Ultrasound: A Quick Reference Guide ofr the On-Call Physician. EyeRounds.org. University of Iowa Carver College of Medicine posted Feb. 4, 2016. http ://www.EyeRounds.org/tutorials/ultrasound.
Via et al., Lung Ultrasound in the ICU: From Diagnostic Instrument to Respiratory Monitoring Tool. Minerva Anestesiologica. Nov. 2012; 78 (11): 1282-96.
International Preliminary Report on Patentability dated Jan. 3, 2019 in connection with International Application No. PCT/US2017/038100.
Bavaro et al., Element Shape Design of 2-D CMUT Arrays for Reducing Rating Lobes. IEEE Transactions on Ultrasonics, Ferroelectrics and Frequency Control. Feb. 2008;55(2):308-18.
Extended European Search Report dated Dec. 19, 2019 in connection with European Application No. 17815994.3.
Shung, Diagnostic Ultrasound: Imaging and Blood Flow Measurements. 2006; 207 pages.
Hayes et al., Three-MHz Ultrasound Heats Deeper Into the Tissue Than Originally Theorized. Journal of Athletic Training. Jul.-Sep. 2004; 39(3):230-234.
Hendee et al., Medical Imaging Physics. Fourth Edition. 2002 Wiley-Liss, Inc. Chapter 19. 2002.
Shung, Diagnostic Ultrasound: Imaging and Blood Flow Measurements. Second Edition, CRC Press. Taylor & Francis Group, LLC. Boca Raton, FL. 2015.
Tole et al., Basic Physics of Ultrasonographic Imaging. World Health Organization. Edited by H. Ostensen. 2005.
Belohlavek et al., Rapid three-dimensional echocardiography: clinically feasible alternative for precise and accurate measurement of left ventricular volumes. Circulation. Jun. 19, 2001;103(24):2882-4.
European Communication dated Sep. 17, 2020 in connection with European Application No. 17815994.3.
Stoylen, Basic ultrasound for clinicians. Strain rate imaging. NTNU Norwegian University of Science and Technology. Apr. 2016.

* cited by examiner

UNIVERSAL ULTRASOUND DEVICE AND RELATED APPARATUS AND METHODS

CROSS-REFERENCE TO RELATED APPLICATIONS

This Application is a continuation-in-part claiming the benefit under 35 U.S.C. § 120 of U.S. application Ser. No. 15/415,434, entitled "UNIVERSAL ULTRASOUND DEVICE AND RELATED APPARATUS AND METHODS," filed on Jan. 25, 2017, which claims the benefit under 35 U.S.C. § 119(e) of U.S. Provisional Application Ser. No. 62/352,337, entitled "UNIVERSAL ULTRASOUND DEVICE AND RELATED APPARATUS AND METHODS," filed on Jun. 20, 2016, each of which is hereby incorporated herein by reference in its entirety.

This application is also an application claiming the benefit under 35 U.S.C. 119(e) of U.S. Provisional Application Ser. No. 62/352,337, entitled "UNIVERSAL ULTRASOUND DEVICE AND RELATED APPARATUS AND METHODS," filed on Jun. 20, 2016, which is hereby incorporated herein by reference in its entirety.

FIELD

The present application relates to an ultrasound device that can operate across multiple different frequency ranges to obtain high-resolution images of a subject at different depths.

BACKGROUND

Ultrasound imaging systems typically include an ultrasound probe connected to a host by an analog cable. The ultrasound probe is controlled by the host to emit and receive ultrasound signals. The received ultrasound signals are processed to generate an ultrasound image.

SUMMARY

Some embodiments are directed to an ultrasound device including an ultrasound probe, including a semiconductor die, and a plurality of ultrasonic transducers integrated on the semiconductor die, the plurality of ultrasonic transducers configured to operate in a first mode associated with a first frequency range and a second mode associated with a second frequency range, wherein the first frequency range is at least partially non-overlapping with the second frequency range; and control circuitry configured to: control the plurality of ultrasonic transducers to generate and/or detect ultrasound signals having frequencies in the first frequency range, in response to receiving an indication to operate the ultrasound probe in the first mode; and control the plurality of ultrasonic transducers to generate and/or detect ultrasound signals having frequencies in the second frequency range, in response to receiving an indication to operate the ultrasound probe in the second mode.

Some embodiments are directed to a system, comprising: a multi-modal ultrasound probe (e.g., a hand-held multi-modal ultrasound probe) configured to operate in a plurality of operating modes associated with a respective plurality of configuration profiles; and a computing device (e.g., a mobile computing device) coupled to the multi-modal ultrasound probe and configured to, in response to receiving input indicating an operating mode selected by a user, cause the multi-modal ultrasound probe to operate in the selected operating mode.

Some embodiments are directed to a method for controlling operation of a multi-modal ultrasound probe configured to operate in a plurality of operating modes associated with a respective plurality of configuration profiles, the method comprising: receiving, at a computing device, input indicating an operating mode selected by a user; and causing the multi-modal ultrasound probe to operate in the selected operating mode using parameter values specified by a configuration profile associated with the selected operating mode.

Some embodiments are directed to a system, comprising: an ultrasound device, comprising: a plurality of ultrasonic transducers, and control circuitry; and a computing device having at least one computer hardware processor and at least one memory, the computing device communicatively coupled to a display and to the ultrasound device, the at least one computer hardware processor configured to: present, via the display, a graphical user interface (GUI) showing a plurality of GUI elements representing a respective plurality of operating modes for the ultrasound device, the plurality of operating modes comprising first and second operating modes; responsive to receiving, via the GUI, input indicating selection of either the first operating mode or the second operating mode, provide an indication of the selected operating mode to the ultrasound device, wherein the control circuitry is configured to: responsive to receiving an indication of the first operating mode, obtain a first configuration profile specifying a first set of parameter values associated with the first operating mode; and control, using the first configuration profile, the ultrasound device to operate in the first operating mode, and responsive to receiving an indication of the second operating mode, obtain a second configuration profile specifying a second set of parameter values associated with the second operating mode, the second set of parameter values being different from the first set of parameter values; and control, using the second configuration profile, the ultrasound device to operate in the second operating mode.

Some embodiments are directed to a method, comprising: receiving, via a graphical user interface, a selection of an operating mode for an ultrasound device configured to operate in a plurality of modes including a first operating mode and a second operating mode; responsive to receiving a selection of a first operating mode, obtaining a first configuration profile specifying a first set of parameter values associated with the first operating mode; and controlling, using the first configuration profile, the ultrasound device to operate in the first operating mode, and responsive to receiving a selection of the second operating mode, obtaining a second configuration profile specifying a second set of parameter values associated with the second operating mode, the second set of parameter values being different from the first set of parameter values; and controlling, using the second configuration profile, the ultrasound device to operate in the second operating mode.

Some embodiments are directed to a handheld multi-modal ultrasound probe configured to operate in a plurality of operating modes associated with a respective plurality of configuration profiles, the handheld ultrasound probe comprising: a plurality of ultrasonic transducers; and control circuitry configured to: receive an indication of a selected operating mode; access a configuration profile associated with the selected operating mode; and control, using parameter values specified in the accessed configuration profile, the handheld multi-modal ultrasound probe to operate in the selected operating mode.

Some embodiments are directed to an ultrasound device capable of operating in a plurality of operating modes including a first operating mode and a second operating mode, the ultrasound device comprising: a plurality of ultrasonic transducers, and control circuitry configured to: receive an indication of a selected operating mode; responsive to determining that the selecting operating mode is the first operating mode, obtain a first configuration profile specifying a first set of parameter values associated with the first operating mode; and control, using the first configuration profile, the ultrasound device to operate in the first operating mode, and responsive to receiving an indication of the second operating mode, responsive to determining that the selecting operating mode is the second operating mode, obtain a second configuration profile specifying a second set of parameter values associated with the second operating mode, the second set of parameter values being different from the first set of parameter values; and control, using the second configuration profile, the ultrasound device to operate in the second operating mode.

Some embodiments are directed to a mobile computing device communicatively coupled to an ultrasound device, the mobile computing device comprising: at least one computer hardware processor; a display; and at least one non-transitory computer-readable storage medium storing an application program that, when executed by the at least one computer hardware processor causes the at least one computer hardware processor to: generate a graphical user interface (GUI) having a plurality of GUI elements representing a respective plurality of operating modes for the multi-modal ultrasound device; present the GUI via the display; receive, via the GUI, user input indicating selection of one of the plurality of operating modes; and provide an indication of the selected operating mode to the ultrasound device.

BRIEF DESCRIPTION OF THE DRAWINGS

Various aspects and embodiments of the disclosed technology will be described with reference to the following figures. It should be appreciated that the figures are not necessarily drawn to scale. Items appearing in multiple figures are indicated by the same reference number in all the figures in which they appear.

DETAILED DESCRIPTION

Figure 1A:
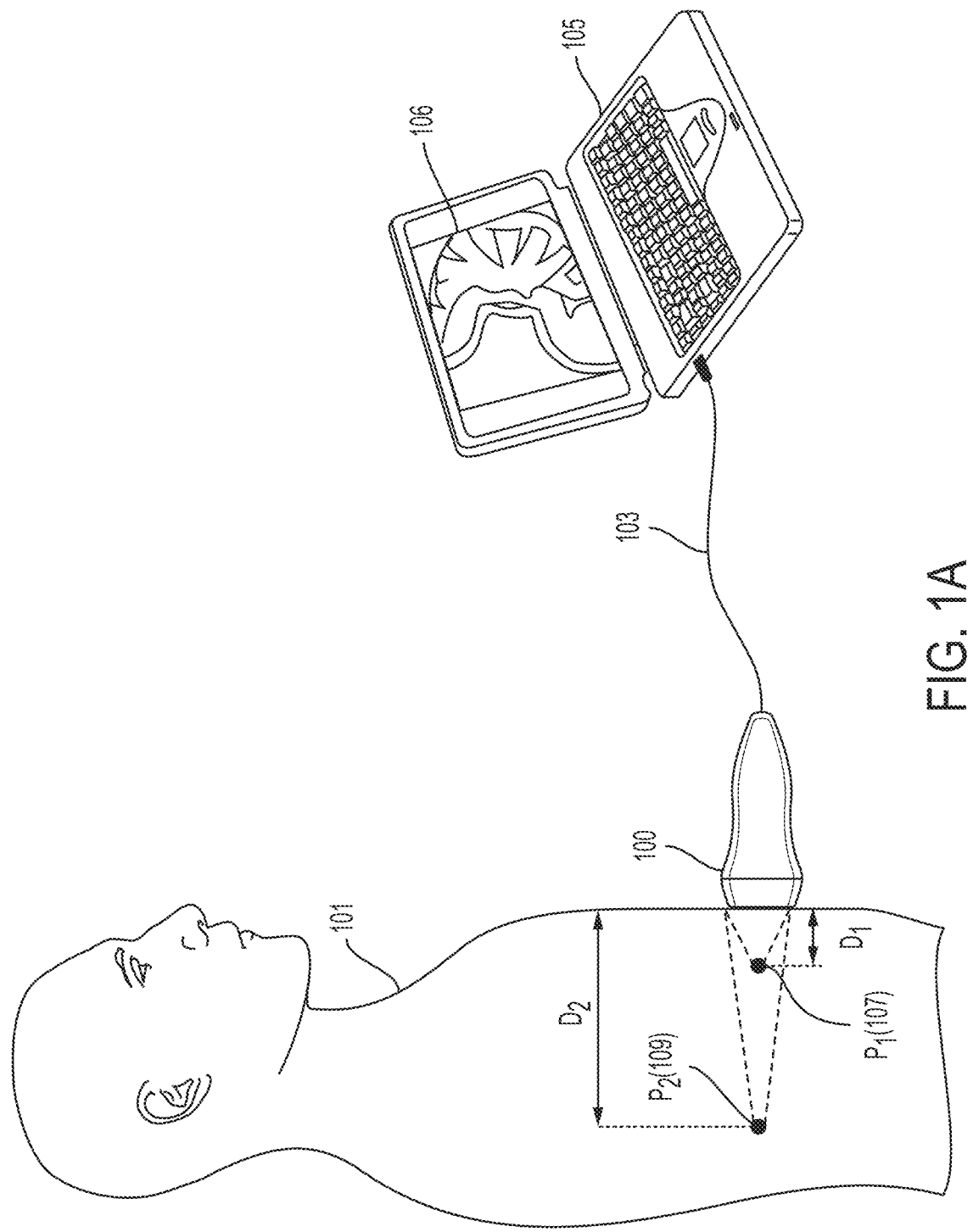
FIG. 1A is a diagram illustrating how a universal ultrasound device may be used to image a subject, in accordance with some embodiments of the technology described herein.

The present disclosure describes aspects of a "universal" ultrasound device configured to image a subject at multiple different frequency ranges. The universal ultrasound device includes multiple ultrasonic transducers at least some of which can operate at different frequency ranges, thereby enabling the use of a single ultrasound device to generate medically-relevant images of a subject at different depths. As a result, a single device (the universal ultrasound device described herein) may be used by medical professionals or other users to perform different imaging tasks that presently require use of multiple conventional ultrasound probes.

Some embodiments are directed to an ultrasound device comprising an ultrasound probe. The ultrasound probe comprises a semiconductor die; a plurality of ultrasonic transducers integrated on the semiconductor die, the plurality of ultrasonic transducers configured to operate in a first mode associated with a first frequency range and a second mode associated with a second frequency range, wherein the first frequency range is at least partially non-overlapping with the second frequency range; and control circuitry. The control circuitry is configured to control the plurality of ultrasonic transducers to generate and/or detect ultrasound signals having frequencies in the first frequency range, in response to receiving an indication to operate the ultrasound probe in the first mode, and control the plurality of ultrasonic transducers to generate and/or detect ultrasound signals having frequencies in the second frequency range, in response to receiving an indication to operate the ultrasound probe in the second mode.

The inventors have recognized that conventional ultrasound probes are limited because each of them operates at just a single one of several medically-relevant frequency ranges. For example, some conventional ultrasound probes operate only at frequencies in the range of 1-3 MHz (e.g., for applications such as obstetric, abdomen and gynecological imaging), whereas other conventional probes operate only at frequencies in the range of 3-7 MHz (e.g., for applications such as breast, vascular, thyroid, and pelvic imaging). Still other conventional ultrasound probes operate only at frequencies in the range of 7-15 MHz (e.g., for applications such as musculosketal and superficial vein and mass imaging). Since higher frequency ultrasound signals attenuate faster in tissue than lower frequency ultrasound signals, conventional probes operating only at higher frequencies are used for generating images of a patient at shallow depths (e.g., 5 cm or less) for applications such as central line placement or the aforementioned imaging of superficial masses located just beneath the skin. On the other hand, conventional probes operating only at lower frequencies are used to generate images of a patient at greater depths (e.g., 10-25 cm) for applications such as cardiac and kidney imaging. As a result, a medical professional needs to use multiple different probes, which is inconvenient and expensive, as it requires procuring multiple different probes configured to operate at different frequency ranges.

By contrast, the universal ultrasound device, developed by the inventors and described herein, is configured to operate at multiple different medically-relevant frequency ranges and image patients at a sufficiently high resolution for forming medically-relevant images at a wide range of depths. As such, multiple conventional ultrasound probes can all be replaced by the single universal ultrasound device described herein, and medical professionals or other users may use a single universal ultrasound probe to perform multiple imaging tasks instead of using a multitude of conventional ultrasound probes each having limited applicability.

Figure 5A:
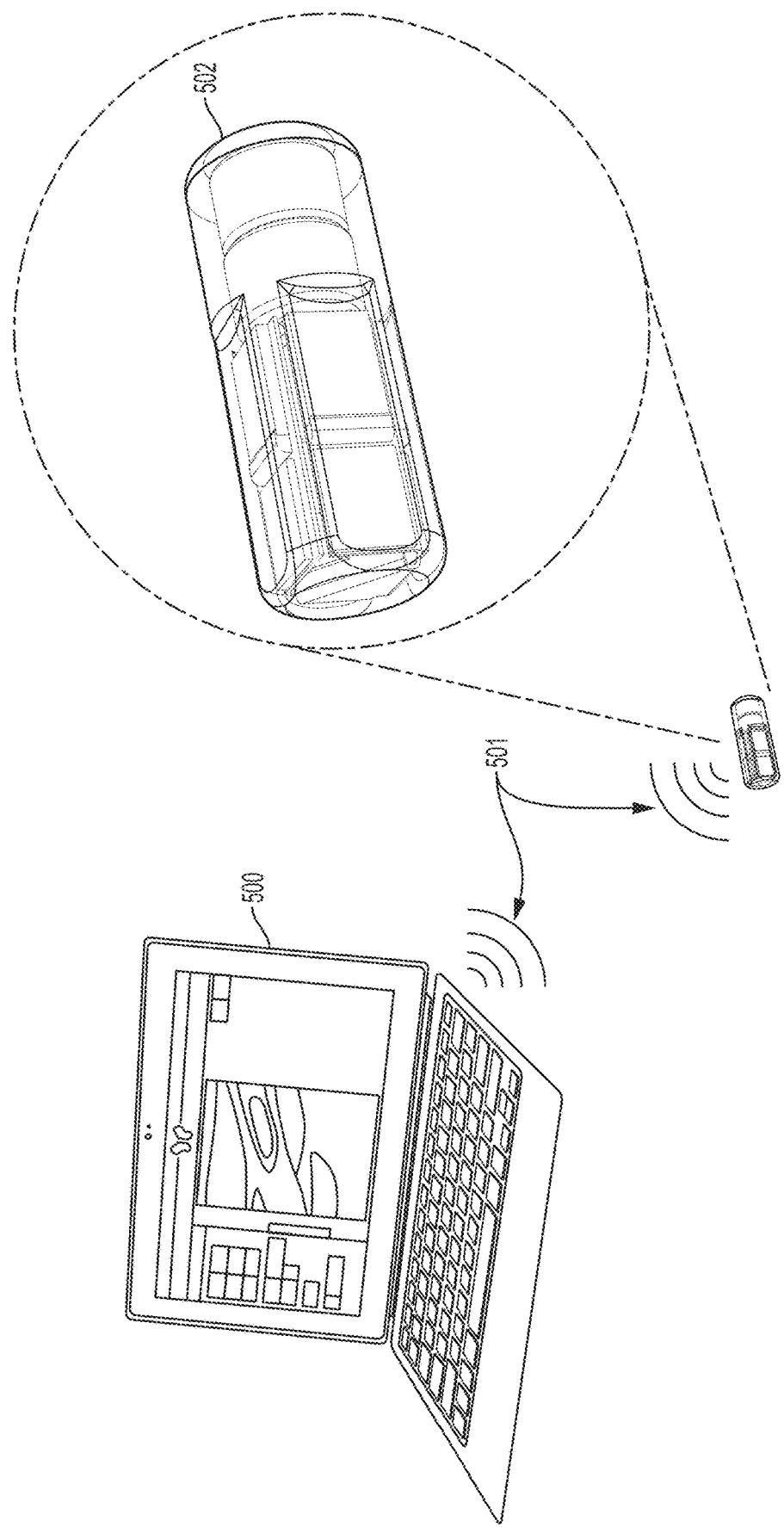
FIGS. 5A-5H illustrate a pill comprising an ultrasound probe, in accordance with some embodiments of the technology described herein.

Accordingly, some embodiments provide for wideband ultrasound probe having multiple ultrasonic transducers configured to operate in each of a multiple of modes including a first mode associated with a first frequency range and a second mode associated with a second frequency range, which is at least partially non-overlapping with the first frequency range. The multi-frequency ultrasound probe further comprises control circuitry that is configured to control the plurality of ultrasonic transducers to generate and/or detect ultrasound signals having frequencies in the first frequency range, in response to receiving an indication to operate the ultrasound probe in the first mode, and control the plurality of ultrasonic transducers to generate and/or detect ultrasound signals having frequencies in the second frequency range, in response to receiving an indication to operate the ultrasound probe in the second mode. The ultrasonic transducers may be integrated on a single substrate such as a single complementary metal oxide semiconductor (CMOS) chip, or may be on multiple chips within an ultrasound probe (e.g., as shown in FIGS. 5G and 5H).

In some embodiments, the first frequency range may include frequencies in the range of 1-5 MHz. For example, the first frequency range may be contained entirely within a range of 1-5 MHz (e.g., within a range of 2-5 MHz, 1-4 MHz, 1-3 MHz, 2-5 MHz, and/or 3-5 MHz). Accordingly, when the ultrasonic transducers of the universal ultrasound probe are operated to generate and/or detect ultrasound signals having frequencies in the first frequency range, ultrasound signals detected by the ultrasonic transducers may be used to form an image of a subject up to target depths within the subject, the target depths being in a range of 10-25 cm (e.g., within a range of 10-20 cm, 15-25 cm, 10-15 cm, 15-20 cm, and/or 20-25 cm).

In some embodiments, the second frequency range may be contained entirely within a range of 5-12 MHz (e.g., within a range of 5-10 MHz, 7-12 MHz, 5-7 MHz, 5-9 MHz, 6-8 MHz, 7-10 MHz, and/or 6-9 MHz). Accordingly, when the ultrasonic transducers of the universal ultrasound probe are operated to generate and/or detect ultrasound signals having frequencies in the second frequency range, ultrasound signals detected by the ultrasonic transducers may be used to form an image of a subject up to target depths within the subject, the target depths being in a range of 1-10 cm (e.g., within a range of 1-5 cm, 5-10 cm, 3-8 cm, 3-6 cm, and/or 3-5 cm).

In some embodiments, the multiple modes of the universal ultrasound probe in combination span at least 10 MHz or between 8-15 MHz. For this reason, a universal ultrasound probe may be sometimes called a "wideband" probe, a multi-modal probe (having multiple frequency range modes), and/or a multi-frequency probe.

It should be appreciated that a universal ultrasound probe is not limited to operating in only two modes and may operate in any suitable number of modes (e.g., 3, 4, 5, etc.) with each of the modes being associated with a respective frequency range. For example, in some embodiments, the universal ultrasound probe may operate in first, second, and third modes associated with a first, second, and third frequency ranges, respectively. The first, second, and third frequency ranges may be any suitable set of three ranges that, pairwise, do not entirely overlap one another. For example, the first frequency range may be contained entirely within a range of 1-3 MHz, the second frequency range may be contained entirely within a range of 3-7 MHz, and the third frequency range may be contained entirely within a range of 7-12 MHz. As another example, the first frequency range may be contained entirely within a range of 1-5 MHz, the second frequency range may be contained entirely within a range of 3-7 MHz, and the third frequency range may be contained entirely within a range of 5-10 MHz. In addition, each mode may also have different elevational focal regions, a feature not possible with a single 1D array using an elevational focusing acoustic lens. Each mode may also have different pitch of elements based on the frequency of operation. The different pitch may be implemented, for example, by subset selection and combinations of transducer cells.

As may be appreciated from the foregoing examples of frequency ranges, an operating mode of the ultrasound probe may be associated with a frequency bandwidth of at least 1 MHz, in some embodiments. In other embodiments, an operating mode of the ultrasound probe may be associated with a bandwidth of at least 2 MHz, at least 3 MHz, or at least 4 MHz or higher, as aspects of the technology described herein are not limited in this respect. At least some of the transducers of the ultrasound probe, and in some embodiments each transducer, may not only operate at different frequency ranges, but also may operate in a particular frequency range (e.g., at a center frequency of the frequency range) with a wide bandwidth. In other embodiments (e.g., for Doppler imaging), an operating mode of the ultrasound prove may span bandwidths narrower than 1 MHz.

As described, ultrasound devices in accordance with one or more of the various aspects described herein may be used for Doppler imaging—that is, in a Doppler mode. The ultrasound device may measure velocities in a range from about 1 cm/s to 1 m/s, or any other suitable range.

When operating in a particular mode, ultrasonic transducers of a probe may generate ultrasound signals having the largest amount of power at a peak power frequency for the mode (e.g., which may be a center frequency of the frequency range associated with the mode). For example, when operating in a mode associated with a frequency range of 1-5 MHz, the ultrasonic transducers may be configured to generate ultrasound signals having the largest amount of power at 3 MHz. Therefore, the peak power frequency for this mode is 3 MHz in this example. As another example, when operating in a mode associated with a frequency range of 5-9 MHz, the ultrasonic transducers may be configured to generate ultrasound signals having the largest amount of power at 7 MHz, which is the peak power frequency in this example.

As may be appreciated from the foregoing examples of frequency ranges, a universal ultrasound probe may be configured to operate in multiple modes including a first mode associated with a first frequency range having a first peak power frequency and a second mode associated with as second frequency range having a second peak power frequency. In some instances, the difference between the first and second peak power frequencies is at least a threshold amount (e.g., at least 1 MHz, at least 2 MHz, at least 3 MHz, at least 4 MHz, at least 5 MHz, etc.).

It should be appreciated that, when operating in a frequency range, an ultrasonic transducer may, in some embodiments, generate signals at frequencies outside of the operating frequency range. However, such signals would be generated at less than a fraction (e.g., ½, ⅓, ⅕, etc.) of the largest power at which a signal at a center frequency of the range is generated, for example 3 dB or 6 dB down from the maximum power.

The universal ultrasound probe described herein may be used for a broad range of medical imaging tasks including, but not limited to, imaging a patient's liver, kidney, heart, bladder, thyroid, carotid artery, lower venous extremity, and performing central line placement. Multiple conventional ultrasound probes would have to be used to perform all these imaging tasks. By contrast, a single universal ultrasound probe may be used to perform all these tasks by operating, for each task, at a frequency range appropriate for the task, as shown in Table I together with corresponding depths at which the subject is being imaged.

TABLE 1

Illustrative depths and frequencies at which a universal ultrasound probe implemented in accordance with embodiments described herein can image a subject.

| Organ | Frequencies | Depth (up to) |
| --- | --- | --- |
| Liver/Right Kidney | 2-5 MHz | 15-20 cm |
| Cardiac (adult) | 1-5 MHz | 20 cm |
| Bladder | 2-5 MHz; 3-6 MHz | 10-15 cm; 5-10 cm |
| Lower extremity venous | 4-7 MHz | 4-6 cm |
| Thyroid | 7-12 MHz | 4 cm |
| Carotid | 5-10 MHz | 4 cm |
| Central Line Placement | 5-10 MHz | 4 cm |

It should be appreciated that Table 1 provides a non-limiting example of some organs for imaging at respective depths and frequencies. However, other organs or targets may corresponded to the listed frequency ranges. For instance, the 2-5 MHz range may generally be used for abdominal, pelvic and thoracic sonography. Further examples of anatomical targets within this frequency range include the gallbladder, bile ducts, pancreas, gastrointestinal tract, urinary tract, spleen, adrenal glands, abdominal aorta, groin, anterior abdominal wall, peritoneum, breast, and pelvic muscles. Additionally, the 2-5 MHz range or 3-6 MHz range may generally be used for obstetrics, such as fetal imaging or imaging of the placenta. Additionally, in the 7-12 MHz range, examples of anatomical targets other than those listed in Table 1 include the parathyroid, breast, scrotum, rotator cuff, tendons, and extracranial cerebral vessels. It should be appreciated that this list of examples is non-limiting, and any suitable organ and frequency range combination may be used herein.

FIG. 1A further illustrates how a universal ultrasound probe may operate in different modes, associated with different frequency ranges, to image a subject at different depths. As shown in FIG. 1A, ultrasound probe 100 is being used to image subject 101. When operating in a first mode, associated with a first frequency range (e.g., 1-3 MHz), the ultrasonic transducers in probe 100 may be configured to image the subject at or about a point 109, also labeled P2, located at a depth D2 (e.g., 15-20 cm) from the subject's skin. When operating in a second mode, associated with a second frequency range (e.g., 6-8 MHz), the ultrasonic transducers in probe 100 may be configured to image the subject at or about a point 107, also labeled P1, located at a depth D1 (e.g., 1-5 cm) from the subject's skin. In some embodiments, the distance D2 is greater than the distance D1 by at least a threshold distance (e.g., at least 5 cm, at least 7 cm, between 3 and 7 cm, or any range or number within such ranges).

Ultrasound probe 100 transmit may be configured to transmit data collected by the probe 100 to one or more external devices for further processing. For example, as shown in FIG. 1A, ultrasound probe 100 may be configured to transmit data collected by probe 100 via wired connection 103 to computing device 105 (a laptop in this non-limiting example), which may process the data to generate and display an image 111 of the subject 101 on a display.

Various factors contribute to the ability of the universal ultrasound probe to operate in multiple modes associated with different and medically-relevant frequency ranges. One such factor is that the ultrasonic transducers may be formed by capacitive micromachined ultrasonic transducers (CMUTs) and, in some embodiments, at least some (and in some embodiments each) of multiple ultrasonic transducers in the universal ultrasound probe is configured to operate in collapsed mode and in non-collapsed mode. As described herein, a "collapsed mode" refers to a mode of operation in which at least one portion of a CMUT ultrasonic transducer membrane is mechanically fixed and at least one portion of the membrane is free to vibrate based on a changing voltage differential between the electrode and the membrane. When operating in collapsed mode, a CMUT ultrasonic transducer is capable of generating more power at higher frequencies. Switching operation of multiple ultrasonic transducers from non-collapsed mode into collapsed mode (and vice versa) allows the ultrasound probe to change the frequency range at which the highest power ultrasound signals are being emitted.

Accordingly, in some embodiments, an ultrasound probe operates in a first mode associated with a first frequency range (e.g., 1-5 MHz, with a peak power frequency of 3 MHz) by operating its transducers in non-collapsed mode, and operates in a second mode associated with a second frequency range (e.g., 5-9 MHz, with a peak power frequency of 7 MHz) by operating its transducers in collapsed mode. In some embodiments, the ultrasound probe includes control circuitry (e.g., circuitry 108 shown in FIG. 1B) configured to control the probe to operate in either first mode or the second mode and, to this end, may apply appropriate voltages to the ultrasonic transducers to cause them to operate in collapsed mode or in non-collapsed mode. For example, in some embodiments, the control circuitry is configured to cause ultrasonic transducers in the probe to operate in collapsed mode by applying a voltage to the transducers that exceeds a threshold voltage, which is sometimes called a "collapse" voltage. The collapse voltage may be in the range of 30-110 Volts and, in some embodiments, may be approximately 50 Volts. It should be noted that, while in some embodiments operating a probe's transducers in collapsed and non-collapsed modes may be a factor that helps the probe to operate in multiple frequency range modes, there may also be other factors that allow the probe to do so (e.g., an analog receiver capable of broadband signal amplification of about 1-15 MHz).

Another factor that contributes to the ability of the universal ultrasound probe to operate in multiple modes associated with different and medically-relevant frequency ranges is that the ultrasonic transducers may be arranged in an array having a pitch adequate for both high-frequency and low frequency scanning. For example, in some embodiments, at least some of the ultrasonic transducers may be spaced apart from its nearest neighbor at a distance less than half of a wavelength corresponding to the highest frequency at which the probe is designed to operate to reduce (e.g., eliminate) aliasing effects. At least some, and in some cases each, mode(s) may also have different pitch of elements based on the frequency of operation. The different pitch is enabled by subset selection and combining of CMOS ultrasonic transducer (CUT) cells. Adequate pitches for a frequency are generally spaced between about $\lambda$ and $\lambda/4$, where $\lambda$ is the wavelength at the specified frequency. Exemplary pitches may include, but are not limited to, 500 microns ($\mu$m) (very low frequencies), 200 $\mu$m (moderate frequencies), and 125 $\mu$m (high frequencies). Also, in certain embodiments, pitches may be made wider due to element directivity helping to suppress aliasing artifacts (e.g., on the order of $\lambda$). The previously listed pitches are non-limiting, as other pitches are possible. In some embodiments, the pitch may be within a range of about 150 to 250 microns (including any value within that range) per transducer for sector scanning. For example, a 208 micron pitch may correspond 3.7 MHz operation.

Another factor that contributes to the ability of the universal ultrasound probe to operate in multiple modes associated with different and medically-relevant frequency ranges is that the ultrasound transducers may be arranged in an array having an aperture (determined by the width and height of the array) that allows for both shallow and deep scans to be performed. For example, each mode may have a different active aperture. The total aperture accommodates the largest field-of-view needed to cover the application space of any one probe. Examples include all combinations of 1 cm, 2 cm, 3 cm, 4 cm, 5 cm in the azimuth direction and 1 cm, 2 cm, 3 cm, 4 cm, 5 cm in the elevation direction.

Another factor that contributes to the ability of the universal ultrasound probe to operate in multiple modes associated with different and medically-relevant frequency ranges is the selection of a CUT cell size. Grouping CUT cells together increases both directivity and sensitivity. In addition, directivity increases with frequency as the element remains fixed in size. Thus, grouping CUT cells together for lower frequencies can be balanced with less grouping for higher frequencies to maintain a consistent directivity.

Another factor that contributes to the ability of the universal ultrasound probe to operate in multiple modes associated with different and medically-relevant frequency ranges is that, in addition to being capable of operating in multiple frequency ranges, ultrasonic transducers in the probe are capable of generating low-frequency and high-frequency acoustic waveforms having a broad bandwidth (e.g., at least 100 KHz, at least 500 KHz, at least 1 MHz, at least 2 MHz, at least 5 MHz, at least 7 MHz, at least 15 MHz, at least 20 MHz, etc.).

Another factor that contributes to the ability of the universal ultrasound probe to operate in multiple modes associated with different and medically-relevant frequency ranges is that, in some embodiments, the probe may include programmable delay mesh circuitry that allows for transmit beamforming to focus at multiple depths, including depths in the range of 2-35 cm. Programmable delay mesh circuitry is further described in U.S. Pat. No. 9,229,097, assigned to the assignee of the present application, the contents of which are incorporated by reference herein in their entirety.

Still another factor that contributes to the ability of the universal ultrasound probe to operate in multiple modes associated with different and medically-relevant frequency ranges is that, in some embodiments, the probe may include circuitry that allows for receive beamforming to focus at multiple depths, including depths in the range of 2-35 cm.

In one exemplary embodiment, a universal ultrasound probe may include an array of 576×256 ultrasonic transducers, spaced at a pitch of 52 $\mu$m, and having an array aperture of about 3 cm×1.33 cm. At least some of the transducers can operate in a frequency range of 1-15 MHz with a bandwidth of 0.1-12 MHz. In another exemplary embodiment, a universal ultrasound probe may include an array of 64×140 transducers spaced at 208 $\mu$m, and having an array aperture of about 3 cm×1.33 cm, operating in a frequency range of 1.5-5 MHz, and from 5-12 MHz.

In some embodiments, a universal ultrasound probe (e.g., probe 100) may be implemented in any of numerous physical configurations, and has the capabilities incorporated to perform imaging in modes as may be used when imaging with two or more of the following: a linear probe, a sector probe, a phased array probe, a curvilinear probe, a convex probe, and/or a 3D imaging probe. Additionally, in some embodiments, the ultrasound probe may be embodied in a hand-held device. The hand-held device may include a screen to display obtained images (e.g., as shown in FIGS. 6A-6B). Additionally or alternatively, the hand-held device may be configured to transmit (via a wireless or a wired connection) data to an external device for further processing (e.g., to form one or more ultrasound images). As another example, in some embodiments, the ultrasound probe may be embodied in a pill (e.g., as shown in FIGS. 5A-5H) to be swallowed by a subject and configured to image the subject as it is traveling through his/her digestive system. As another example, in some embodiments, the ultrasound probe may be embodied in a patch configured to be affixed to the subject (e.g., as shown in FIGS. 7A-D).

The aspects and embodiments described above, as well as additional aspects and embodiments, are described further below. These aspects and/or embodiments may be used individually, all together, or in any combination of two or more, as the technology described herein is not limited in this respect.

Figure 1B:
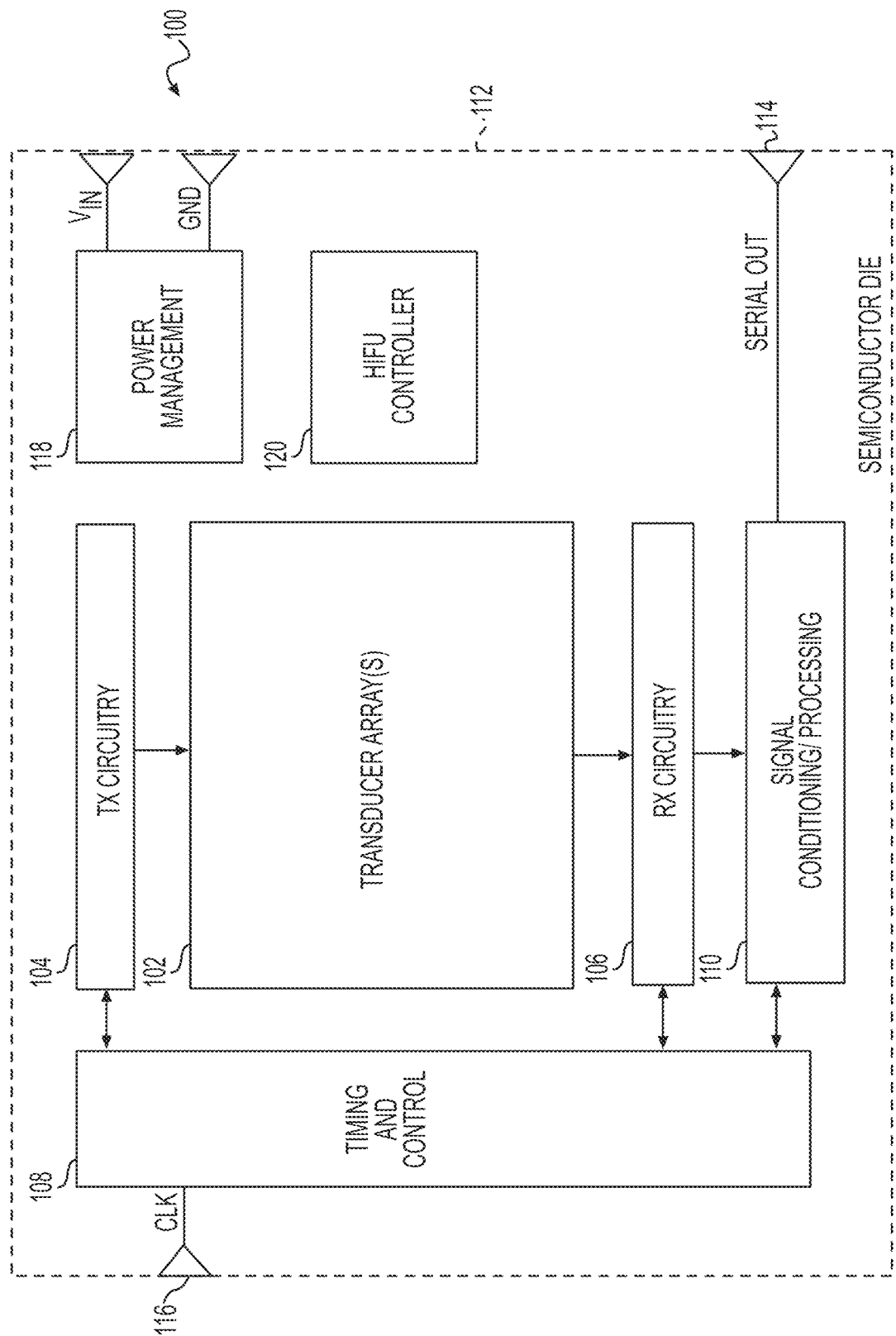
FIG. 1B is a block diagram of an illustrative example of a universal ultrasound device, in accordance with some embodiments of the technology described herein.

FIG. 1B shows an illustrative example of a monolithic ultrasound device 100 embodying various aspects of the technology described herein. As shown, the device 100 may include one or more transducer arrangements (e.g., arrays) 102, transmit (TX) circuitry 104, receive (RX) circuitry 106, a timing & control circuit 108, a signal conditioning/processing circuit 110, a power management circuit 118, and/or a high-intensity focused ultrasound (HIFU) controller 120. In the embodiment shown, all of the illustrated elements are formed on a single semiconductor die 112. It should be appreciated, however, that in alternative embodiments one or more of the illustrated elements may be instead located off-chip. In addition, although the illustrated example shows both TX circuitry 104 and RX circuitry 106, in alternative embodiments only TX circuitry or only RX circuitry may be employed. For example, such embodiments may be employed in a circumstance where one or more transmission-only devices 100 are used to transmit acoustic signals and one or more reception-only devices 100 are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, or one or more high-speed serial links (e.g. 1 Gbps, 2.5 Gbps, 5 Gbps, 10 Gbps, 20 Gbps) with any suitable combined bandwidth (e.g. 10 Gbps, 20 Gbps, 40 Gbps, 60 Gbps, 80 Gbps, 100 Gbps, 120 Gbps, 150 Gbps, 240 Gbps) may be used to allow high-speed intra-chip communication or communication with one or more off-chip components. In some embodiments, the communication with off-chip components may be in the analog domain, using analog signals.

The one or more transducer arrays 102 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 102 may, for example, include one or more capacitive micromachined ultrasonic transducers (CMUTs), one or more CMOS ultrasonic transducers (CUTs), one or more piezoelectric micromachined ultrasonic transducers (PMUTs), one or more broadband crystal transducers, and/or one or more other suitable ultrasonic transducer cells. In some embodiments, the transducer elements of the transducer array 102 may be formed on the same chip as the electronics of the TX circuitry 104 and/or RX circuitry 106 or, alternatively integrated onto the chip having the TX circuitry 104 and/or RX circuitry 106. In still other embodiments, the transducer elements of the transducer array 102, the TX circuitry 104 and/or RX circuitry 106 may be tiled on multiple chips.

The transducer arrays 102, TX circuitry 104, and RX circuitry 106 may be, in some embodiments, integrated in a single ultrasound probe. In some embodiments, the single ultrasound probe may be a hand-held probe including, but not limited to, the hand-held probes described below with reference to FIGS. 6A-B and 8. In other embodiments, the single ultrasound probe may be embodied in a patch that may be coupled to a patient. FIGS. 7A-D provide a non-limiting illustration of such a patch. The patch may be configured to transmit, wirelessly, data collected by the patch to one or more external devices for further processing. In other embodiments, the single ultrasound probe may be embodied in a pill that may be swallowed by a patient. The pill may be configured to transmit, wirelessly, data collected by the ultrasound probe within the pill to one or more external devices for further processing. FIGS. 5A-5H illustrate non-limiting examples of such a pill.

A CUT may include, for example, a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer). Such embodiments are further described with reference to FIG. 4 below, and additional information regarding microfabricated ultrasonic transducers may also be found in U.S. Pat. No. 9,067,779 and U.S. Patent Application Publication 2016/0009544 A1, both assigned to the assignee of the present application, and the contents of both of which are incorporated by reference herein in their entireties. It should be appreciated that the foregoing is just one example of an ultrasonic transducer. In some embodiments, the ultrasonic transducer (e.g., a CMUT) may be formed on a wafer separate from a substrate with circuitry. The wafer with the ultrasonic transducers may be bonded to an electrical substrate, which may be an interposer, a printed circuit board (pcb), an application specific circuit (ASIC) substrate, a substrate with analog circuitry, a substrate having integrated CMOS circuitry (a CMOS substrate), or any other substrate with electrical functionality. In some embodiments, the ultrasonic transducers may not be formed on a wafer. For example, broadband crystal transducers may be individually placed on a suitable substrate and coupled to an electrical substrate. Further alternatives are possible.

The TX circuitry 104 (if included) may, for example, generate pulses that drive the individual elements of, or one or more groups of elements within, the transducer array(s) 102 so as to generate acoustic signals to be used for imaging. The RX circuitry 106, on the other hand, may receive and process electronic signals generated by the individual elements of the transducer array(s) 102 when acoustic signals impinge upon such elements.

In some embodiments, the timing & control circuit 108 may be, for example, responsible for generating all timing and control signals that are used to synchronize and coordinate the operation of the other elements in the device 100. In the example shown, the timing & control circuit 108 is driven by a single clock signal CLK supplied to an input port 116. The clock signal CLK may be, for example, a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1) in the signal conditioning/processing circuit 110, or a 20 Mhz, 40 MHz, 100 MHz, 200 MHz, 250 MHz, 500 MHz, 750 MHz, or 1000 MHz clock used to drive other digital components on the die 112, and the timing & control circuit 108 may divide or multiply the clock CLK, as necessary, to drive other components on the die 112. In other embodiments, two or more clocks of different frequencies (such as those referenced above) may be separately supplied to the timing & control circuit 108 from an off-chip source.

The power management circuit 118 may be, for example, responsible for converting one or more input voltages VIN from an off-chip source into voltages needed to carry out operation of the chip, and for otherwise managing power consumption within the device 100. In some embodiments, for example, a single voltage (e.g., 0.4V, 0.9V, 1.5V, 1.8V, 2.5V, 3.3V, 5V, 12V, 80V, 100V, 120V, etc.) may be supplied to the chip and the power management circuit 118 may step that voltage up or down, as necessary, using a charge pump circuit or via some other DC-to-DC voltage conversion mechanism. In other embodiments, multiple different voltages may be supplied separately to the power management circuit 118 for processing and/or distribution to the other on-chip components.

As shown in FIG. 1B, in some embodiments, a HIFU controller 120 may be integrated on the die 112 so as to enable the generation of HIFU signals via one or more elements of the transducer array(s) 102. In other embodiments, a HIFU controller for driving the transducer array(s) 102 may be located off-chip, or even within a device separate from the device 100. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 120.

Moreover, it should be appreciated that the HIFU controller 120 may not represent distinct circuitry in those embodiments providing HIFU functionality. For example, in some embodiments, the remaining circuitry of FIG. 1B (other than the HIFU controller 120) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 114 may output a high-speed serial data stream generated by one or more components of the signal conditioning/processing circuit 110. Such data streams may be, for example, generated by one or more USB 2.0, 3.0 and 3.1 modules, and/or one or more 1 Gb/s, 10 Gb/s, 40 Gb/s, or 100 Gb/s Ethernet modules, integrated on the die 112. In some embodiments, the signal stream produced on output port 114 can be fed to a computer, tablet, or smartphone for the generation and/or display of 2-dimensional, 3-dimensional, and/or tomographic images. It should be appreciated that the listed images are only examples of possible image types. Other examples may include 1-dimensional images, 0-dimensional spectral Doppler images, and time-varying images, including images combing 3D with time (time varying 3D images). In embodiments in which image formation capabilities are incorporated in the signal conditioning/processing circuit 110, even relatively low-power devices, such as smartphones or tablets which have only a limited amount of processing power and memory available for application execution, can display images using only a serial data stream from the output port 114. As noted above, the use of on-chip analog-to-digital conversion and a high-speed serial data link to offload a digital data stream is one of the features that helps facilitate an "ultrasound on a chip" solution according to some embodiments of the technology described herein.

Devices 100 such as that shown in FIGS. 1A and 1B may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 102 (either together or individually) during one or more transmit phases, and receiving and processing signals generated by some or all of the elements in the array(s) 102 during one or more receive phases, such that during each receive phase the CMUT elements sense acoustic signals reflected by the subject. In other implementations, some of the elements in the array(s) 102 may be used only to transmit acoustic signals and other elements in the same array(s) 102 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 100 or on a single die 112.

Transmit and Receive Circuitry

Figure 2:
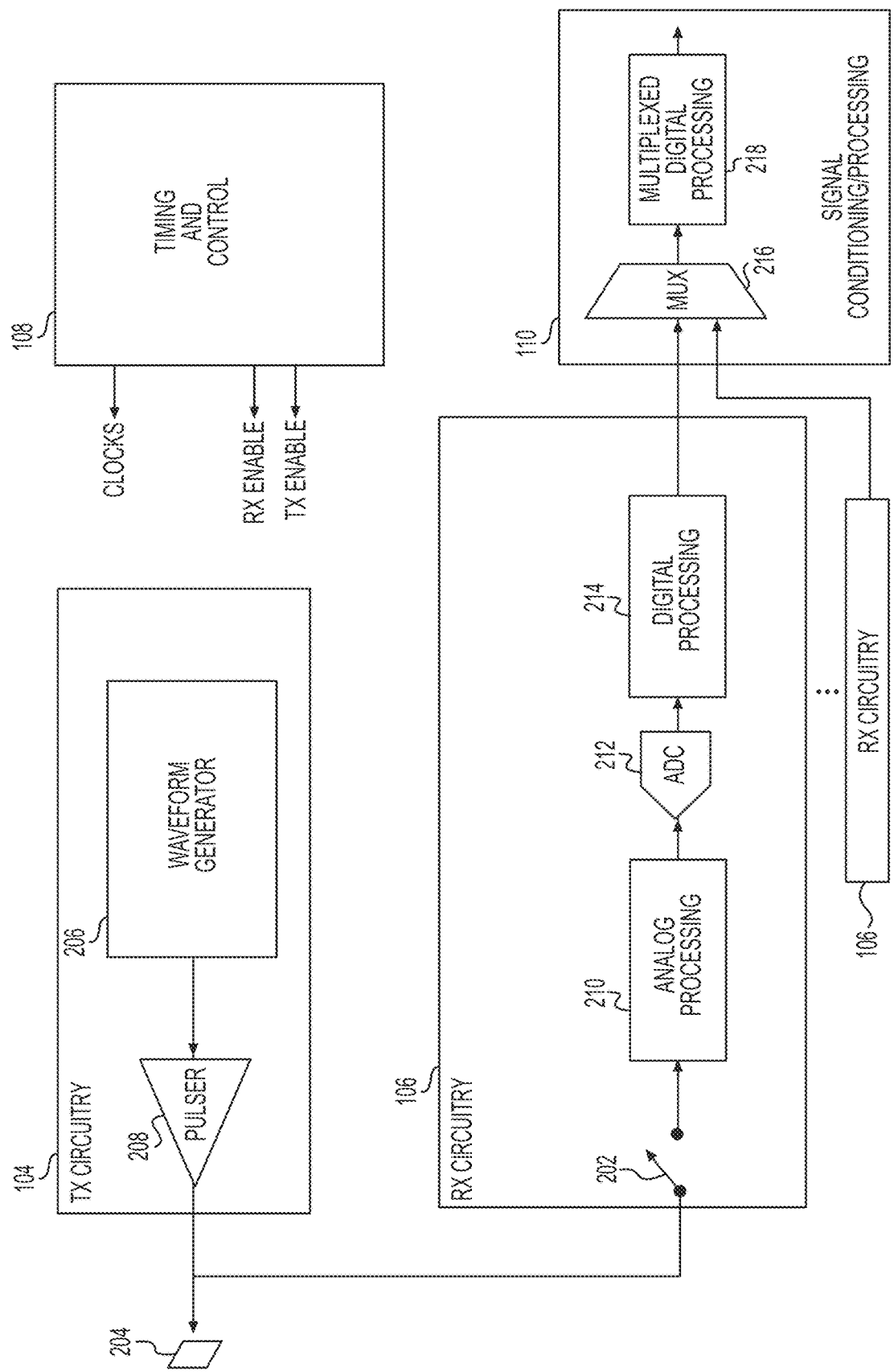
FIG. 2 is a block diagram illustrating how, in some embodiments, the transmit (TX) circuitry and the receive (RX) circuitry for a given transducer element of a universal ultrasound device may be used either to energize the element to emit an ultrasonic pulse, or to receive and process a signal from the element representing an ultrasonic pulse sensed by the transducer element, in accordance with some embodiments of the technology described herein.

FIG. 2 is a block diagram illustrating how, in some embodiments, the TX circuitry 104 and the RX circuitry 106 for a given transducer element 204 may be used either to energize the transducer element 204 to emit an ultrasonic pulse, or to receive and process a signal from the transducer element 204 representing an ultrasonic pulse sensed by it. In some implementations, the TX circuitry 104 may be used during a "transmission" phase, and the RX circuitry may be used during a "reception" phase that is non-overlapping with the transmission phase. As noted above, in some embodiments, a device 100 may alternatively employ only TX circuitry 104 or only RX circuitry 106, and aspects of the present technology do not necessarily require the presence of both such types of circuitry. In various embodiments, TX circuitry 104 and/or RX circuitry 106 may include a TX circuit and/or an RX circuit associated with a single transducer cell (e.g., a CUT or CMUT), a group of two or more transducer cells within a single transducer element 204, a single transducer element 204 comprising a group of transducer cells, a group of two or more transducer elements 204 within an array 102, or an entire array 102 of transducer elements 204.

In the example shown in FIG. 2, the TX circuitry 104/RX circuitry 106 includes a separate TX circuit and a separate RX circuit for each transducer element 204 in the array(s) 102, but there is only one instance of each of the timing & control circuit 108 and the signal conditioning/processing circuit 110. Accordingly, in such an implementation, the timing & control circuit 108 may be responsible for synchronizing and coordinating the operation of all of the TX circuitry 104/RX circuitry 106 combinations on the die 112, and the signal conditioning/processing circuit 110 may be responsible for handling inputs from all of the RX circuitry 106 on the die 112. In other embodiments, timing and control circuit 108 may be replicated for each transducer element 204 or for a group of transducer elements 204.

As shown in FIG. 2, in addition to generating and/or distributing clock signals to drive the various digital components in the device 100, the timing & control circuit 108 may output either an "TX enable" signal to enable the operation of each TX circuit of the TX circuitry 104, or an "RX enable" signal to enable operation of each RX circuit of the RX circuitry 106. In the example shown, a switch 202 in the RX circuitry 106 may always be opened during the TX circuitry 104 is enabled, so as to prevent an output of the TX circuitry 104 from driving the RX circuitry 106. The switch 202 may be closed when operation of the RX circuitry 106 is enabled, so as to allow the RX circuitry 106 to receive and process a signal generated by the transducer element 204.

As shown, the TX circuitry 104 for a respective transducer element 204 may include both a waveform generator 206 and a pulser 208. The waveform generator 206 may, for example, be responsible for generating a waveform that is to be applied to the pulser 208, so as to cause the pulser 208 to output a driving signal to the transducer element 204 corresponding to the generated waveform.

In the example shown in FIG. 2, the RX circuitry 106 for a respective transducer element 204 includes an analog processing block 210, an analog-to-digital converter (ADC) 212, and a digital processing block 214. The ADC 212 may, for example, comprise a 5-bit, 6-bit, 7-bit, 8-bit, 10-bit, 12-bit or 14-bit, and 5 MHz, 20 MHz, 25 MHz, 40 MHz, 50 MHz, or 80 MHz ADC. The ADC timing may be adjusted to run at sample rates corresponding to the mode based needs of the application frequencies. For example, a 1.5 MHz acoustic signal may be detected with a setting of 20 MHz. The choice of a higher vs. lower ADC rate provides a balance between sensitivity and power vs. lower data rates and reduced power, respectively. Therefore, lower ADC rates facilitate faster pulse repetition frequencies, increasing the acquisition rate in a specific mode and, in at least some embodiments, reducing the memory and processing requirements while still allowing for high resolution in shallow modes.

After undergoing processing in the digital processing block 214, the outputs of all of the RX circuits on the die 112 (the number of which, in this example, is equal to the number of transducer elements 204 on the chip) are fed to a multiplexer (MUX) 216 in the signal conditioning/processing circuit 110. In other embodiments, the number of transducer elements is larger than the number of RX circuits, and several transducer elements provide signals to a single RX circuit. The MUX 216 multiplexes the digital data from the RX circuits, and the output of the MUX 216 is fed to a multiplexed digital processing block 218 in the signal conditioning/processing circuit 110, for final processing before the data is output from the die 112, e.g., via one or more high-speed serial output ports 114. The MUX 216 is optional, and in some embodiments parallel signal processing is performed, for example where the output of each RX circuit is fed into a suitable dedicated digital processing block. A high-speed serial data port may be provided at any interface between or within blocks, any interface between chips and/or any interface to a host. Various components in the analog processing block 210 and/or the digital processing block 214 may reduce the amount of data that needs to be output from the die 112 via a high-speed serial data link or otherwise. In some embodiments, for example, one or more components in the analog processing block 210 and/or the digital processing block 214 may thus serve to allow the RX circuitry 106 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

Although particular components that may optionally be included in the analog processing block 210 are described below, it should be appreciated that digital counterparts to such analog components may additionally or alternatively be employed in the digital processing block 214. The converse is also true. That is, although particular components that may optionally be included in the digital processing block 214 are described below, it should be appreciated that analog counterparts to such digital components may additionally or alternatively be employed in the analog processing block 210.

Layout of Ultrasonic Transducers

Figure 3:
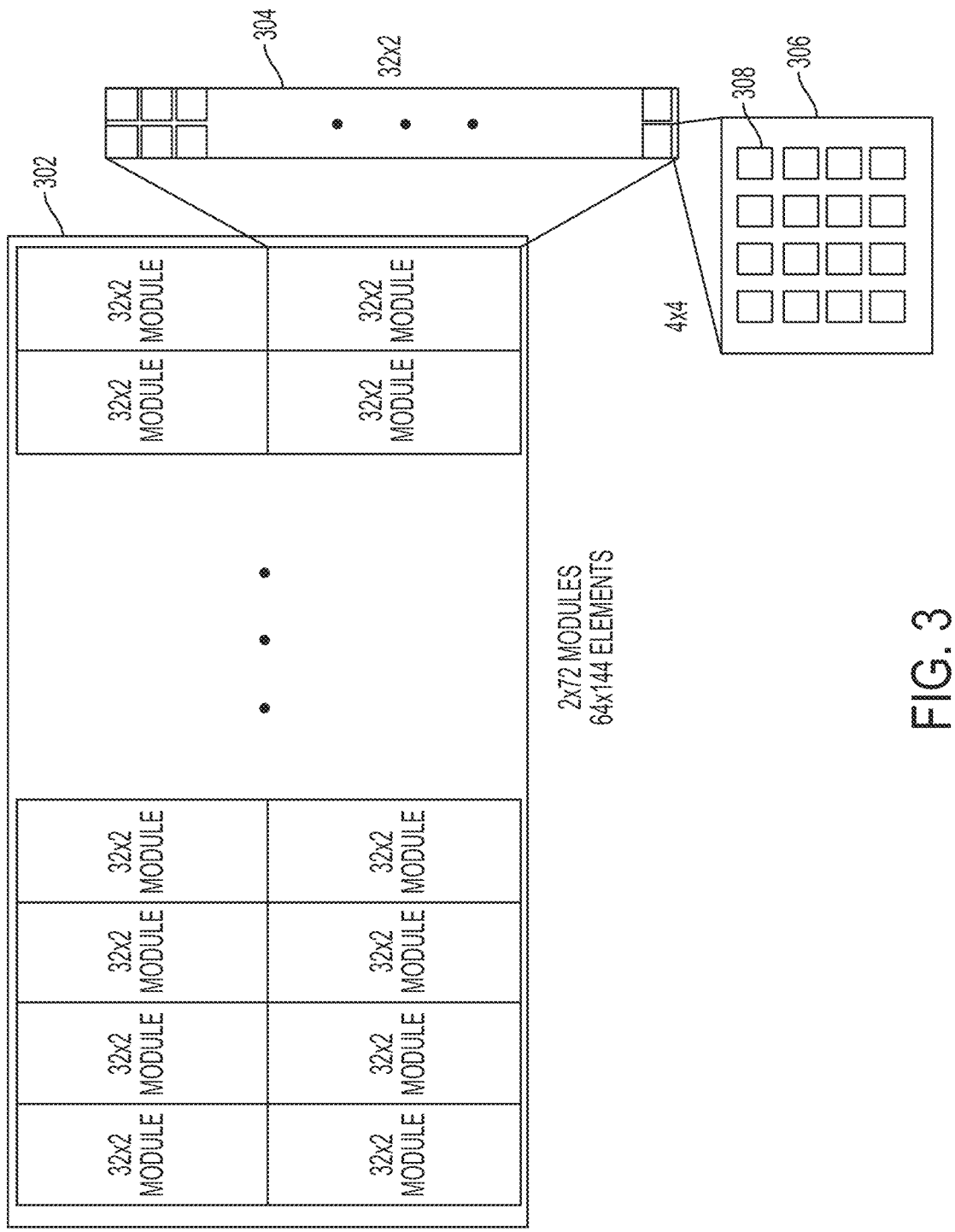
FIG. 3 shows an illustrative arrangement of ultrasonic transducers integrated with the substrate of a universal ultrasound device, in accordance with some embodiments of the technology described herein.

FIG. 3 shows substrate 302 (e.g., a semiconductor die) of an ultrasound device having multiple ultrasound circuitry modules 304 formed thereon. As shown, an ultrasound circuitry module 304 may comprise multiple ultrasound elements 306. An ultrasound element 306 may comprise multiple ultrasonic transducers 308, sometimes termed ultrasonic transducers.

In the illustrated embodiment, substrate 302 comprises 144 modules arranged as an array having two rows and 72 columns. However, it should be appreciated that a substrate of a single substrate ultrasound device may comprise any suitable number of ultrasound circuitry modules (e.g., at least two modules, at least ten modules, at least 100 modules, at least 400 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, or any number or range of numbers within such ranges) that may be arranged as an two-dimensional array of modules having any suitable number of rows and columns or in any other suitable way.

In the illustrated embodiment, each ultrasound circuitry module 304 comprises 64 ultrasound elements arranged as an array having 32 rows and two columns. However, it should be appreciated that an ultrasound circuitry module may comprise any suitable number of ultrasound elements (e.g., one ultrasound element, at least two ultrasound elements, at least four ultrasound elements, at least eight ultrasound elements, at least 16 ultrasound elements, at least 32 ultrasound elements, at least 64 ultrasound elements, at least 128 ultrasound elements, at least 256 ultrasound elements, at least 512 ultrasound elements, between two and 1024 elements, at least 2500 elements, at least 5,000 elements, at least 10,000 elements, at least 20,000 elements, between 5000 and 15000 elements, between 8000 and 12000 elements, between 1000 and 20,000 elements, or any number or range of numbers within such ranges) that may be arranged as a two-dimensional array of ultrasound elements having any suitable number of rows and columns or in any other suitable way.

In the illustrated embodiment, each ultrasound element 306 comprises 16 ultrasonic transducers arranged as a two-dimensional array having four rows and four columns. However, it should be appreciated that an ultrasound element may comprise any suitable number and/or groupings of ultrasonic transducer cells (e.g., one, at least two, four, at least four, 9, at least 9, at least 16, 25, at least 25, at least 36, at least 49, at least 64, at least 81, at least 100, between one and 200, or any number or range of numbers within such ranges) that may be arranged as a two dimensional array having any suitable number of rows and columns (square or rectangular) or in any other suitable way. In addition, the transducer cells may include shapes such as circular, oval, square, hexagonal, or other regular or irregular polygons, for example.

It should be appreciated that any of the components described above (e.g., ultrasound transmission units, ultrasound elements, ultrasonic transducers) may be arranged as a one-dimensional array, as a two-dimensional array, or in any other suitable manner.

In some embodiments, an ultrasound circuitry module may comprise circuitry in addition to one or more ultrasound elements. For example, an ultrasound circuitry module may comprise one or more waveform generators and/or any other suitable circuitry.

In some embodiments, module interconnection circuitry may be integrated with the substrate 302 and configured to connect ultrasound circuitry modules to one another to allow data to flow among the ultrasound circuitry modules. For example, the device module interconnection circuitry may provide for connectivity among adjacent ultrasound circuitry modules. In this way, an ultrasound circuitry module may be configured to provide data to and/or received data from one or more other ultrasound circuitry modules on the device.

Ultrasonic Transducers

The ultrasonic transducers of a universal ultrasound probe may be formed in any of numerous ways and, in some embodiments, may be formed as described with reference to FIG. 4.

Figure 4:
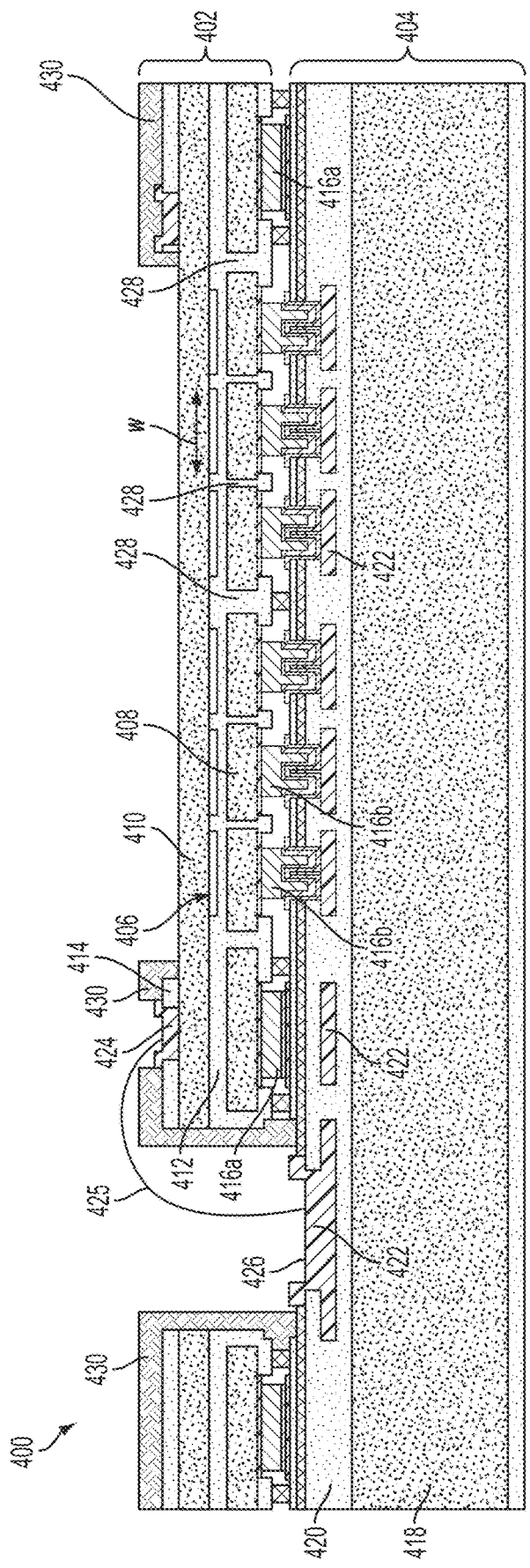
FIG. 4 is a cross-sectional view of a device including a CMOS wafer integrated with a substrate having sealed cavities, in accordance with some embodiments of the technology described herein.

FIG. 4 is a cross-sectional view of an ultrasound device including a CMOS wafer integrated with an engineered substrate having sealed cavities, according to a non-limiting embodiment of the present application. The device 400 may be formed in any suitable way and, for example, by implementing the methods described in the aforementioned U.S. Pat. No. 9,067,779.

The device 400 includes an engineered substrate 402 integrated with a CMOS wafer 404. The engineered substrate 402 includes a plurality of cavities 406 formed between a first silicon device layer 408 and a second silicon device layer 410. A silicon oxide ($SiO_2$) layer 412 (e.g., a thermal silicon oxide-a silicon oxide formed by thermal oxidation of silicon) may be formed between the first and second silicon device layers 408 and 410, with the cavities 406 being formed therein. In this non-limiting example, the first silicon device layer 408 may be configured as a bottom electrode and the second silicon device layer 410 may be configured as a membrane. Thus, the combination of the first silicon device layer 408, second silicon device layer 410, and cavities 406 may form an ultrasonic transducer (e.g., a CMUT), of which six are illustrated in this non-limiting cross-sectional view. To facilitate operation as a bottom electrode or membrane, one or both of the first silicon device layer 408 and second silicon device layer 410 may be doped to act as conductors, and in some cases are highly doped (e.g., having a doping concentration greater than 1015 dopants/cm 3 or greater). In some embodiments, the silicon oxide layer 412 containing the formed cavities may be formed as a plurality of insulating layers. For example, the silicon oxide layer 412 may comprise a first layer, with the formed cavities, and a second continuous layer with no cavities as an insulating layer for collapsed mode operation, for example.

The engineered substrate 402 may further include an oxide layer 414 on top of the second silicon device layer 410, which may represent the BOX layer of a silicon-on-insulator (SOI) wafer used to form the engineered substrate 402. The oxide layer 414 may function as a passivation layer in some embodiments and, as shown, may be patterned to be absent over the cavities 406. Contacts 424, and passivation layer 430 may be included on the engineered substrate 402. The passivation layer 430 may be patterned to allow access to one or more contacts 424, and may be formed of any suitable passivating material. In some embodiments, the passivation layer 430 is formed of silicon nitride $Si3N_4$ and in some embodiments is formed by a stack of SiO2 and $Si3N_4$, although alternatives are possible.

The engineered substrate 402 and CMOS wafer 404 may be bonded together at bond points 416a and 416b. The bond points may represent eutectic bond points, for example formed by a eutectic bond of a layer on engineered substrate 402 with a layer on CMOS wafer 404, or may be any other suitable bond type described herein (e.g., a silicide bond or thermocompression bond). In some embodiments, the bond points 416a and 416b may be conductive, for example being formed of metal. The bond points 416a may function solely as bond points in some embodiments, and in some embodiments may form a seal ring, for example hermetically sealing the ultrasonic transducers of the device 400, and improving device reliability. In some embodiments, the bond points 416a may define a seal ring that also provides electrical connection between the engineered substrate and CMOS wafer. Similarly, the bond points 416b may serve a dual purpose in some embodiments, for example serving as bond points and also providing electrical connection between the ultrasonic transducers of the engineered substrate 402 and the IC of the CMOS wafer 404. In those embodiments in which the engineered substrate is not bonded with a CMOS wafer the bond points 416b may provide electrical connection to any electrical structures on a substrate to which the engineered substrate is bonded.

The CMOS wafer 404 includes a base layer (e.g., a bulk silicon wafer) 418, an insulating layer 420 (e.g., SiO2), and a metallization 422. The metallization 422 may be formed of aluminum, copper, or any other suitable metallization material, and may represent at least part of an integrated circuit formed in the CMOS wafer. For example, metallization 422 may serve as a routing layer, may be patterned to form one or more electrodes, or may be used for other functions. In practice, the CMOS wafer 404 may include multiple metallization layers and/or post-processed redistribution layers, but for simplicity, only a single metallization is illustrated.

The bond points 416b may provide electrical connection between the metallization 422 of CMOS wafer 404 and the first silicon device layer 408 of the engineered substrate. In this manner, the integrated circuitry of the CMOS wafer 404 may communicate with (e.g., send electrical signals to and/or receive electrical signals from) the ultrasonic transducer electrodes and/or membranes of the engineered substrate. In the illustrated embodiments, a separate bond point 416b is illustrated as providing electrical connection to each sealed cavity (and therefore for each ultrasonic transducer), although not all embodiments are limited in this manner. For example, in some embodiments, the number of electrical contacts provided may be less than the number of ultrasonic transducers.

Electrical contact to the ultrasonic transducer membranes represented by second silicon device layer 410 is provided in this non-limiting example by contacts 424, which may be formed of metal or any other suitable conductive contact material. In some embodiments, an electrical connection may be provided between the contacts 424 and the bond pad 426 on the CMOS wafer. For example, a wire bond 425 may be provided or a conductive material (e.g., metal) may be deposited over the upper surface of the device and patterned to form a conductive path from the contacts 424 to the bond pad 426. However, alternative manners of connecting the contacts 424 to the IC on the CMOS wafer 404 may be used. In some embodiments an embedded via (not shown in FIG. 4) may be provided from the first silicon device layer 408 to a bottom side of the second silicon device layer 410, thus obviating any need for the contacts 424 on the topside of the second silicon device layer 410. In such embodiments, suitable electrical isolation may be provided relative to any such via to avoid electrically shorting the first and second silicon device layers.

The device 400 also includes isolation structures (e.g., isolation trenches) 428 configured to electrically isolate groups of ultrasonic transducers (referred to herein as "ultrasonic transducer elements") or, as shown in FIG. 4, individual ultrasonic transducers. The isolation structures 428 may include trenches through the first silicon device layer 408 that are filled with an insulating material in some embodiments. Alternatively, the isolation structures 428 may be formed by suitable doping. Isolation structures 428 are optional.

Various features of the device 400 are now noted. For instance, it should be appreciated that the engineered substrate 402 and CMOS wafer 404 wafer may be monolithically integrated, thus providing for monolithic integration of ultrasonic transducers with CMOS ICs. In the illustrated embodiment, the ultrasonic transducers are positioned vertically (or stacked) relative to the CMOS IC, which may facilitate formation of a compact ultrasound device by reducing the chip area required to integrate the ultrasonic transducers and CMOS IC.

Additionally, the engineered substrate 402 includes only two silicon layers 408 and 410, with the cavities 406 being formed between them. The first silicon device layer 408 and second silicon device layer 410 may be thin, for example each being less than 50 microns in thickness, less than 30 microns in thickness, less than 20 microns in thickness, less than 10 microns in thickness, less than 5 microns in thickness, less than 3 microns in thickness, or approximately 2 microns in thickness, among other non-limiting examples. In some embodiments it is preferable for one of the two wafers (e.g., silicon layer 408 or silicon layer 410) of the engineered substrate to be sufficiently thick to minimize vibration, prevent vibration or shift the frequency of unwanted vibration to a range outside of the operating range of the device, thereby preventing interference. Through modeling of the geometries in the physical stack of the transducer integrated with the CMOS, thicknesses of all layers can be optimized for transducer center frequency and bandwidth, with minimal interfering vibration. This may include, but is not limited to, changing layer thicknesses and features in the transducer engineered substrate and changing the thickness of the CMOS wafer 418. These layer thicknesses are also chosen to provide uniformity across the area of the array, and therefore tighter frequency uniformity, using commercially available wafers. The array may be substantially flat, in that the substrate may lack curvature. Still, as described herein, multiple ultrasound imaging modes may be achieved, including those for which curved transducer arrays are typically used. The lack of curvature of the substrate may be quantified in some embodiments as the substrate deviating from planar by no more than 0.5 cm across the array, e.g. deviation of 0.2 cm, 0.1 cm, or less.

Thus, while the engineered substrate may be thin, it may have a thickness of at least, for example, 4 microns in some embodiments, at least 5 microns in some embodiments, at least 7 microns in some embodiments, at least 10 microns in some embodiments, or other suitable thickness to prevent unwanted vibration. Such dimensions contribute to achieving a small device and may facilitate making electrical contact to the ultrasonic transducer membrane (e.g., second silicon device layer 410) without the need for thru-silicon vias (TSVs). TSVs are typically complicated and costly to implement, and thus avoiding use of them may increase manufacturing yield and reduce device cost. Moreover, forming TSVs requires special fabrication tools not possessed by many commercial semiconductor foundries, and thus avoiding the need for such tools can improve the supply chain for forming the devices, making them more commercially practical than if TSVs were used.

The engineered substrate 402 as shown in FIG. 4 may be relatively thin, for example being less than 100 microns in total thickness, less than 50 microns in total thickness, less than 30 microns in total thickness, less than 20 microns in total thickness, less than 10 microns in total thickness, or any other suitable thickness. The significance of such thin dimensions includes the lack of structural integrity and the inability to perform various types of fabrication steps (e.g., wafer bonding, metallization, lithography and etch) with layers having such initially thin dimensions. Thus, it is noteworthy that such thin dimensions may be achieved in the device 400, via a process sequence.

Also, the silicon device layers 408 and 410 may be formed of single crystal silicon. The mechanical and electrical properties of single crystal silicon are stable and well understood, and thus the use of such materials in an ultrasonic transducer (e.g., as the membrane of a CMUT) may facilitate design and control of the ultrasonic transducer behavior.

In one embodiment, there is a gap between parts of the CMOS wafer 404 and the first silicon device layer 408 since the two are bonded at discrete bond points 416b rather than by a bond covering the entire surface of the CMOS wafer 404. The significance of this gap is that the first silicon device layer 408 may vibrate if it is sufficiently thin. Such vibration may be undesirable, for instance representing unwanted vibration in contrast to the desired vibration of the second silicon device layer 410. Accordingly, it is beneficial in at least some embodiments for the first silicon device layer 408 to be sufficiently thick to minimize vibration, avoid vibration or shift the frequency of any unwanted vibration outside of the operating frequency range of the device.

In alternative embodiments, it may be desirable for both the first and second silicon device layers 408 and 410 to vibrate. For instance, they may be constructed to exhibit different resonance frequencies, thus creating a multi-frequency device. The multiple resonance frequencies (which may be related as harmonics in some embodiments) may be used, for example, in different operating states of an ultrasonic transducer. For example, the first silicon device layer 408 may be configured to resonate at half the center frequency of the second silicon device layer 410.

In still another embodiment, the strength of the bond between silicon device layer 410 and silicon oxide layer 412 allows for cavities 406 formed within silicon oxide layer 412 to have a larger diameter than would be possible with a weaker bond between layers 410 and 412. The diameter of a cavity is indicated as "w" in FIG. 4. The bond strength is provided at least in part by using a fabrication process in which the engineered substrate 402 is formed by bonding (e.g., at temperature less than about 400° C.) of two wafers, one containing silicon device layer 408 and the other containing silicon device layer 410, followed by a high temperature anneal (e.g., about 1000° C.). Ultrasonic transducers implemented using wide cavities may generate ultrasonic signals having more power at a particular frequency than ultrasonic signals generated at the same particular frequency by ultrasonic transducers implemented using cavities have a smaller diameter. In turn, higher power ultrasonic signals penetrate deeper into a subject being imaged thereby enabling high-resolution imaging of a subject at greater depths than possible with ultrasonic transducers having smaller cavities. For example, conventional ultrasound probes may use high frequency ultrasound signals (e.g., signals having frequencies in the 7-12 MHz range) to generate high-resolution images, but only at shallow depths due to the rapid attenuation of high-frequency ultrasound signals in the body of a subject being imaged. However, increasing the power of the ultrasonic signals emitted by an ultrasound probe (e.g., as enabled through the use of cavities having a larger diameter as made possible by the strength of the bond between layers 410 and 412) allows the ultrasonic signals to penetrate the subject deeper resulting in high-resolution images of the subject at greater depths than previously possible with conventional ultrasound probes.

Additionally, an ultrasonic transducer formed using a larger diameter cavity may generate lower frequency ultrasound signals than an ultrasonic transducer having a cavity with a smaller diameter. This extends the range of frequencies across which the ultrasonic transducer may operate. An additional technique may be to selectively etch and thin portions of the transducer top membrane 410. This introduces spring softening in the transducer membrane, thereby lowering the center frequency. This may be done on all, some or none of the transducers in the array in any combination of patterns.

Forms of Universal Ultrasound Device

A universal ultrasound device may be implemented in any of a variety of physical configurations including, for example, as a part of an internal imaging device, such as a pill to be swallowed by a subject or a pill mounted on an end of a scope or catheter, as part of a handheld device including a screen to display obtained images, as part of a patch configured to be affixed to the subject, or as part of a hand-held probe.

In some embodiments, a universal ultrasound probe may be embodied in a pill to be swallowed by a subject. As the pill travels through the subject, the ultrasound probe within the pill may image the subject and wirelessly transmit obtained data to one or more external devices for processing the data received from the pill and generating one or more images of the subject. For example, as shown in FIG. 5A, pill 502 comprising an ultrasound probe may be configured to communicate wirelessly (e.g., via wireless link 501) with external device 500, which may be a desktop, a laptop, a handheld computing device, and/or any other device external to pill 502 and configured to process data received from pill 502. A person may swallow pill 502 and, as pill 502 travels through the person's digestive system, pill 502 may image the person from within and transmit data obtained by the ultrasound probe within the pill to external device 500 for further processing. In some embodiments, the pill 502 may comprise an onboard memory and the pill 502 may store the data on the onboard memory such that the data may be recovered from the pill 502 once it has exited the person.

Figure 5B:
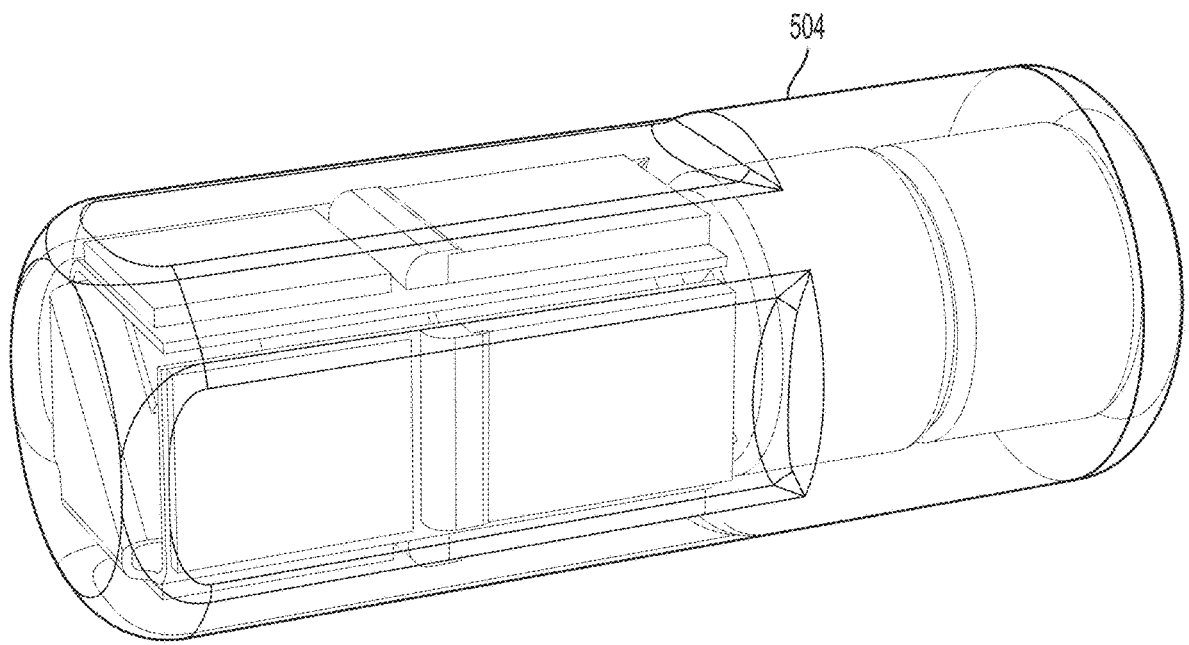
Figure 5C:
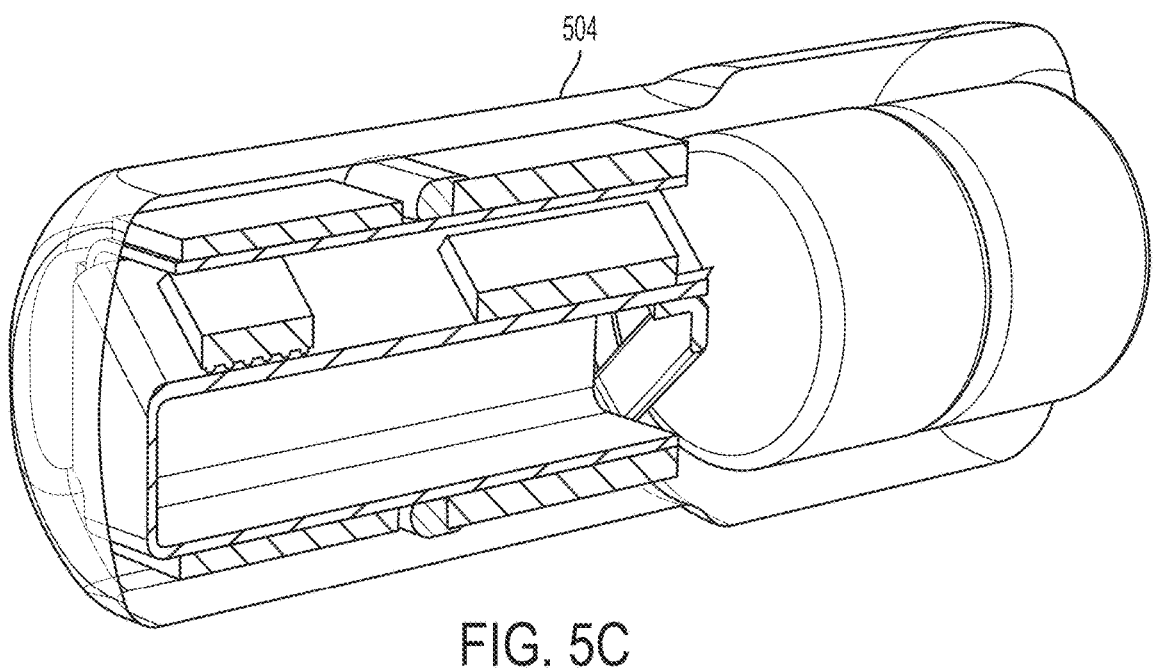
Figure 5D:
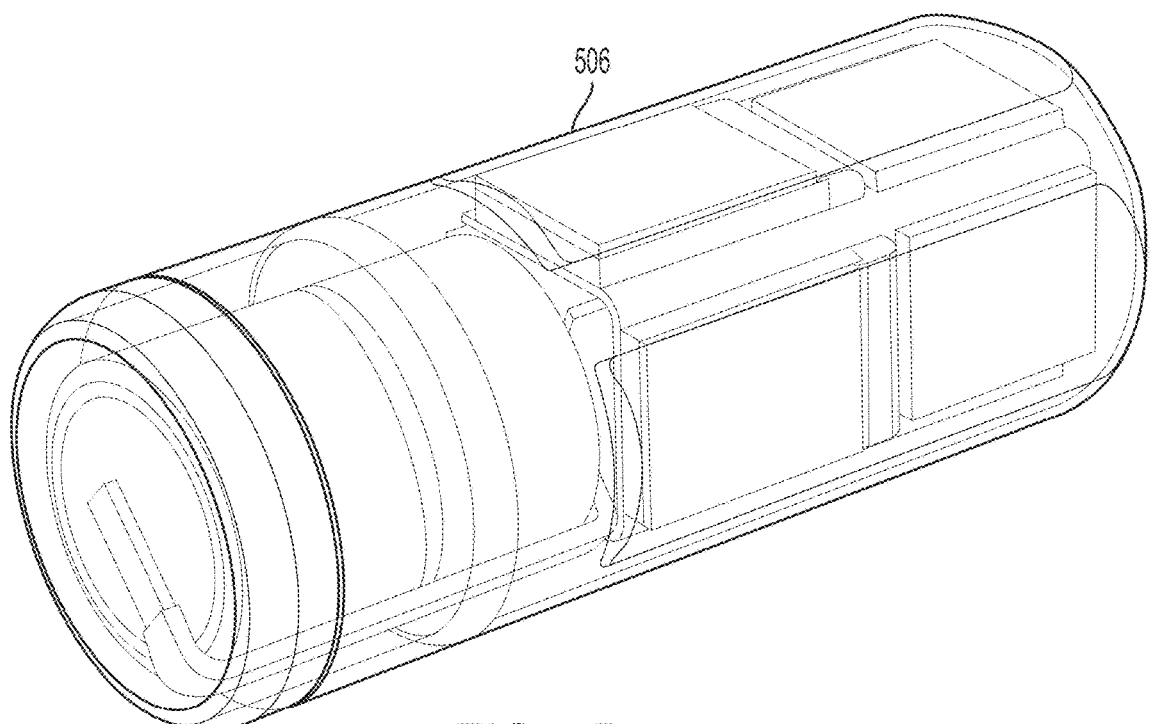
Figure 5E:
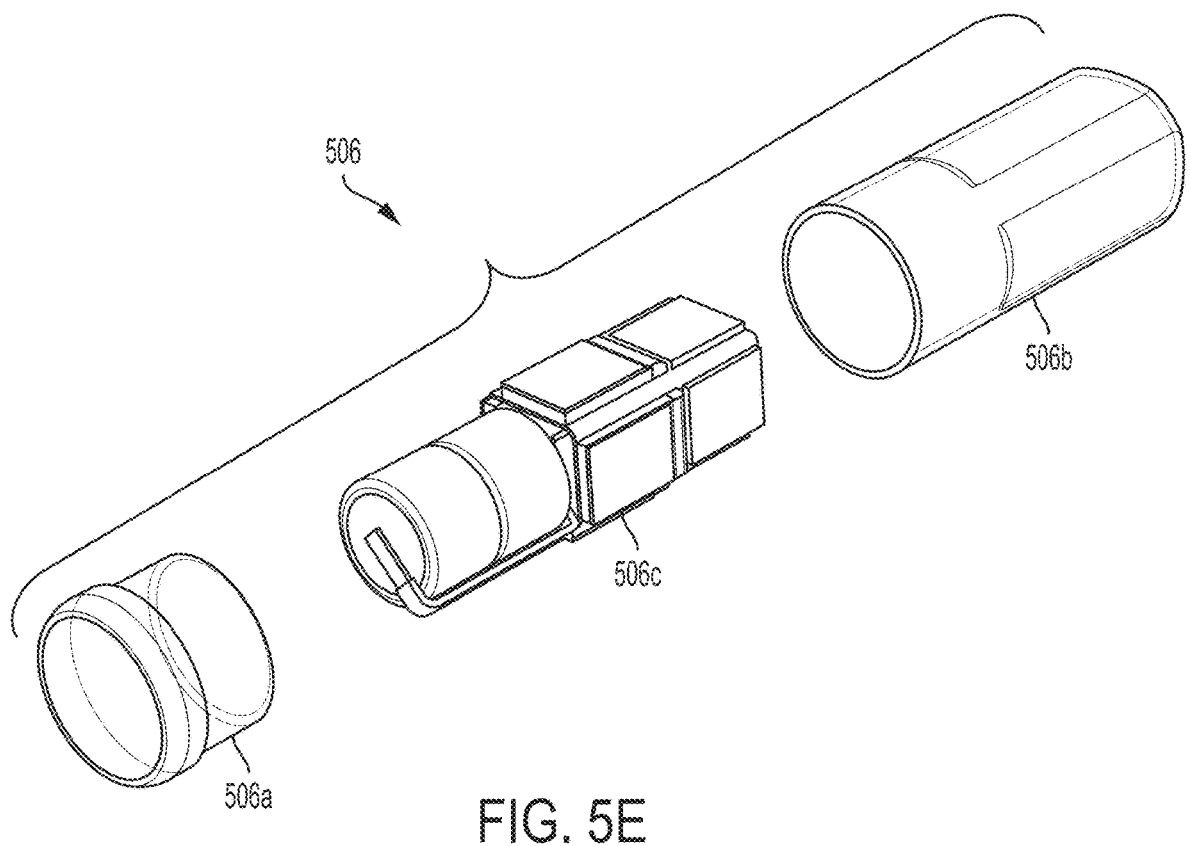
Figure 6A:
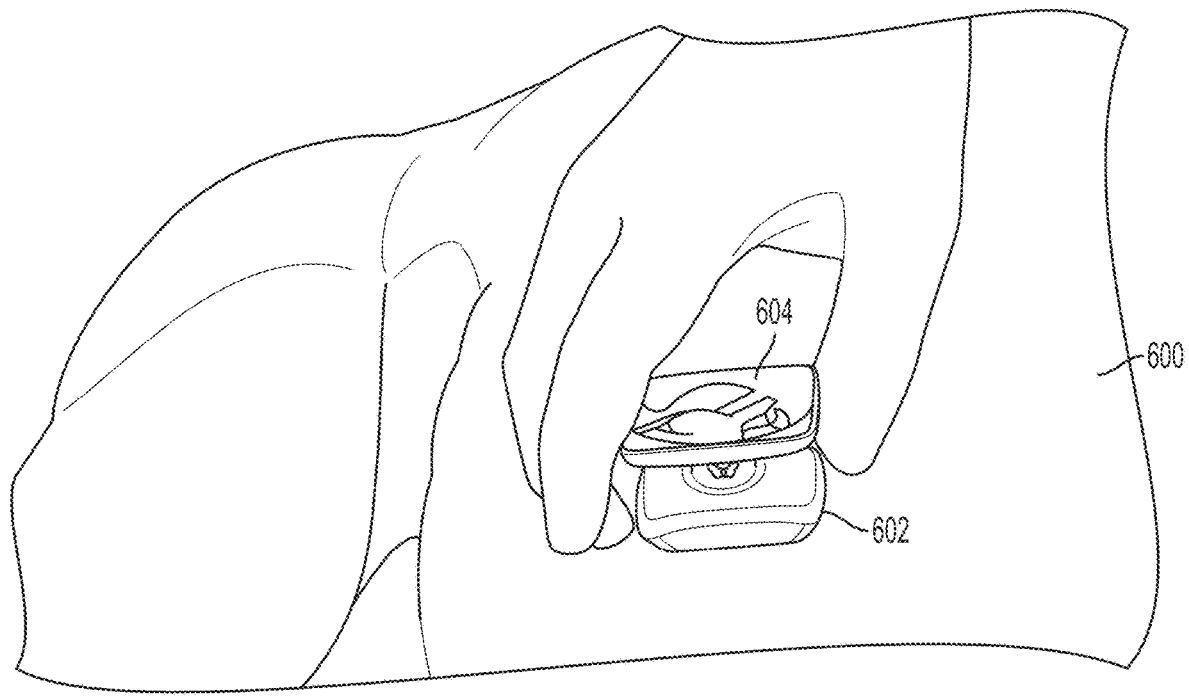
FIGS. 6A-6B illustrate a handheld device comprising an ultrasound probe and a display, in accordance with some embodiments of the technology described herein.
Figure 6B:
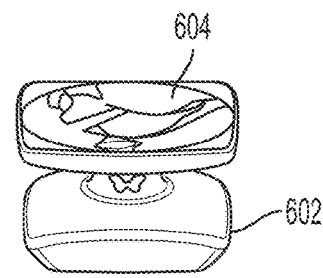

In some embodiments, a pill comprising an ultrasound probe may be implemented by potting the ultrasound probe within an outer case, as illustrated by an isometric view of pill 504 shown in FIG. 5B. FIG. 5C is a section view of pill 504 shown in FIG. 5B exposing views of the electronic assembly and batteries. In some embodiments, a pill comprising an ultrasound probe may be implemented by encasing the ultrasound probe within an outer housing, as illustrated by an isometric view of pill 506 shown in FIG. 5D. FIG. 5E is an exploded view of pill 506 shown in FIG. 5D showing outer housing portions 510a and 510b used to encase electronic assembly 510c.

Figure 5F:
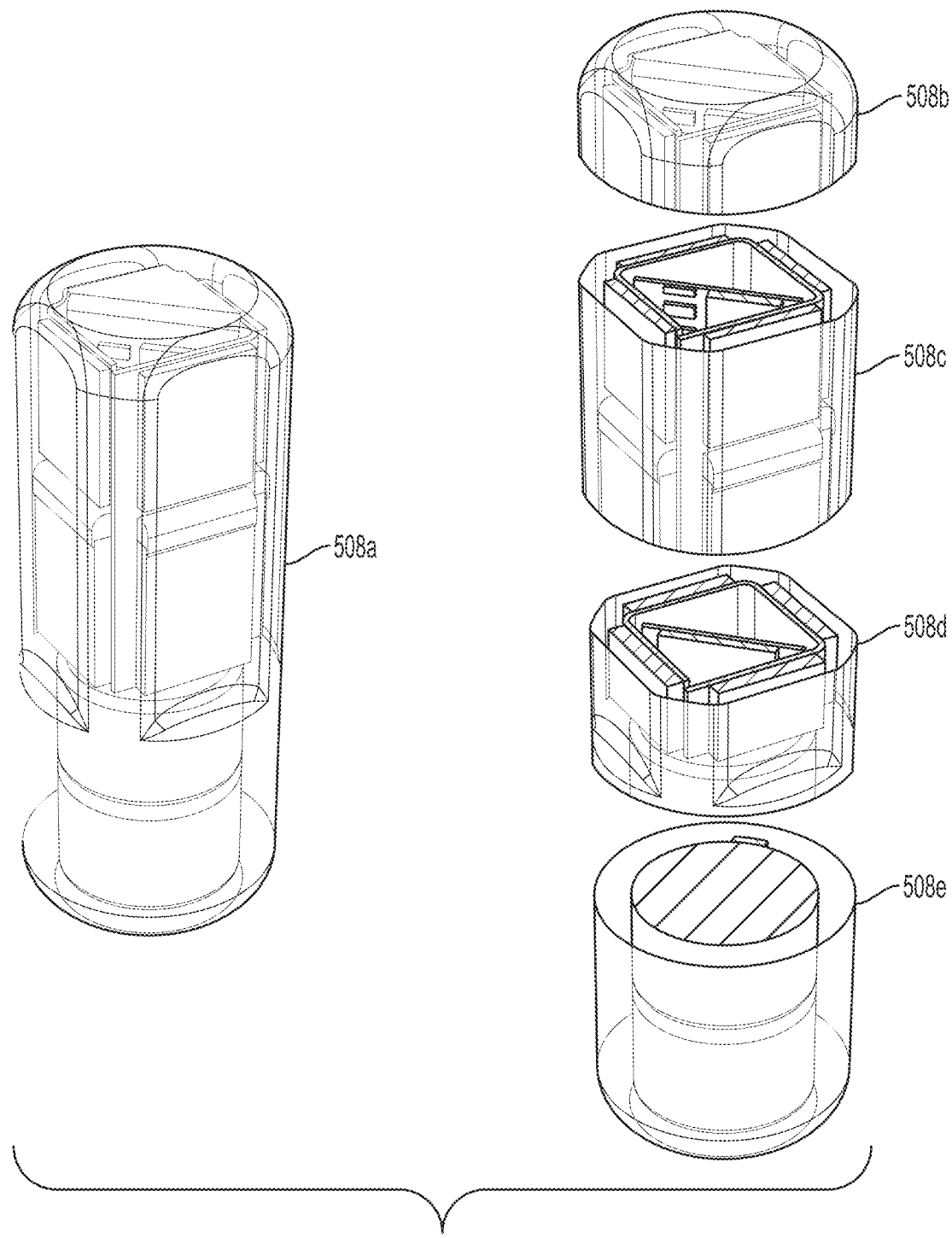
Figure 5G:
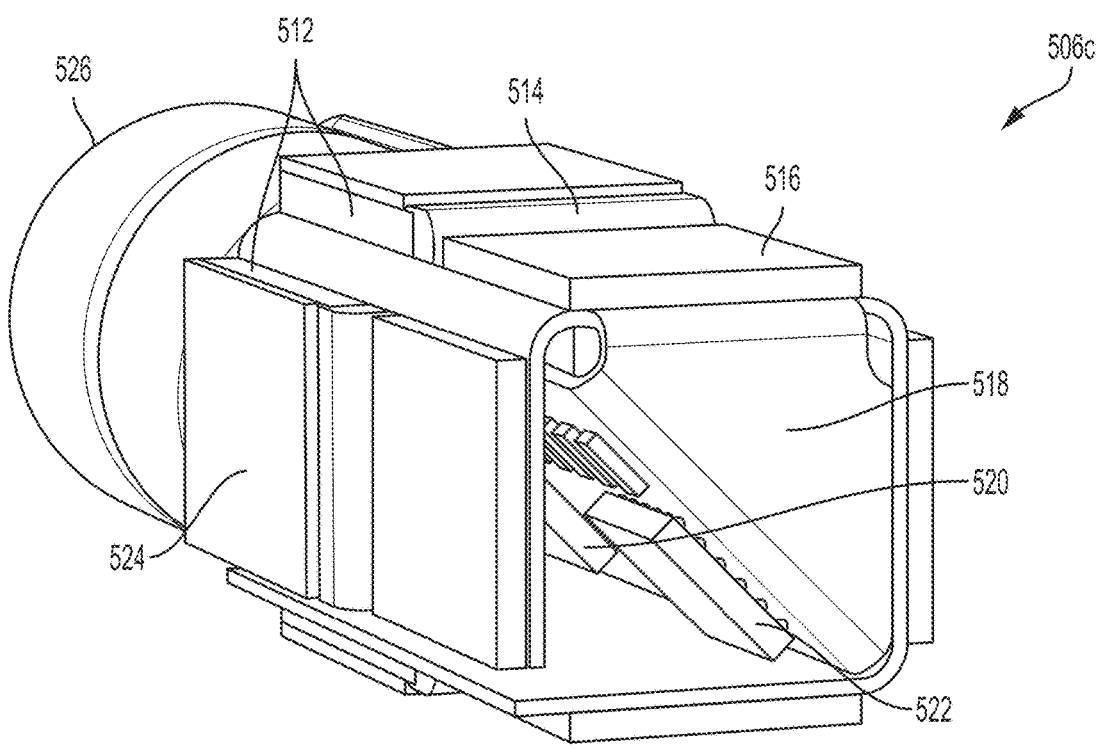
Figure 5H:
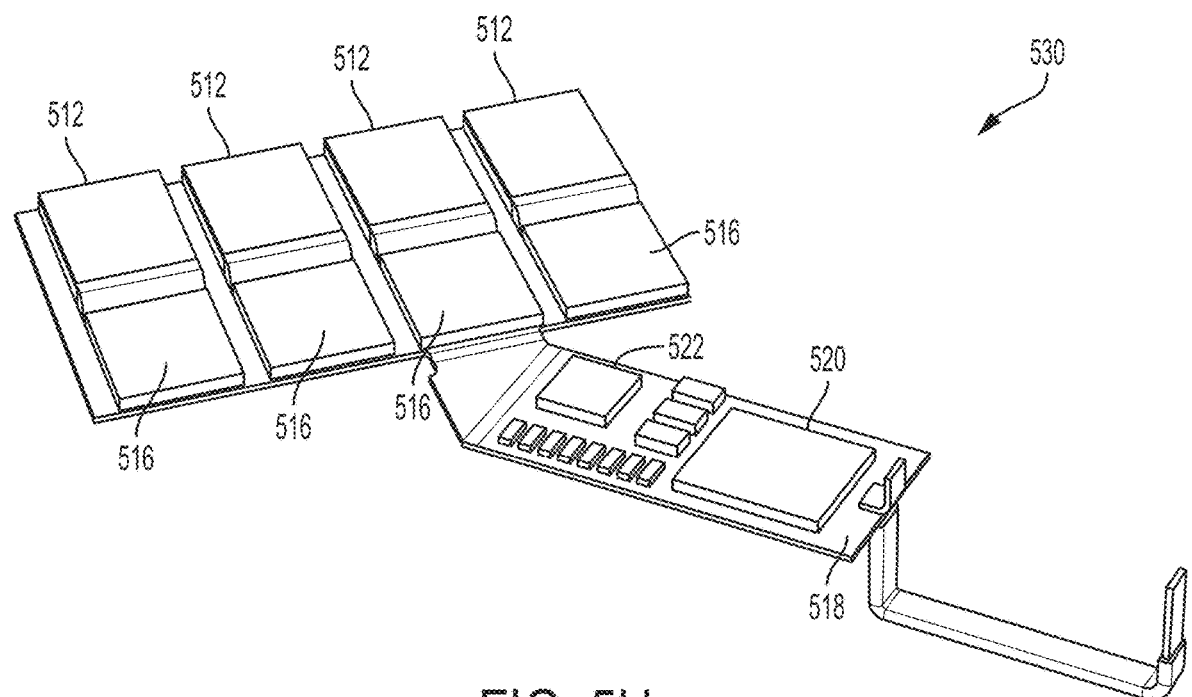

In some embodiments, the ultrasound probe implemented as part of a pill may comprise one or multiple ultrasonic transducer (e.g., CMUT) arrays, one or more image reconstruction chips, an FPGA, communications circuitry, and one or more batteries. For example, as shown in FIG. 5F, pill 508a may include multiple ultrasonic transducer arrays shown in sections 508b and 508c, multiple image reconstruction chips as shown in sections 508c and 508d, a Wi-Fi chip as shown in section 508d, and batteries as shown in sections 508d and 508e.

FIGS. 5G and 5H further illustrate the physical configuration of electronics module 506c shown in FIG. 5E. As shown in FIGS. 5G and 5H, electronics module 506c includes four CMUT arrays 512 (though more or fewer CMUT arrays may be used in other embodiments), bond wire encapsulant 514, four image reconstruction chips 516 (though more or fewer image reconstruction chips may be used in other embodiments), flex circuit 518, Wi-Fi chip 520, FPGA 522, and batteries 524. Each of the batteries may be of size 13 PR48. Each of the batteries may be a 300 mAh 1.4V battery. Other batteries may be used, as aspects of the technology described herein are not limited in this respect.

In some embodiments, the ultrasonic transducers of an ultrasound probe in a pill are physically arranged such that the field of view of the probe within the pill is equal to or as close to 360 degrees as possible. For example, as shown in FIGS. 5G and 5H, each of the four CMUT arrays may a field of view of approximately 60 degrees (30 degrees on each side of a vector normal to the surface of the CMUT array) or a field of view in a range of 40-80 degrees such that the pill consequently has a field of view of approximately 240 degrees or a field of view in a range of 160-320 degrees. In some embodiments, the field of view may be linear where under the array, rectilinear under the probe space, and trapezoidal out 30 degrees or for example any value between 15 degrees and 60 degrees, as a non-limiting example.

In some embodiments, a universal ultrasound probe may be embodied in a handheld device 602 illustrated in FIGS. 6A and 6B. Handheld device 602 may be held against (or near) a subject 600 and used to image the subject. Handheld device 602 may comprise an ultrasound probe (e.g., a universal ultrasound probe) and display 604, which in some embodiments, may be a touchscreen. Display 604 may be configured to display images of the subject generated within handheld device 602 using ultrasound data gathered by the ultrasound probe within device 602.

In some embodiments, handheld device 602 may be used in a manner analogous to a stethoscope. A medical professional may place handheld device 602 at various positions along a patient's body. The ultrasound probe within handheld device 602 may image the patient. The data obtained by the ultrasound probe may be processed and used to generate image(s) of the patient, which image(s) may be displayed to the medical professional via display 604. As such, a medical professional could carry hand-held device (e.g., around their neck or in their pocket) rather than carrying around multiple conventional probes, which is burdensome and impractical.

Figure 7A:
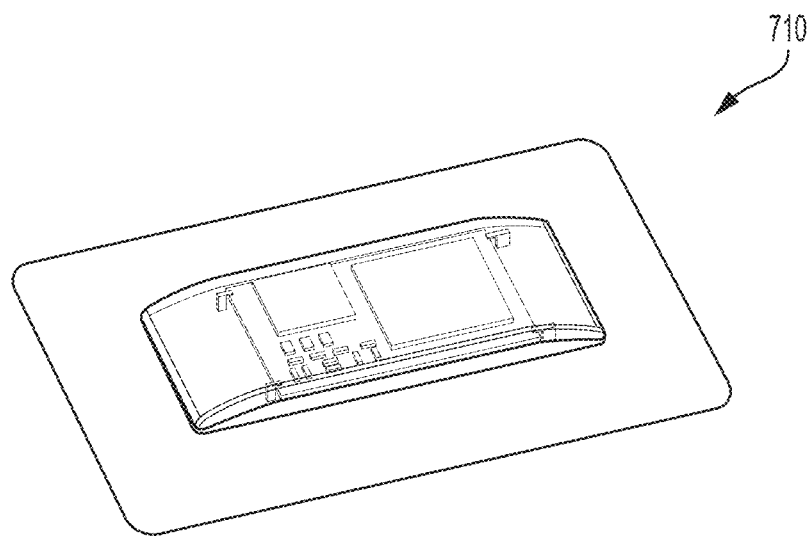
FIGS. 7A-7D illustrate a patch comprising an ultrasound probe, in accordance with some embodiments of the technology described herein.
Figure 7B:
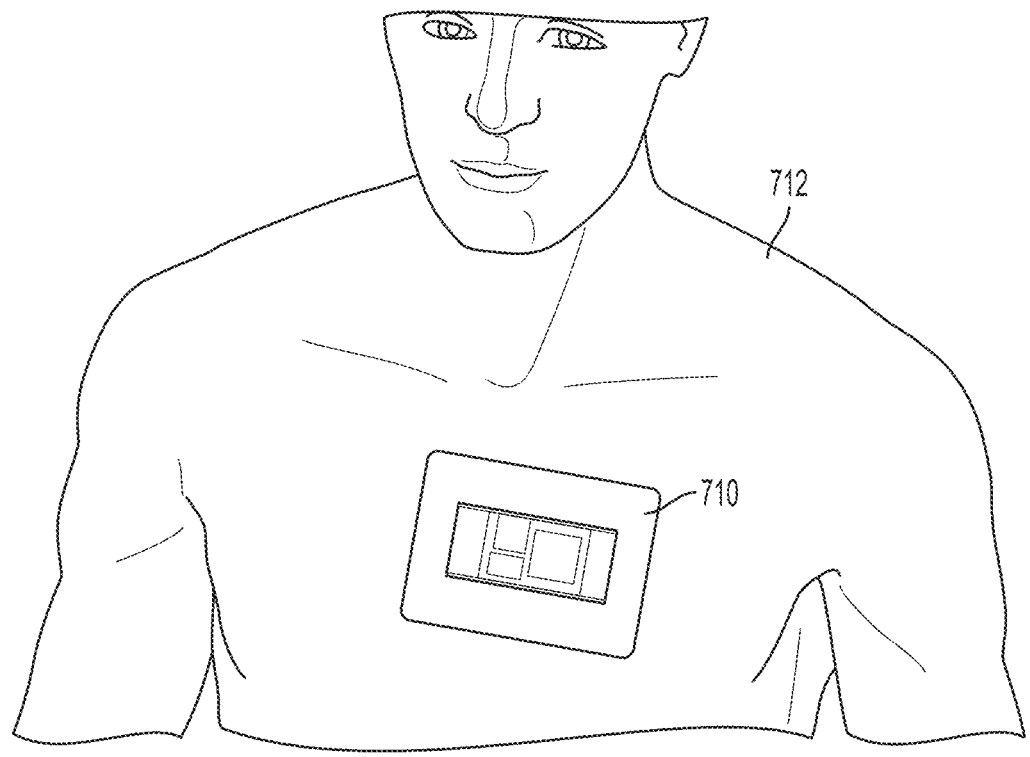

In some embodiments, a universal ultrasound probe may be embodied in a patch that may be coupled to a patient. For example, FIGS. 7A and 7B illustrate a patch 710 coupled to patient 712. The patch 710 may be configured to transmit, wirelessly for example, data collected by the patch 710 to one or more external devices (not shown) for further processing. For purposes of illustration, a top housing of the patch 710 is depicted in a transparent manner to depict exemplary locations of various internal components of the patch.

Figure 7C:
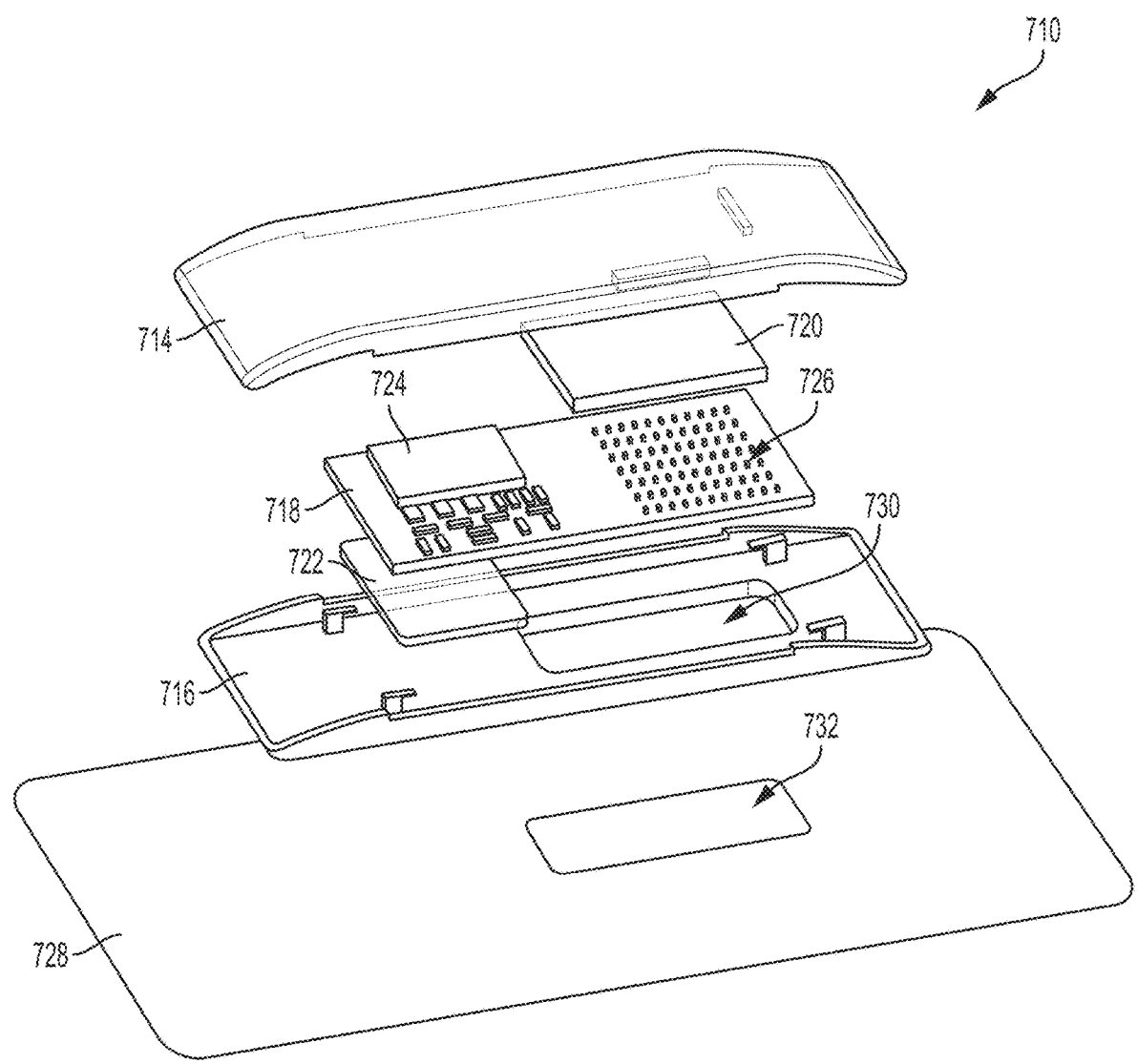
Figure 7D:
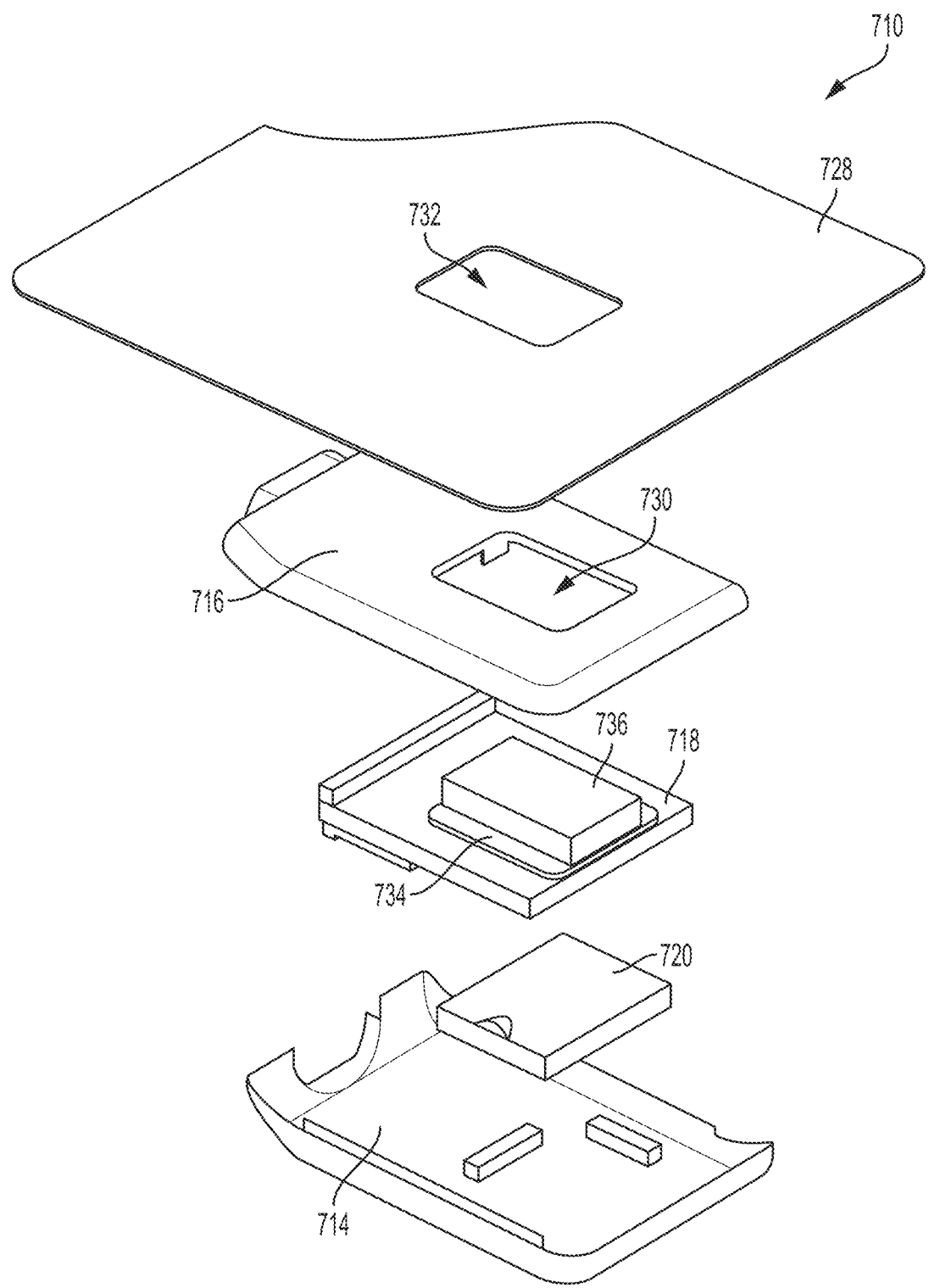

FIGS. 7C and 7D show exploded views of patch 710. As particularly illustrated in FIG. 7C, patch 710 includes upper housing 714, lower housing 716, and circuit board 718. Circuit board 718 may be configured to support various components, such as for example heat sink 720, battery 722 and communications circuitry 724. In one embodiment, communication circuitry 724 includes one or more short- or long-range communication platform. Exemplary short-range communication platforms include, Bluetooth (BT), Bluetooth Low Energy (BLE), Near-Field Communication (NFC). Long-range communication platforms include, Wi-Fi and Cellular. While not shown, the communication platform may include front-end radio, antenna and other processing circuitry configured to communicate radio signal to and auxiliary device (not shown). The radio signal may include ultrasound imaging information obtained by patch 710.

In an exemplary embodiment, communication circuitry transmits periodic beacon signals according to IEEE 802.11 and other prevailing standards. The beacon signal may include a BLE advertisement. Upon receipt of the beacon signal or the BLE advertisement, an auxiliary device (not shown) may respond to patch 710. That is, the response to the beacon signal may initiate a communication handshake between patch 710 and the auxiliary device.

The auxiliary device may include laptop, desktop, smartphone or any other device configured for wireless communication. The auxiliary device may act as a gateway to cloud or internet communication. In an exemplary embodiment, the auxiliary device may include the patient's own smart device (e.g., smartphone) which communicatively couples to patch 710 and periodically receives ultrasound information from patch 710. The auxiliary device may then communicate the received ultrasound information to external sources.

Circuit board 718 may comprise one or more processing circuitry, including one or more controllers to direct communication through communication circuitry 724. For example, circuit board 718 may engage communication circuitry periodically or on as-needed basis to communicate information with one or more auxiliary devices. Ultrasound information may include signals and information defining an ultrasound image captured by patch 710. Ultrasound information may also include control parameters communicated from the auxiliary device to patch 710. The control parameters may dictate the scope of the ultrasound image to be obtained by patch 710.

In one embodiment, the auxiliary device may store ultrasound information received from patch 710. In another embodiment, the auxiliary device may relay ultrasound information received from patch 710 to another station. For example, the auxiliary device may use Wi-Fi to communicate the ultrasound information received from patch 710 to a cloud-based server. The cloud-based server may be a hospital server or a server accessible to the physician directing ultrasound imaging. In another exemplary embodiment, patch 710 may send sufficient ultrasound information to the auxiliary device such that the auxiliary device may construct an ultrasound image therefrom. In this manner, communication bandwidth and power consumption may be minimized at patch 710.

In still another embodiment, the auxiliary device may engage patch 710 through radio communication (i.e., through communication circuitry 724) to actively direct operation of patch 710. For example, the auxiliary device may direct patch 710 to produce ultrasound images of the patient at periodic intervals. The auxiliary device may direct the depth of the ultrasound images taken by patch 710. In still another example, the auxiliary device may control the manner of operation of the patch so as to preserve power consumption at battery 722. Upon receipt of ultrasound information from patch 710, the auxiliary device may operate to cease imaging, increase imaging rate or communicate an alarm to the patient or to a third party (e.g., physician or emergency personnel).

It should be noted that the communication platform described in relation with FIG. 7 may also be implemented in other form-factors disclosed herein. For example, the communication platform (including control circuitry and any interface) may be implemented in the ultrasound pill as illustrated in FIGS. 5A-5H, the handheld device as illustrated in FIGS. 6A-6B or the handheld probe as illustrated in FIG. 8.

As shown in FIG. 7C, a plurality of through vias 726 (e.g., copper) may be used for a thermal connection between heat sink 720 and one or more image reconstruction chips (e.g., CMOS) (not shown in FIG. 7C). As further depicted in FIG. 7C, patch 710 may also include dressing 728 that provides an adhesive surface for both the patch housing as well as to the skin of a patient. One non-limiting example of such a dressing 728 is Tegaderm™, a transparent medical dressing available from 3M Corporation. Lower housing 716 includes a generally rectangular shaped opening 730 that aligns with another opening 732 in dressing 728.

Referring to FIG. 7D, another "bottom up" exploded view of the patch 710 illustrates the location of ultrasonic transducers and integrated CMOS chip (generally indicated by 734) on circuit board 718. An acoustic lens 736 mounted over the transducers/CMOS 734 is configured to protrude through openings 730, 732 to make contact with the skin of a patient. Although the embodiment of FIGS. 7A-7D depict an adhesive dressing 728 as a means of affixing patch 710 to patient 712, it will be appreciated that other fastening arrangements are also contemplated. For example, a strap (not shown) may be used in lieu of (or in addition to) dressing 728 in order to secure the patch 710 at a suitable imaging location.

Figure 8:
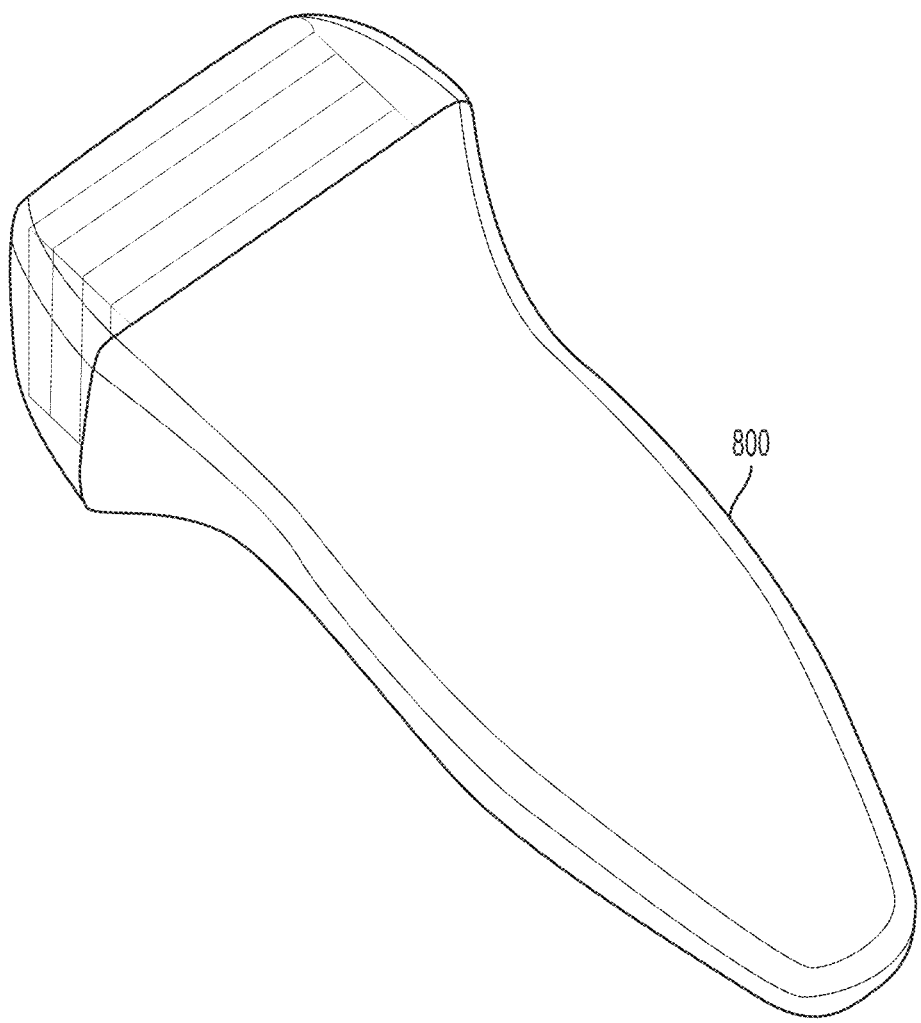
FIG. 8 is a diagram illustrating a handheld probe comprising an ultrasound probe, in accordance with some embodiments of the technology described herein.

In some embodiments, a universal ultrasound probe may be embodied in hand-held probe 800 shown in FIG. 8. Hand-held probe 800 may be configured to transmit data collected by the probe 800 wirelessly to one or more external host devices (not shown in FIG. 8) for further processing. In other embodiments, hand-held probe 800 may be configured transmit data collected by the probe 800 to one or more external devices using one or more wired connections, as aspects of the technology described herein are not limited in this respect.

Some embodiments of the technology described herein relate to an ultrasound device that may be configured to operate in any one of multiple operating modes. Each of the operating modes may be associated with a respective configuration profile that specifies a plurality of parameter values used for operating the ultrasound device. In some embodiments, the operating mode of the ultrasound device may be selected by a user, for example, via a graphical user interface presented by a mobile computing device communicatively coupled to the ultrasound device. In turn, an indication of the operating mode selected by the user may be communicated to the ultrasound device, and the ultrasound device may: (1) access a configuration profile associated with the selected operating mode; and (2) use parameter values specified by the accessed configuration profile to operate in the selected operating mode.

Accordingly, some embodiments provide for a system comprising: (1) an ultrasound device (e.g., a handheld ultrasound probe or a wearable ultrasound probe) having a plurality of ultrasonic transducers and control circuitry; and (2) a computing device (e.g., a mobile computing device such as a smart phone) that allows a user to select an operating mode for the ultrasound device (e.g., via a graphical user interface presented to the user via a display coupled to and/or integrated with the computing device) and provides an indication of the selected operating mode to the ultrasound device. In turn, the control circuitry in ultrasound device may: (1) receive the indication of the selected operating mode; (2) responsive to receiving an indication of the first operating mode: obtain a first configuration profile specifying a first set of parameter values associated with the first operating mode; and control, using the first configuration profile, the ultrasound device to operate in the first operating mode; and (3) responsive to receiving an indication of the second operating mode, obtain a second configuration profile specifying a second set of parameter values associated with the second operating mode; and control, using the second configuration profile, the ultrasound device to operate in the second operating mode.

In some embodiments, different configuration profiles for different operating modes include different parameter values for one or more parameters used for operating the ultrasound device. For example, in some embodiments, different configuration profiles may specify different azimuth aperture values, elevation aperture values, azimuth focus values, elevation focus values, transducer bias voltage values, transmit peak-to-peak voltage values, transmit center frequency values, receive center frequency values, polarity values, ADC clock rate values, decimation rate values, and/or receive duration values. It should be appreciated that other parameters may be used in the configuration profiles, such as receive start time, receive offset, transmit spatial amplitude, transmit waveform, pulse repetition interval, axial resolution, lateral resolution at focus, elevational resolution at focus, and signal gain. It should be appreciated that two different configuration profiles for two different operating modes may differ in any suitable number of parameter values (e.g., at least one parameter value, at least two parameter values, at least five parameter values, etc.), as aspects of the technology described herein are not limited in this respect. The configuration profiles may differ in one or more of the above-described parameter values and/or any other suitable parameter values. Examples of parameter values for different operating modes are provided in Tables 2-4 below. Each of the rows of the Tables 2-4 indicates illustrative parameter values for a particular configuration profile associated with a respective operating mode.

As one example, a first configuration profile for a first operating mode may specify a first azimuth aperture value and a second configuration profile for a second operating mode may specify a second azimuth aperture value different from the first azimuth aperture value. As another example, a first configuration profile for a first operating mode may specify a first elevation aperture value and a second configuration profile for a second operating mode may specify a second elevation aperture value different from the first elevation aperture value. The azimuth and elevation aperture values for an operating mode may control the size of the active aperture of the transducer array in the ultrasound probe. The physical aperture of the array, which is determined by the width and height of the array, may be different from the active aperture of the array as used in a particular operating mode. Indeed, the transducer arrangement may be configured to provide multiple possible active apertures. For example, only some of the transducers may be used for transmitting/receiving ultrasound signals, which results in the active aperture of the array being different from what the aperture would be if all the ultrasound transducers were used. In some embodiments, the azimuth and elevation aperture values may be used to determine which subset of transducer elements are to be used for transmitting/receiving ultrasound signals. In some embodiments, the azimuth and elevation aperture values may indicate, as a function of length, an extent of the transducer array used in the azimuthal and elevational orientations, respectively.

As another example, a first configuration profile for a first operating mode may specify a first azimuth focus value and a second configuration profile for a second operating mode may specify a second azimuth focus value different from the first azimuth focus value. As another example, a first configuration profile for a first operating mode may specify a first elevation focus value and a second configuration profile for a second operating mode may specify a second elevation focus value different from the first elevation focus value. The azimuthal and elevational focus values may be used to control the focal point of the transducer array independently in two dimensions. As such, different foci may be selected for the elevation and azimuthal dimensions. The focal point may be varied as between different operating modes either independently or together. The azimuth and elevation focus values may be used to control the programmable delay mesh circuitry in order to operate the ultrasound probe to have the focal point defined by the azimuth and elevation focus values.

As another example, a first configuration profile for a first operating mode may specify a first bias voltage value (for biasing the voltage across one or more ultrasonic transducers of the ultrasound probe) and a second configuration profile for a second operating mode may specify a second bias voltage value different from the first bias voltage value. As described herein, ultrasonic transducers may operate in collapsed mode or in non-collapsed mode. In some embodiments, application of at least a threshold bias voltage (a "collapse" voltage) across one or more ultrasound transducers may cause these transducers to operate in collapsed mode.

As another example, a first configuration profile for a first operating mode may specify a first transmit peak-to-peak voltage value (e.g., the voltage value for the electrical signal representing the transmit waveform) and a second configuration profile for a second operating mode may specify a second transmit peak-to-peak voltage value different from the first transmit peak-to-peak voltage value. The transmit peak-to-peak voltage value may represent the peak-to-peak voltage swing in amplitude (in Volts) for the transducer driver. Different peak-to-peak voltage swings may be used in different operating modes. For example, an operating mode for near-field imaging may use a smaller peak-to-peak voltage swing (than what might be used in other operating modes) to prevent saturating the receivers in the near-field range. A higher voltage peak-to-peak voltage swing may be used for deeper imaging, for generation of tissue harmonics, or for imaging with diverging or plane waves, for example.

As another example, a first configuration profile for a first operating mode may specify a first transmit center frequency value (e.g., the center frequency of an ultrasound signal transmitted by the ultrasound transducers) and a second configuration profile for a second operating mode may specify a second transmit center frequency value different from the first transmit center frequency value. In some embodiments, the difference between the first and second center frequencies may be at least 1 MHz, at least 2 MHz, between 5 MHz and 10 MHz. In some embodiments, the first center frequency value may be within the 1-5 MHz range and the second center frequency value may be within the 5-9 MHz range. In some embodiments, the first center frequency value may be within the 2-4 MHz range and the second center frequency value may be within the 6-8 MHz range.

As another example, a first configuration profile for a first operating mode may specify a first receive center frequency value (e.g., the center frequency of an ultrasound signal received by the ultrasound transducers) and a second configuration profile for a second operating mode may specify a second receive center frequency value different from the first receive center frequency value. In some embodiments, a configuration profile may specify a transmit center frequency value that is equal to the receive center frequency value. In other embodiments, a configuration profile may specify a transmit center frequency value that is not equal to the receive center frequency value. For example, the receive center frequency value may be a multiple of the transmit frequency value (e.g., may be twice the transmit frequency value as the case may be in the context of harmonic imaging). In some embodiments, the transducers may be capable of harmonic imagining using various pressure within about 0.1 to 1 MPa (including any value within that range) over a range of about 5 to 15 cm. The pressure may induce a harmonic vibration in the tissue, and the receiver may receive the signal at the harmonic mode and/or filter out the fundamental frequency.

As another example, a first configuration profile for a first operating mode may specify a first polarity value and a second configuration profile for a second operating mode may specify a second polarity value different from the first receive center frequency value. In some embodiments, the polarity parameter may indicate whether to operate the pulsers (e.g., pulser 208) in the transmit chain in unipolar mode or in bipolar mode. Operating pulsers in bipolar mode may be advantageous as it results in lower second harmonic distortion for some tissues. On the other hand, operating pulsers in unipolar mode may provide for greater transducer acoustic power for certain bias voltages.

As another example, a first configuration profile for a first operating mode may specify a first ADC clock rate value (e.g., the clock rate at which to operate one or more analog-to-digital converters on the ultrasound device) and a second configuration profile for a second operating mode may specify a second ADC clock rate value different from the first ADC clock rate value. The ADC clock rate value may be used to set the rate at which to operate one or more ADCs in the receive circuitry of the ultrasound probe (e.g., ADC 212 part of receive circuitry 106 shown in FIG. 2).

As another example, a first configuration profile for a first operating mode may specify a first decimation rate value and a second configuration profile for a second operating mode may specify a second decimation rate value different from the first decimation rate value. In some embodiments, the decimation rate value may be used to set the rate of decimation performed by one or more components in the receive circuitry of the ultrasound probe. The decimation rate value and the ADC clock rate value together determine the bandwidth of the receiver in an operating mode, which bandwidth in turn defines the axial resolution of the operating mode. In addition, the ratio of the ADC rate and the decimation rate provides the effective sampling rate of the receiver in the operating mode.

As another example, a first configuration profile for a first operating mode may specify a first receive duration value and a second configuration profile for a second operating mode may specify a second receive duration value different from the first receive duration value. The receive duration value indicates a length of time over which a receiver acquires samples.

In some embodiments, an ultrasound probe may be configured to operate in an operating mode for cardiac imaging, an operating mode for abdominal imaging, an operating model for kidney imaging, an operating mode for liver imaging, an operating mode for ocular imaging, an operating mode for imaging the carotid artery, an operating mode for imaging the interior vena cava, and/or an operating mode for small parts imaging. In some embodiments, an ultrasound probe may be configured to operate in at least some (e.g., at least two, at least three, at least five, all) of these operating modes such that a user may use a single ultrasound probe to perform multiple different types of imaging. This allows a single ultrasound probe to perform imaging tasks that, conventionally, could be accomplished by using only multiple different ultrasound probes.

Figure 12B:
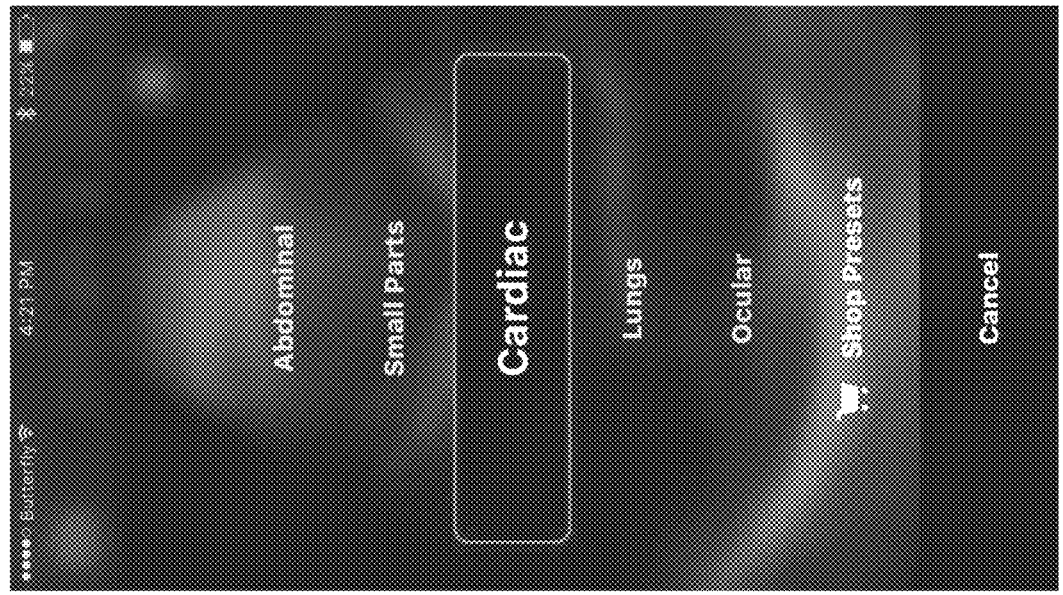
FIGS. 12A-B illustrate additional examples of a graphical user interface through which a user may select an operating mode in which to operate a universal ultrasound device, in accordance with some embodiments of the technology described herein.
Figure 12A:
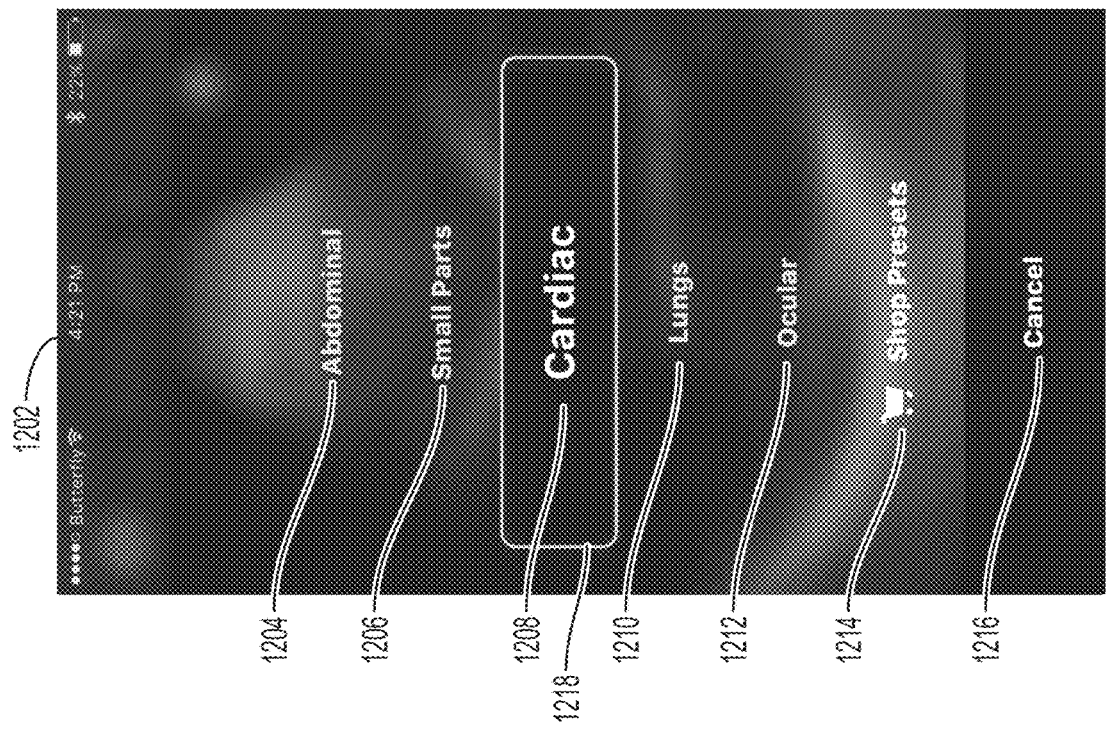

In some embodiments, a user may select an operating mode for an ultrasound probe through a graphical user interface presented by a mobile computing device (e.g., a smartphone) coupled to the ultrasound probe (via a wired or a wireless connection). For example, the graphical user interface may present the user with a menu of operating modes (e.g., as shown in FIGS. 12A and 12B) and the user may select (e.g., by tapping on a touchscreen, clicking with a mouse, etc.) one of the operating modes in the graphical user interface. In turn, the mobile computing device may provide an indication of the selected operating mode to the ultrasound device. The ultrasound device may obtain a configuration profile associated with the selected operating mode (e.g., by accessing it in a memory on the ultrasound device or receiving it from the mobile computing device) and use the parameter values specified therein to operate in the selected operating mode.

In some embodiments, the ultrasound device may provide, to the mobile computing device, data obtained through operation in a particular operating mode. The mobile computing device may process the received data to generate one or more ultrasound images and may present the generated ultrasound image(s) to the user through the display of the mobile computing device.

In some embodiments, the plurality of ultrasonic transducers includes a plurality of metal oxide semiconductor (MOS) ultrasonic transducers (e.g., CMOS ultrasonic transducers). In some embodiments, a MOS ultrasonic transducer may include a cavity formed in a MOS wafer, with a membrane overlying and sealing the cavity. In some embodiments, the plurality of ultrasonic transducers includes a plurality of micromachined ultrasonic transducers (e.g., capacitive micromachined ultrasonic transducers). In some embodiments, the plurality of ultrasonic transducers includes a plurality of piezoelectric ultrasonic transducers.

In some embodiments, a selection of an operating mode may be provided to a handheld ultrasound probe through a mobile computing device coupled (e.g., via a wired connection) to the ultrasound probe. In other embodiments, the selection of an operating mode may be provided to the ultrasound probe directly. For example, the ultrasound probe may comprise a mechanical control mechanism (e.g., a switch, a button, a wheel, etc.) for selecting an operating mode. As another example, the ultrasound probe may comprise a display (e.g., as shown in FIGS. 6A-B) and use the display to present a GUI to a user through which the user may select an operating mode for the ultrasound probe.

Figure 9:
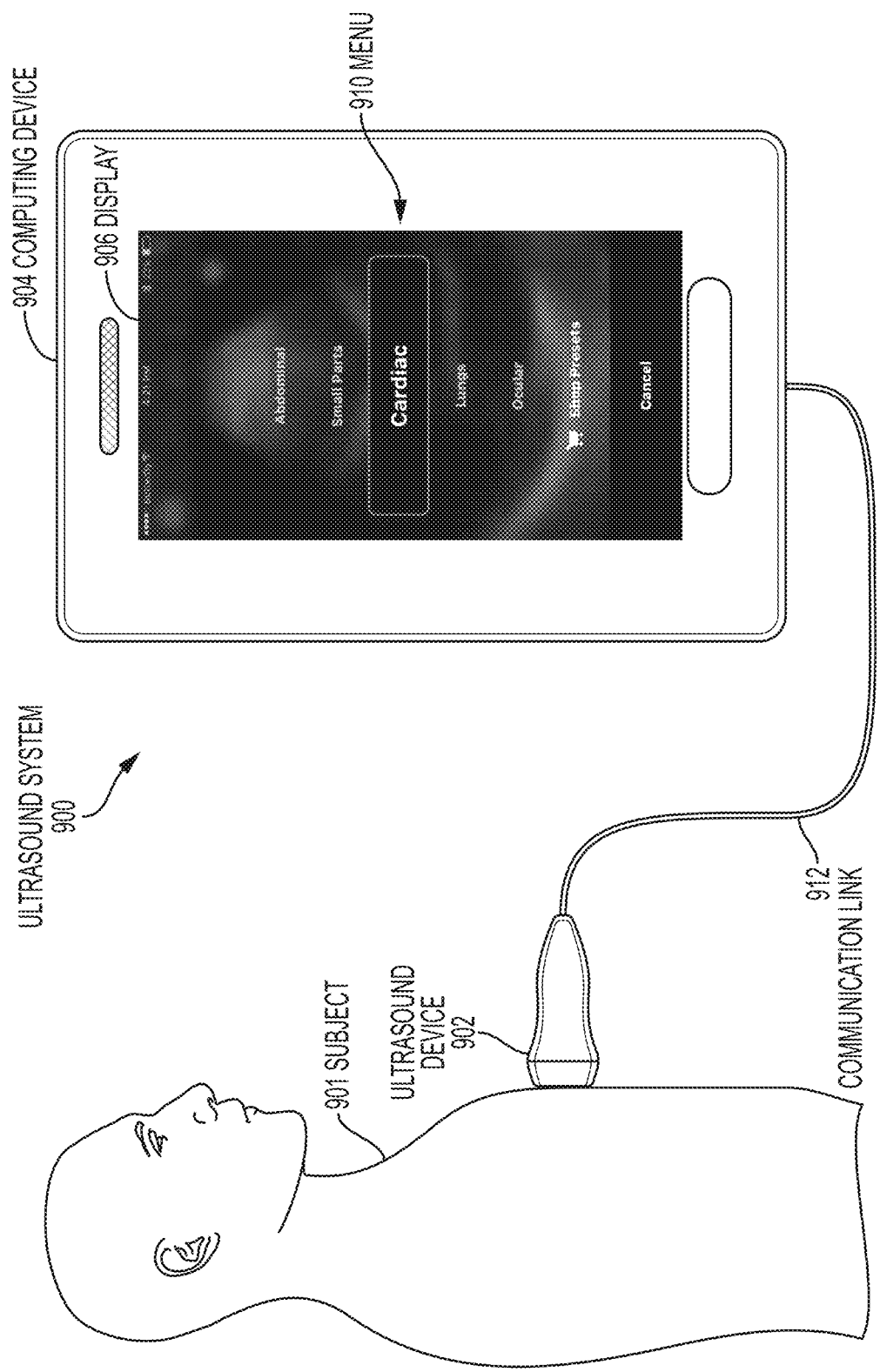
FIG. 9 is another diagram illustrating how a universal ultrasound device may be used to image a subject, in accordance with some embodiments of the technology described herein.

FIG. 9 is a diagram illustrating how a universal ultrasound device may be used to image a subject, in accordance with some embodiments of the technology described herein. In particular, FIG. 9 shows an illustrative ultrasound system 900 comprising an ultrasound device 902 communicatively coupled to computing device 904 via communication link 912. The ultrasound device 902 may be used to image subject 901 in any of a plurality of operating modes, examples of which are provided herein.

In some embodiments, the operating mode in which to operate ultrasound device 902 may be selected by a user of computing device 904. For example, in the illustrated embodiment, computing device 904 comprises a display 906 and is configured to present, via display 906, a graphical user interface comprising a menu 910 of different operating modes (further examples are shown in FIGS. 12A-B). The graphical user interface may comprise a GUI element (e.g., an icon, an image, text, etc.) for each of the operating modes that may be selected. A user may select one of the displayed menu options by tapping the screen of the computing device (when the display comprises a touch screen, using a mouse, a keyboard, voice input, or in any other suitable way. After receiving the user's selection, the computing device 904 may provide an indication of the selected operating mode to the ultrasound device 902 via communication link 912.

In some embodiments, responsive to receiving an indication of a selected operating mode from computing device 904, ultrasound device 902 may access a configuration profile associated with the operating mode. The configuration profile may specify values of one or more parameters, which are to be used for configuring the ultrasound probe to function in the selected operating mode. Examples of such parameter values are provided herein.

Figure 13:
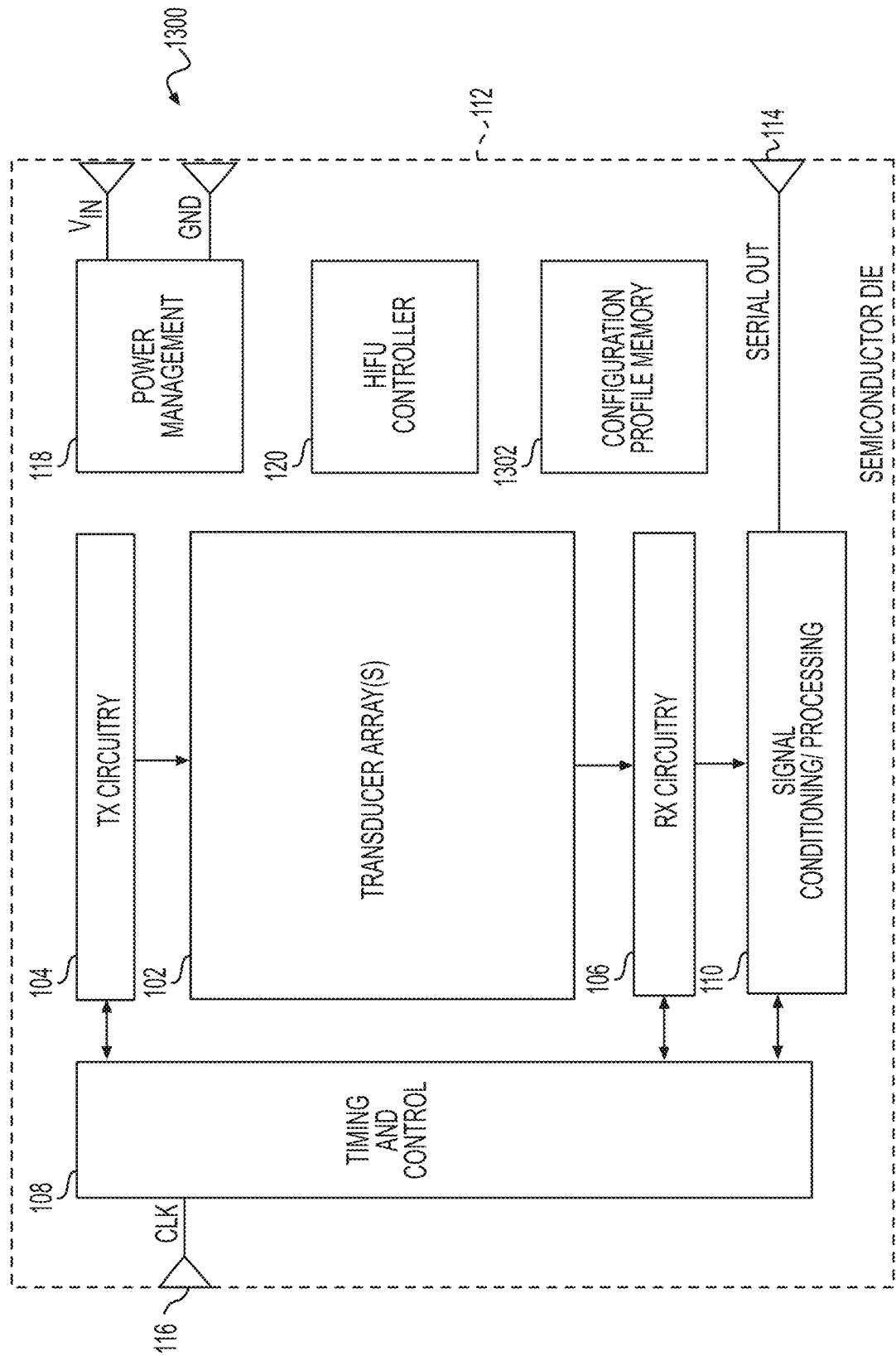
FIG. 13 is a block diagram of another illustrative example of a universal ultrasound device, in accordance with some embodiments of the technology described herein.

In some embodiments, the configuration profile for the selected mode may be stored onboard ultrasound probe 902 (e.g., in the configuration profile memory 1302 shown in FIG. 13). In other embodiments, the configuration profile for the selected mode may be provided, via communication link 912, to the ultrasound probe from the computing device 904. In yet other embodiments, one or more of the parameter values of a configuration mode may be stored onboard the ultrasound probe and one or more other parameter values of the configuration mode may be provided, via communication link 912, to the ultrasound probe from the computing device 904.

Figure 14:
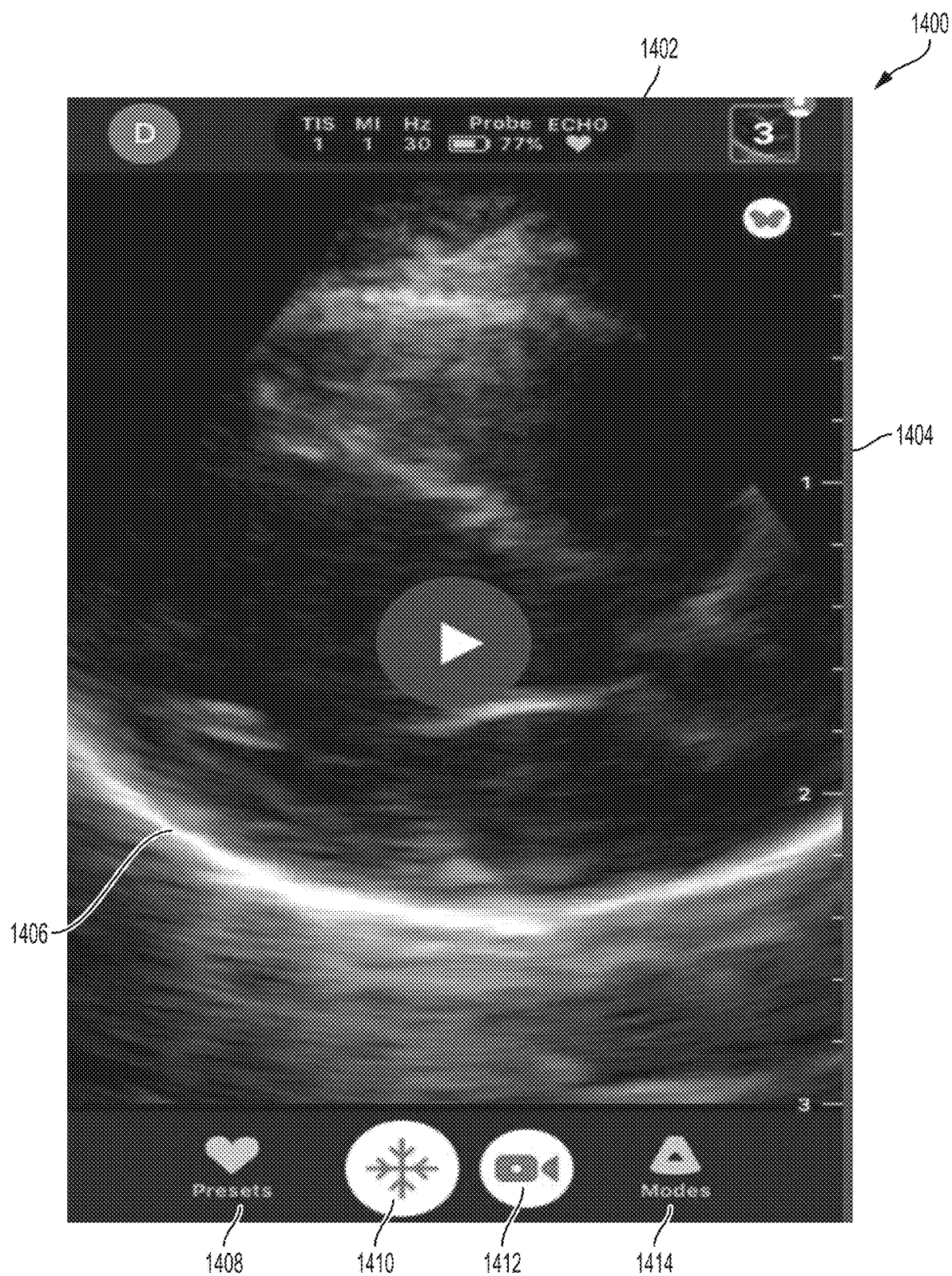
FIG. 14 illustrates another example of a graphical user interface through which a user may interact with a universal ultrasound device, in accordance with some embodiments of the technology described herein.

In some embodiments, data obtained by the ultrasound device 902 during operation in a particular operating mode may be provided, via communication link 912, to computing device 904. The computing device 904 may process the received data to generate one or more ultrasound images and display the generated ultrasound image(s) via display 906 (e.g., as shown in FIG. 14).

In some embodiments, ultrasound probe 902 may be a handheld ultrasound probe of any suitable type described herein including, for example, the ultrasound probe illustrated in FIG. 8. In some embodiments, the handheld ultrasound probe may comprise a display and, for example, may be an ultrasound probe of the kind illustrated in FIGS. 6A-6B (in such embodiments, some or all of the functionality performed by the computing device 904 may be performed onboard the ultrasound probe). In other embodiments, ultrasound probe 902 may be a wearable ultrasound probe and, for example, may be a skin-mountable ultrasound patch such as the patch illustrated in FIGS. 7A-7D.

FIG. 13 shows a block diagram of ultrasound device 902, in some embodiments. As shown in FIG. 13, ultrasound device 902 may include components shown and described with reference to FIG. 1B including, one or more transducer arrangements (e.g., arrays) 102, transmit (TX) circuitry 104, receive (RX) circuitry 106, a timing & control circuit 108, a signal conditioning/processing circuit 110, a power management circuit 118, and/or a high-intensity focused ultrasound (HIFU) controller 120. In the embodiment shown, all of the illustrated elements are formed on a single semiconductor die 112. It should be appreciated, however, that in alternative embodiments one or more of the illustrated elements may be instead located off-chip.

Additionally, as shown in the embodiment of FIG. 13, ultrasound device 902 may comprise a configuration profile memory 1302, which may store one or more configuration profiles for a respective one or more operating modes. For example, in some embodiments, configuration profile memory 1302 may store parameter values for each of one or more configuration profiles. In some embodiments, control circuitry (e.g., circuitry 108) may be configured to access, in the configuration profile memory 1302, parameter values for a selected configuration profile and configure one or more other components of the ultrasound probe (e.g., transmit circuitry, receive circuitry, ultrasound transducers, etc.) to operate in accordance with the accessed parameter values.

In some embodiments, computing device 904 may be a portable device. For example, computing device 904 may be a mobile phone, a smartphone, a tablet computer, or a laptop. The computing device 904 may comprise a display, which may be of any suitable type, and/or may be communicatively coupled to a display external to the computing device 904. In other embodiments, the computing device 904 may be a fixed device (e.g., a desktop computer, a rackmount computer, etc.).

In some embodiments, communication link 912 may be a wired link. In other embodiments, communication link 912 may be a wireless link (e.g., a Bluetooth or Wi-Fi connection).

Figure 10:
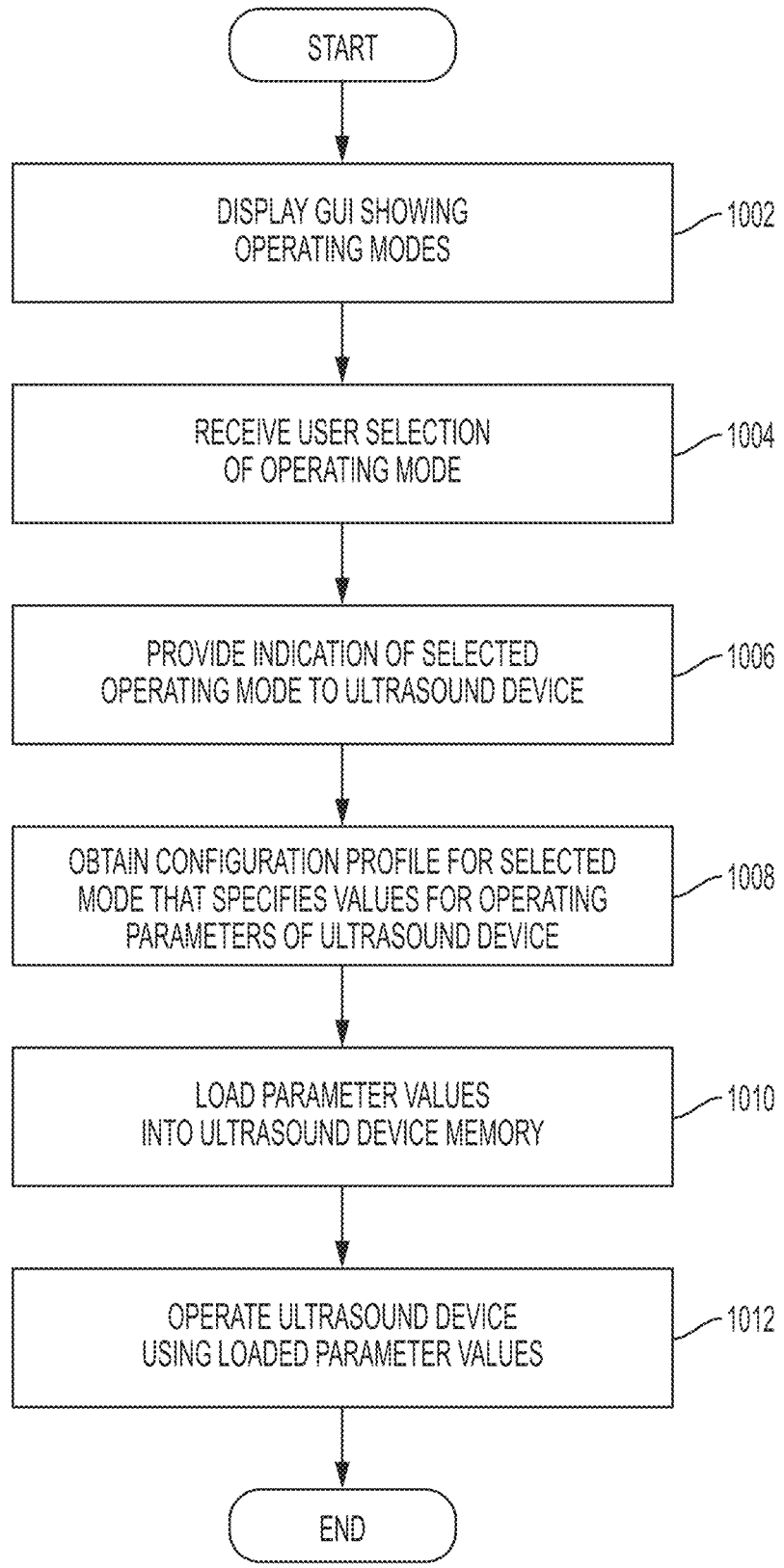
FIG. 10 is a flowchart of an illustrative process for operating a universal ultrasound device, in accordance with some embodiments of the technology described herein.

FIG. 10 is a flowchart of an illustrative process 1000 for operating a universal ultrasound device, in accordance with some embodiments of the technology described herein. Illustrative process 1000 may be performed by any suitable device(s) and, for example, may be performed by ultrasound device 902 and computing device 904 described with reference to FIG. 9. As another example, in some embodiments, an ultrasound device may perform all acts of process 1000.

Process 1002 begins at act 1002, where a graphical user interface (GUI) showing multiple operating modes is shown on a display. The display may be part of a computing device communicatively coupled to an ultrasound probe (e.g., the display a mobile smartphone). The GUI may include a GUI element (e.g., an icon, an image, a text portion, a menu item, etc.) for each of the multiple operating modes. In some embodiments, each GUI element representing an operating may be selectable by a user, for example, through tapping with a finger or stylus (when the display is a touchscreen) and/or clicking. Additionally or alternatively, a GUI element may be selected through keyboard input and/or voice input, as aspects of the technology described herein are not limited in this respect.

In some embodiments, the GUI may be generated by an application program executing on the computing device. For example, the GUI may be generated by application program "app" executing on a mobile smartphone. The application program may be configured to not only generate and display the GUI, but also receive a user's selection of the operating mode at act 1004 and provide an indication of the user's selection to the ultrasound device at act 1006. Additionally, in some embodiments, the application program may be configured to receive data gathered by the ultrasound device, generate one or more ultrasound images using the data, and display the generated ultrasound image(s) using the display of the mobile computing device. In other embodiments, the application program may receive ultrasound image(s) generated onboard an ultrasound device (rather than generating the ultrasound image(s) itself) and display them.

Figure 11:
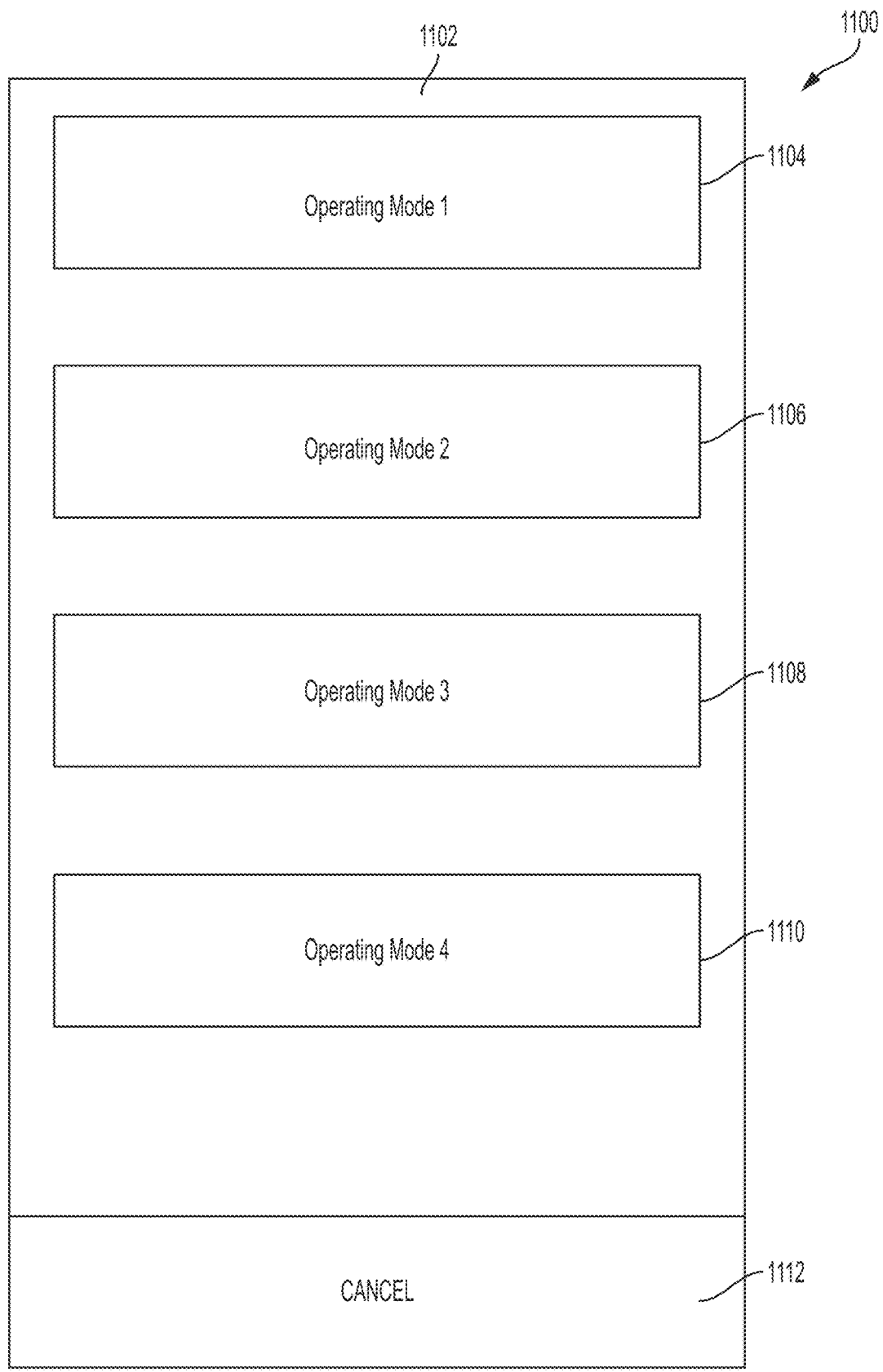
FIG. 11 illustrates an example of a graphical user interface through which a user may select an operating mode in which to operate a universal ultrasound device, in accordance with some embodiments of the technology described herein.

FIG. 11 shows an example GUI 1100 that may be displayed as part of act 1002. The GUI 1100 comprises a first portion 1102 containing GUI elements 1104, 1106, 1108, and 1110 representing different operating modes. Although the GUI 1100 shows a menu of four operating modes, this is merely for illustration and not by way of limitation, as a GUI may show any suitable number of operating modes. Furthermore, in some embodiments, a GUI may show some of the operating modes and allow the user to reveal additional operating modes, for example, by scrolling or navigating the GUI in any other suitable way. The illustrative GUI 1100 also comprises a second portion 1112 showing a GUI element corresponding to the "Cancel" option, which allows a user to not select any of the operating modes shown in first portion 1102.

FIG. 12A shows another example GUI 1202 that may be displayed as part of act 1002. The GUI 1202 comprises multiple selectable GUI elements corresponding to respective operating modes including GUI elements 1204, 1206, 1208, 1210, and 1212 corresponding, respectively, to operating modes for performing abdominal imaging, small parts imaging, cardiac imaging, lung imaging, and ocular imaging. The "Shop Presets" GUI element 1214 allows a user to download (e.g., through a purchase) one or more configuration profiles for additional operating mode(s). After the additional configuration profiles are downloaded, they may be used to control the ultrasound device to operate in the additional operating mode(s). GUI 1202 also includes a GUI element 1216 corresponding to the "Cancel" option, which may allow a user to not select any of the operating modes shown in GUI 1202.

Additionally, as shown in FIG. 12A, GUI 1202 includes an operating mode indicator 1218, which indicates a highlighted operating mode. As the user scrolls through different operating modes (e.g., by swiping along a touch screen, scrolling using a mouse or keyboard, etc.) different operating modes may be highlighted by operating mode indicator 1218. A user may select a highlighted operating mode (e.g., by tapping, clicking, etc.). In response, the GUI may provide the user with a visual confirmation of his/her selection. For example, as shown in FIG. 12B, after a user selects the cardiac operating mode, the GUI provides a visual confirmation of the user's selection by changing the color of the operating mode indicator. It should be appreciated that an operating mode indicator need not be implemented through a colored box or other shape surrounding text identifying the mode. For example, in some embodiments, an operating mode indicator may be provided by underlining text, changing text size, changing font size, italicizing text, and/or in any other suitable way. While in some embodiments the operating mode indicator may be visual, in yet other embodiments, the operating mode indicator may be provided as an audio indicator (e.g., through playback of recorded or synthesized speech indicating the operating mode). Similarly, a visual confirmation of a selection may be provided to the user in any suitable way and, in some embodiments, an audio confirmation may be provided in addition to or instead of the visual confirmation.

After the GUI is displayed at act 1002, process 1000 proceeds to act 1004 where a user's selection of the operating mode is received (e.g., by computing device 904), as a result of the user selecting one of the operating modes. As discussed, the user may select one of the operating modes through the GUI by using a touchscreen, mouse, keyboard, voice input, and/or any other suitable way. The GUI may provide the user with a visual confirmation of the selection.

Next, process 1000 proceeds to act 1006, where an indication of the selected operating mode is provided to the ultrasound device. For example, an indication of the selected operating mode may be provided by computing device 904 to ultrasound device 902. The indication may be provided in any suitable format, as aspects of the technology are not limited in this respect. In some embodiments, the indication may include at least a portion (e.g., all of) a configuration profile associated with the selected operating modes. For example, the indication may include one or more parameter values for the selected operating mode. In other embodiments, however, the indication may include information identifying the selected operating mode, but not include any of the parameter values for the mode, which parameter values may be stored onboard the ultrasound device.

Next, at act 1008, the ultrasound device obtains a configuration profile for the selected operating mode. In some embodiments, the configuration profile may be stored in at least one memory onboard the ultrasound device (e.g., configuration profile memory 1302 shown in FIG. 13). In other embodiments, at least some of the configuration profile (e.g., at least some of the parameter values) may be provided to the ultrasound probe from an external device (e.g., computing device 904 may transmit to ultrasound probe 902 at least some or all of the configuration profile for the selected operating mode).

Next, at act 1010, the parameter values in the obtained configuration profile may be used to configure the ultrasound device to operate in the selected mode. To this end, the parameter values may be used to configure one or more components of the ultrasound device and, to this end, may be loaded into one or more registers, memories, and the like, from which locations they may be utilized by ultrasound probe circuitry during operation in the selected operating mode.

Next, at act 1012, the ultrasound device may be operated in the selected operating mode using the parameter values specified in the configuration profile for the selected operating mode. For example, in some embodiments, control circuitry of an ultrasound device (e.g., control circuitry 108 shown in FIG. 13) may control one or more components of the ultrasound probe (e.g., waveform generator, programmable delay mesh circuitry, transmit circuitry, receive circuitry, etc.) using the parameter values specified in the configuration profile.

As described herein, data obtained by an ultrasound probe may be processed to generate an ultrasound image. In some embodiments, data obtained by an ultrasound probe may be provided to a computing device (e.g., computing device 904) and processed to generate one or more ultrasound images. In turn, the ultrasound image(s) may be presented to a user through a display of the computing device.

FIG. 14 shows an example of a graphical user interface 1400 configured to show one or more ultrasound images (e.g., a single ultrasound image, a series or movie of ultrasound images) to a user. In the example of FIG. 14, the GUI 1400 displays ultrasound images in image portion 1406. In addition to an ultrasound image, the GUI 1400 may include other components such as status bar 1402, scale 1404, and selectable options 1408, 1410, and 1412.

In some embodiments, the status bar 1402 may display information about the state of the ultrasound device such as, for example, the operating frequency and/or a battery life indicator. In some embodiments, the scale 1404 may show a scale for the image portion 1406. The scale 1404 may show a scale for the image portion 1406. The scale 1404 may correspond to depth, size, or any other suitable parameter for display with the image portion 1406. In some embodiments, the image portion 1406 may be displayed without the scale 1404.

In some embodiments, the selectable option 1408 may allow a user to access one or more preset operating modes, selected from one or more operating modes of the ultrasound device. The selectable option 1410 may allow the user to take a still image of the image portion 1406. The selectable option 1412 may allow the user to record a video of the image portion 1406. The selectable option 1414 may allow a user to access any or all of the operating modes of the ultrasound device. In some embodiments, any or all of the selectable options 1408, 1410, 1412, and 1414 may be displayed, while in other embodiments none of them may be displayed.

As described above, in some embodiments, an ultrasound probe may be operated in one of multiple operating modes each of which is associated with a respective configuration profile. A configuration profile for an operating mode may specify one or more parameter values used by the ultrasound probe to function in the operating mode. Tables 2-4 shown below illustrate parameter values in configuration profiles for a plurality of illustrative operating modes. The parameter values for a particular configuration profile are shown in a particular row across all three tables (a single table showing all the parameter values was split into three tables for ease of presentation, with the first two columns repeated in each table to simplify cross-referencing.) Accordingly, each row in Tables 2-4 specifies parameter values of a configuration profile for a particular operating mode. For example, parameter values for an operating mode for abdominal imaging may be found in the first row of Table 2, the first row of Table 3 and the first row of Table 4. As another example, parameter values for an operating mode for thyroid imaging may be found in the last row of Table 2, the last row of Table 3, and the last row of Table 4.

As may be appreciated from Tables 2-4, while some parameter values change across multiple modes, some parameter values may be the same in multiple modes, as not all parameter values for different modes differ from one another. However, one or more parameter values are different for any two given operating modes. It should be appreciated that the values shown in Tables 2-4 are examples of possible parameters. Any range of values suitable for the operating modes is possible; for example for any of the values listed, alternative values within +/−20% may be used.

Table 2 illustrates parameter values for multiple operating modes, including: (1) parameter values for the "TX Frequency (Hz)" parameter, which indicate transmit center frequency values and, in this example, are specified in Hertz; (2) parameter values for the "TX # cycles" parameter, which may indicate the number of transmit cycles used by the transducer array; (3) parameter values for the "TX Az. Focus (m)" parameter, which may indicate the azimuth focus values and, in this example, are specified in meters; (4) parameter values for the "TX El. Focus (m)" parameter, which may indicate elevation focus values and, in this example, are specified in meters; (5) parameter values for the "TX Az. F#" parameter, which may indicate the F numbers of the transmitter azimuth (and may be obtained by dividing the azimuth focus value by the azimuth aperture value); (6) parameter values for the "TX El. F#" parameter, which may indicate the F numbers of the transmitter elevation (and may be obtained by dividing the elevation focus value by the azimuth aperture value); and (7) parameter values for the "TX Az. Aperture (m)" parameter, which may indicate azimuth aperture values and, in this example, are specified in meters. In some embodiments the "TX Az. Aperture" parameter may have a range of 1.8-3.5 cm (e.g., 1.9-3.4 cm or 2.0-3.3 cm). Table 2 also includes a column for "TX El. Aperture (m)" which is duplicated in Table 3 for purposes of simplicity, and described further below in connection with Table 3.

TABLE 2

Illustrative parameter values for configuration profiles associated with different operating modes.

| Preset Name | TX Frequency (Hz) | TX # cycles | TX Az. Focus (m) | TX El. Focus (m) | TX Az. F# | TX El. F# | TX Az. Aperture (m) | TX El. Aperture (m) |
|---|---|---|---|---|---|---|---|---|
| abdomen | 3500000 | 1 | 0.1 | 0.07 | 4 | 5 | 0.025 | 0.013 |
| abdomen_thi | 1750000 | 1 | 0.1 | 0.07 | 4 | 5 | 0.025 | 0.013 |
| abdomen_vascular | 2800000 | 2 | 0.18 | INF | 2 | INF | 0.028 | 0.013 |
| abdomen_vascular_thi | 1600000 | 1 | 0.08 | INF | 2 | INF | 0.028 | 0.013 |
| cardiac | 2300000 | 2 | 0.14 | INF | 3 | INF | 0.028 | 0.013 |
| cardiac_thi | 1500000 | 2 | 0.06 | INF | 3 | INF | 0.020 | 0.013 |
| carotid | 8100000 | 2 | 0.045 | 0.06 | 4 | 18 | 0.011 | 0.003 |

TABLE 2-continued

Illustrative parameter values for configuration profiles associated with different operating modes.

| Preset Name | TX Frequency (Hz) | TX # cycles | TX Az. Focus (m) | TX El. Focus (m) | TX Az. F# | TX El. F# | TX Az. Aperture (m) | TX El. Aperture (m) |
| --- | --- | --- | --- | --- | --- | --- | --- | --- |
| carotid_flow | 4000000 | 4 | INF | 0.1 | 1 | 1 | 0.028 | 0.013 |
| interleave_cardiac_flow_bmode | 3000000 | 1 | INF | 0.09 | 2 | 2 | 0.028 | 0.013 |
| interleave_cardiac_flow_color | 2000000 | 4 | INF | 0.1 | 2 | 7.5 | 0.028 | 0.013 |
| interleave_carotid_flow_bmode | 7500000 | 2 | INF | 0.06 | 2 | 9 | 0.028 | 0.007 |
| interleave_carotid_flow_color | 4000000 | 4 | INF | 0.05 | 1 | 1 | 0.028 | 0.013 |
| joint | 7000000 | 1 | INF | 0.03 | 1 | 6.5 | 0.028 | 0.005 |
| joint_power | 4000000 | 4 | INF | 0.01 | 1 | 0.75 | 0.028 | 0.013 |
| m_mode | 4000000 | 1 | INF | 0.03 | 2 | 2 | 0.028 | 0.013 |
| msk | 6200000 | 2 | INF | 0.03 | 2 | 6.5 | 0.028 | 0.005 |
| msk_superficial | 8300000 | 1 | 0.02 | 0.02 | | | 0.005 | 0.004 |
| obstetric | 3500000 | 1 | 0.14 | 0.09 | 4 | 5 | 0.028 | 0.013 |
| patch_kidney | 3000000 | 2 | INF | 0.06 | 2 | 2 | 0.028 | 0.013 |
| thyroid | 7500000 | 2 | 0.045 | 0.035 | 4 | 2.5 | 0.011 | 0.013 |

Table 3 illustrates additional parameter values for the multiple operating modes, including: (1) parameter values for the "TX El. Aperture (m)" parameter, which may indicate elevation aperture values and, in this example, are specified in meters. In some embodiments the TX El. Aperture parameter may have a range of 1.5-2.5 cm (e.g., 1.75-2.25 cm); (2) parameter values for the "Bias Voltage (V)" parameter, which may indicate transducer bias voltage values and, in this example, are specified in Volts; (3) parameter values for the "TX Pk-Pk. Voltage (V)", which may indicate transmit peak-to-peak voltage values and, in this example, are specified in Volts; and (4) parameter values for the "Bipolar?" parameter, which may indicate to polarity values, which in this example are either unipolar or bipolar.

TABLE 3

Illustrative parameter values (for additional parameters) in the configuration profiles of Table 2.

| Preset Name | TX Frequency (Hz) | TX El. Aperture (m) | Bias Voltage (V) | TX Pk-Pk. Voltage (V) | Bipolar? |
| --- | --- | --- | --- | --- | --- |
| abdomen | 3500000 | 0.013 | 70 | 31 | TRUE |
| abdomen_thi | 1750000 | 0.013 | 70 | 38 | FALSE |
| abdomen_vascular | 2800000 | 0.013 | 60 | 40 | TRUE |
| abdomen_vascular_thi | 1600000 | 0.013 | 60 | 40 | TRUE |
| cardiac | 2300000 | 0.013 | 60 | 31 | TRUE |
| cardiac_thi | 1500000 | 0.013 | 60 | 40 | TRUE |
| carotid | 8100000 | 0.003 | 80 | 20 | TRUE |
| carotid_flow | 4000000 | 0.013 | 80 | 41 | TRUE |
| interleave_cardiac_flow_bmode | 3000000 | 0.013 | 48 | 31 | FALSE |
| interleave_cardiac_flow_color | 2000000 | 0.013 | 48 | 31 | FALSE |
| interleave_carotid_flow_bmode | 7500000 | 0.007 | 80 | 41 | TRUE |
| interleave_carotid_flow_color | 4000000 | 0.013 | 80 | 41 | TRUE |
| joint | 7000000 | 0.005 | 90 | 18 | FALSE |
| joint_power | 4000000 | 0.013 | 90 | 16 | FALSE |
| m_mode | 4000000 | 0.013 | 60 | 31 | FALSE |
| msk | 6200000 | 0.005 | 90 | 18 | FALSE |
| msk_superficial | 8300000 | 0.004 | 90 | 20 | TRUE |
| obstetric | 3500000 | 0.013 | 70 | 31 | TRUE |
| patch_kidney | 3000000 | 0.013 | 60 | 25 | FALSE |
| thyroid | 7500000 | 0.013 | 80 | 20 | TRUE |

Table 4 illustrates additional parameter values for the multiple operating modes, including: (1) parameter values for the "RX Frequency (Hz)" parameter, which may indicate receive center frequency values and, in this example, are specified in Hertz; (2) parameter values for the "ADC Rate (Hz)" parameter, which may indicate ADC clock rate values and, in this example, are specified in Hertz; (3) parameter values for the "Decimation Rate" parameter, which may indicate decimation rate values; (4) parameter values for the "Bandwidth (Hz)" parameter, which may indicate bandwidths of the receiver and, in this example, are specified in Hertz; (5) parameter values for the "Low (Hz)" parameter and for the "High (Hz)" parameter, which respectively indicate the low and high cutoffs of the operating frequency range and, in this example, are specified in Hertz; (6) parameter values for the "RX Depth (m)" parameter, which may be provided in meters; and (7) parameters values for the "RX Duration (us)" parameter, which may indicate receiver duration values and, in this example, are specified in microseconds.

As has been described, ultrasound devices (e.g., probes) according to aspects of the present application may be used in various modes with various associated frequency ranges and depths. Thus, ultrasound devices according to the various aspects herein may be used to generate differing ultrasound beams. To illustrate the point, various non-limiting examples are now described with respect to FIGS. 15-17. The ultrasound devices described herein may, in at least some embodiments, generate two or more ultrasound beam types (e.g., beam shapes) typically associated with linear, sector, curvilinear (convex), and mechanically scanned (moved) probes. In at least some embodiments, an ultrasound probe according to aspects of the present application may generate ultrasound beams typically associated with all of linear, sector, curvilinear, and mechanically scanned probes.

Figure 15:
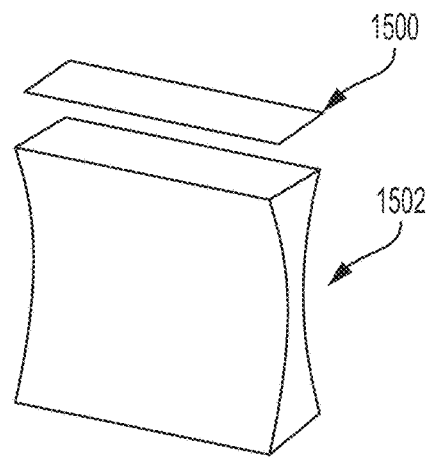
FIGS. 15-17 illustrate non-limiting examples of ultrasound beam shapes which may be generated with an ultrasound device of the types described herein, according to non-limiting embodiments.

FIG. 15 shows one example of a beam shape for an ultrasound probe according to a non-limiting embodiment of the present application. As illustrated in FIG. 15, the ultrasound probe may utilize a linear beam shape 1502 generated

TABLE 4

Illustrative parameter values (for more additional parameters) in the configuration profiles of Table 2.

| Preset Name | TX Frequency (Hz) | Rx Frequency (Hz) | ADC Rate (Hz) | Decimation Rate | Bandwidth (MHz) | Low (Hz) | High (Hz) | RX Depth (m) | RX Duration (us) |
|---|---|---|---|---|---|---|---|---|---|
| abdomen | 3500000 | 3500000 | 25000000 | 4 | 3125000 | 1937500 | 5062500 | 0.12 | 80.0 |
| abdomen_thi | 1750000 | 3500000 | 25000000 | 4 | 3125000 | 1937500 | 5062500 | 0.12 | 80.0 |
| abdomen_vascular | 2800000 | 2800000 | 25000000 | 6 | 2083333 | 1758333 | 3841667 | 0.15 | 100.0 |
| abdomen_vascular_thi | 1600000 | 3200000 | 25000000 | 6 | 2083333 | 2158333 | 4241667 | 0.15 | 100.0 |
| cardiac | 2300000 | 2300000 | 25000000 | 6 | 2083333 | 1258333 | 3341667 | 0.15 | 100.0 |
| cardiac_thi | 1500000 | 3000000 | 25000000 | 6 | 2083333 | 1958333 | 4041667 | 0.15 | 100.0 |
| carotid | 8100000 | 8100000 | 25000000 | 3 | 4166667 | 6016667 | 10183333 | 0.04 | 26.7 |
| carotid_flow | 4000000 | 4000000 | 25000000 | 8 | 1562500 | 3218750 | 4781250 | 0.04 | 26.7 |
| interleave_cardiac_flow_bmode | 3000000 | 3000000 | 25000000 | 16 | 781250 | 2609375 | 3390625 | 0.035 | 23.3 |
| interleave_cardiac_flow_color | 2000000 | 2000000 | 25000000 | 16 | 781250 | 1609375 | 2390625 | 0.035 | 23.3 |
| interleave_carotid_flow_bmode | 7500000 | 7500000 | 25000000 | 5 | 2500000 | 6250000 | 8750000 | 0.16 | 106.7 |
| interleave_carotid_flow_color | 4000000 | 4000000 | 25000000 | 9 | 1388889 | 3305556 | 4694444 | 0.16 | 106.7 |
| joint | 7000000 | 7000000 | 25000000 | 3 | 4166667 | 4916667 | 9083333 | 0.03 | 20.0 |
| joint_power | 4000000 | 4000000 | 25000000 | 5 | 2500000 | 2750000 | 5250000 | 0.025 | 16.7 |
| m_mode | 4000000 | 4000000 | 25000000 | 8 | 1562500 | 3218750 | 4781250 | 0.15 | 100.0 |
| msk | 6200000 | 6200000 | 25000000 | 3 | 4166667 | 4116667 | 8283333 | 0.04 | 26.7 |
| msk_superficial | 8300000 | 8300000 | 25000000 | 2 | 6250000 | 5175000 | 11425000 | 0.02 | 13.3 |
| obstetric | 3500000 | 3500000 | 25000000 | 4 | 3125000 | 1937500 | 5062500 | 0.15 | 100.0 |
| patch_kidney | 3000000 | 3000000 | 25000000 | 9 | 1388889 | 2305556 | 3694444 | 0.11 | 73.3 |
| thyroid | 7500000 | 7500000 | 25000000 | 4 | 3125000 | 5937500 | 9062500 | 0.04 | 26.7 |

As previously described, different resolutions may be achieved or provided with the different operating modes, in at least some embodiments. For example, the operating modes reflected in Tables 2-4 may provide axial resolutions ranging between 300 μm and 2,000 μm, including any value within that range, as well as other ranges. The same operating modes may provide lateral resolution at the focus between 200 μm and 5,000 μm, including any value within that range, as well as other ranges. The same operating modes may provide elevational resolution at the focus between 300 μm and 7,000 μm, including any value within that range, as well as other ranges. As a non-limiting example, the first "abdomen" mode may provide an axial resolution of approximately 400 μm, a lateral resolution at focus of approximately 2,000 μm, and an elevational resolution at focus of approximately 2,700 μm. By contrast, the "interleave_cardiac_flow_color" mode may provide an axial resolution of approximately 1,700 μm, a lateral resolution at focus of approximately 900 μm, and an elevational resolution at focus of approximately 7,000 μm. These represent non-limiting examples.

by the transducer array 1500. It should be appreciated that the beam shape 1502 may be based on accumulated azimuth transmit intensities over a spatial region. By acquiring multiple elevational transmit angles and/or focuses and coherently summing them, the azimuthal beam shape can effectively become a narrow slice. The depth of the waist of the beam shape 1502 may be fixed at a location that is appropriate based on the attenuation of the frequency being used. In some embodiments, a linear beam shape 1502 may be used at 3-7 MHz, 5-12 MHz, or 7-15 MHz. The linear beam shape 1502 may provide higher resolution and shallower imaging at increasing frequencies.

Figure 16:
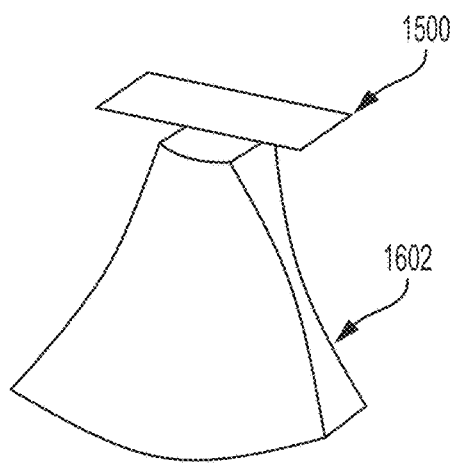

FIG. 16 shows another example of a beam shape for an ultrasound probe according to a non-limiting embodiment. As illustrated in FIG. 16, the ultrasound probe may utilize a sector beam shape 1602 generated by the transducer array 1500. It should be appreciated that the beam shape 1602 may be based on accumulated azimuth transmit intensities over a spatial region. In some embodiments, a sector beam shape 1602 may be used at 1-3 MHz, 2-5 MHz, or 3.6-10 MHz. These frequency ranges may be used for cardiac, abdominal, pelvic, or thoracic imaging, for example. In some embodiments, the sector beam shape 1602 may be suitable for deep tissue imaging.

Figure 17:
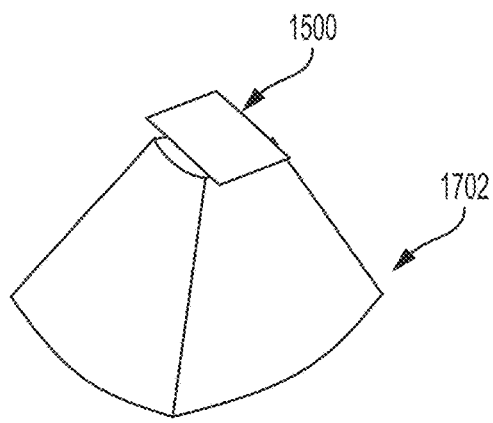

FIG. 17 shows another example of a beam shape for an ultrasound probe. As illustrated in FIG. 17, the ultrasound probe may utilize a 3D beam shape 1702 generated by the transducer array 1500. It should be appreciated that the beam shape 1502 may be based on accumulated azimuth transmit intensities over a spatial region. In some embodiments, a 3D beam shape 1702 may be used at 3.5-6.5 MHz or 7.5-11 MHz. In some embodiments the 3D beam shape 1702 may be a result of electronically scanning/sweeping either a sector or curvilinear profile, without mechanically scanning the probe. In some embodiments, the 3D beam shape 1702 may be suitable for 3D volume imaging.

According to at least some embodiments of the present application, an ultrasound probe may generate all the beam shapes shown in FIGS. 15-17, as well as potentially generating additional beam shapes. For example, transducer array 1500 may generate all the beam shapes shown in FIGS. 15A-15C. Moreover, as has been described herein, the various modes of operation, and the various associated beam shapes, may be generated with a substantially flat ultrasonic transducer array. Thus, in at least some embodiments, beam shapes typically associated with a curvilinear transducer array may instead be achieved with a substantially flat ultrasonic transducer arrangement.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The following non-limiting exemplary embodiments are provided to illustrate inventive aspects of the disclosure.

Example 1 is directed to an ultrasound device, comprising: an ultrasound probe, including: a semiconductor die, and a plurality of ultrasonic transducers integrated on the semiconductor die, the plurality of ultrasonic transducers configured to operate in a first mode associated with a first frequency range and a second mode associated with a second frequency range, wherein the first frequency range is at least partially non-overlapping with the second frequency range; and control circuitry configured to: control the plurality of ultrasonic transducers to generate and/or detect ultrasound signals having frequencies in the first frequency range, in response to receiving an indication to operate the ultrasound probe in the first mode; and control the plurality of ultrasonic transducers to generate and/or detect ultrasound signals having frequencies in the second frequency range, in response to receiving an indication to operate the ultrasound probe in the second mode.

Example 2 is directed to the ultrasound device of example 1, wherein a width of the first frequency range is at least 1 MHz and a width of the second frequency range is at least 1 MHz.

Example 3 is directed to the ultrasound device of example 1, wherein a difference between a first center frequency in the first frequency range and a second center frequency in the second frequency range is at least 1 MHz.

Example 4 is directed to the ultrasound device of example 3, wherein the difference is at least 2 MHz.

Example 5 is directed to the ultrasound device of example 4, wherein the difference is between about 6 MHz and about 9 MHz.

Example 6 is directed to the ultrasound device of example 1, wherein the first frequency range is contained entirely within a range of 1-5 MHz.

Example 7 is directed to the ultrasound device of example 6, wherein the first frequency range is contained entirely within a range of 2-4 MHz.

Example 8 is directed to the ultrasound device of example 1, wherein the second frequency range is contained entirely within a range of 5-9 MHz.

Example 9 is directed to the ultrasound device of example 8, wherein the second frequency range is contained entirely within a range of 6-8 MHz.

Example 10 is directed to the ultrasound device of example 1, the plurality of ultrasonic transducers is further configured to operate in a third mode associated with a third frequency range that is at least partially non-overlapping with the first frequency range and the second frequency range, and wherein the control circuitry is further configured to: control the plurality of ultrasonic transducers to generate and/or detect ultrasound signals having frequencies in the third frequency range, in response to receiving an indication to operate the ultrasound probe in the third mode.

Example 11 is directed to the ultrasound device of example 10, wherein the first frequency range is contained entirely within a range of 1-3 MHz, the second frequency range is contained entirely within a range of 3-7 MHz, and the third frequency range is contained entirely within a range of 7-15 MHz.

Example 12 is directed to the ultrasound device of example 1, wherein: when the plurality of ultrasonic transducers are controlled to detect ultrasound signals having frequencies in the first frequency range, ultrasound signals detected by the plurality of ultrasonic transducers are used to form an image of a subject up to a first depth within the subject; and when the plurality of ultrasonic transducers are controlled to detect ultrasound signals having frequencies in the second frequency range, ultrasound signals detected by the plurality of ultrasonic transducers are used to form an image of a subject up to a second depth within the subject, wherein the second depth is smaller than the first depth.

Example 13 is directed to the ultrasound device of example 12, wherein the first depth is contained within a range of up to 8-25 cm from a surface of the subject.

Example 14 is directed to the ultrasound device of example 13, wherein the first depth is contained within a range of up to 15-20 cm from the surface of the subject.

Example 15 is directed to the ultrasound device of example 12, wherein the second depth is contained within a range of up to 3-7 cm from a surface of the subject.

Example 16 is directed to the ultrasound device of example 1, wherein the plurality of ultrasound transducers are capacitive ultrasonic transducers, and wherein the control circuitry is configured to control the plurality of ultrasonic transducers to generate and/or detect ultrasound signals having frequencies in the second frequency range at least in part by causing the plurality of ultrasonic transducers to operate in a collapsed mode, in which at least one portion of a membrane of the plurality of ultrasonic transducers is mechanically fixed and at least one portion of the membrane is free to vibrate based on a changing voltage differential between an electrode and the membrane.

Example 17 is directed to the ultrasound device of example 1, wherein the control circuitry is configured to: cause a first voltage to be applied to the plurality of ultrasonic transducers in response to the indication to operate the ultrasound probe in the first frequency range; and cause a second voltage to be applied to the plurality of ultrasonic transducers in response to the indication to operate the ultrasound probe in the second frequency range, wherein the second voltage is higher than the first voltage.

Example 18 is directed to the ultrasound device of example 17, wherein the second voltage is greater than a collapse voltage for the plurality of ultrasonic transducers, the collapse voltage comprising a voltage which causes a membrane of an ultrasonic transducers to make contact to a bottom of a cavity of the ultrasonic transducer.

Example 19 is directed to the ultrasound device of example 18, wherein the collapse voltage is at least 30 Volts.

Example 20 is directed to the ultrasound device of example 1, wherein the plurality of ultrasonic transducers includes multiple ultrasonic transducers at least one of which is configured to generate ultrasound signals in the first frequency range and in the second frequency range.

Example 21 is directed to the ultrasound device of example 1, wherein the plurality of ultrasonic transducers includes a plurality of CMOS ultrasonic transducers.

Example 22 is directed to the ultrasound device of example 21, wherein the plurality of CMOS ultrasonic transducers includes a first CMOS ultrasonic transducer including a cavity formed in a CMOS wafer, with a membrane overlying and sealing the cavity.

Example 23 is directed to the ultrasound device of example 1, wherein the plurality of ultrasonic transducers includes a plurality of micromachined ultrasonic transducers.

Example 24 is directed to the ultrasound device of example 23, wherein the plurality of micromachined ultrasonic transducers includes a plurality of capacitive micromachined ultrasonic transducers.

Example 25 is directed to the ultrasound device of example 23, wherein the plurality of micromachined ultrasonic transducers includes a plurality of piezoelectric ultrasonic transducers.

Example 26 is directed to the ultrasound device of example 1, wherein the ultrasound probe further comprises a handheld device.

Example 27 is directed to the ultrasound device of example 26, wherein the handheld device further comprises a display.

Example 28 is directed to the ultrasound device of example 26, wherein the handheld device further comprises a touchscreen.

Example 29 is directed to the ultrasound device of example 1, wherein the ultrasound probe comprises a patch configured to be affixed to a subject.

Example 30 is directed to a skin-mountable ultrasound patch, comprising: a monolithic ultrasound chip including a semiconductor die, and a plurality of ultrasonic transducers integrated on the semiconductor die, at least one of the plurality of ultrasonic transducers configured to operate in a first mode associated with a first frequency range and a second mode associated with a second frequency range, wherein the first frequency range is at least partially non-overlapping with the second frequency range; and a dressing configured to receive and retain the ultrasound chip, the dressing further configured to couple to a patient's body.

Example 31 is directed to the ultrasound patch of example 30, wherein the monolithic ultrasound chip further comprises a control circuitry configured to control the plurality of ultrasonic transducers to generate and/or detect ultrasound signals having frequencies in the first frequency range, in response to receiving an indication to operate the ultrasound probe in the first mode; and to control the plurality of ultrasonic transducers to generate and/or detect ultrasound signals having frequencies in the second frequency range, in response to receiving an indication to operate the ultrasound probe in the second mode.

Example 32 is directed to the ultrasound patch of example 31, wherein the control circuitry defines a CMOS circuitry.

Example 33 is directed to the ultrasound patch of example 30, wherein the dressing further comprises an adhesive layer to couple the patch to the patient's body.

Example 34 is directed to the ultrasound patch of example 30, further comprising a housing to receive the monolithic ultrasound chip, the housing having an upper portion and a lower portion, wherein the lower housing portion further comprises an aperture to expose the ultrasonic transducers to the subject's body.

Example 35 is directed to the ultrasound patch of example 30, further comprising a communication platform to communicate ultrasound signals to and from the ultrasound chip.

Example 36 is directed to the ultrasound patch of example 30, further comprising a circuit board to receive the ultrasound chip.

Example 37 is directed to the ultrasound patch of example 30, further comprising a communication platform to communicate with an external communication device.

Example 38 is directed to the ultrasound patch of example 37, wherein the communication platform is selected from the group consisting of Near-Field Communication (NFC), Bluetooth (BT), Bluetooth Low Energy (BLE) and Wi-Fi.

Example 39 is directed to a wearable ultrasound device, comprising: a ultrasound chip including an array of ultrasonic transducers, each ultrasonic transducer defining a capacitive micro-machined ultrasonic transducer (CMUT) operable to transceive signals; and a dressing configured to receive and retain the ultrasound chip, the dressing further configured to couple to a subject body; wherein the array of ultrasonic transducers further comprises a first plurality of CMUTs configured to operate in a collapse mode and a second plurality of CMUTs configured to operation in a non-collapse mode.

Example 40 is directed to the wearable ultrasound device of example 39, wherein the ultrasound chip further comprises a control circuitry configured to control the plurality of ultrasonic transducers to generate and/or detect ultrasound signals having frequencies in the first frequency range, in response to receiving an indication to operate the ultrasound probe in the first mode; and to control the plurality of ultrasonic transducers to generate and/or detect ultrasound signals having frequencies in the second frequency range, in response to receiving an indication to operate the ultrasound probe in the second mode.

Example 41 is directed to the wearable ultrasound device of example 40, wherein the ultrasound chip defines a solid-state device.

Example 42 is directed to the wearable ultrasound device of example 39, wherein the ultrasonic transducer is configured to generate a first frequency band when operated at collapse mode and to generate a second frequency band when operated at non-collapse mode.

Example 43 is directed to the wearable ultrasound device of example 39, wherein the ultrasound chip is configured to switch between collapse and non-collapse modes of operation.

Example 44 is directed to the wearable ultrasound device of example 39, further comprising a communication platform to communicate with an external communication device.

Example 45 is directed to the wearable ultrasound device of example 44, wherein the communication platform is selected from the group consisting of Near-Field Communication (NFC), Bluetooth (BT), Bluetooth Low Energy (BLE) and Wi-Fi.

Example 46 is directed to the wearable ultra-sound device of example 45, wherein the communication platform receives imaging instructions from an auxiliary device and transmits one or more ultrasound images to the auxiliary device in response to the received instructions.

Example 47 is directed to the wearable ultrasound device of example 39, wherein the dressing further comprises an opening to accommodate an optical lens adjacent the array of ultrasonic transducers.

According to some aspects of the present application, a system is provided, comprising: a multi-modal ultrasound probe configured to operate in a plurality of operating modes associated with a respective plurality of configuration profiles; and a computing device coupled to the multi-modal ultrasound probe and configured to, in response to receiving input indicating an operating mode selected by a user, cause the multi-modal ultrasound probe to operate in the selected operating mode.

In some embodiments, the plurality of operating modes includes a first operating mode associated with a first configuration profile specifying a first set of parameter values and a second operating mode associated with a second configuration profile specifying a second set of parameter values different from the first set of parameter values.

In some such embodiments, the computing device causes the multi-modal ultrasound probe to operate in a selected operating mode by providing an indication of the selected operating mode to the multi-modal ultrasound probe.

In some such embodiments, the multi-modal ultrasound probe comprises a plurality of ultrasonic transducers and control circuitry configured to: responsive to receiving an indication of the first operating mode from the computing device, obtain a first configuration profile specifying a first set of parameter values associated with the first operating mode; and control, using the first configuration profile, the ultrasound device to operate in the first operating mode, and responsive to receiving an indication of the second operating mode from the computing device, obtain a second configuration profile specifying a second set of parameter values associated with the second operating mode, the second set of parameter values being different from the first set of parameter values; and control, using the second configuration profile, the ultrasound device to operate in the second operating mode.

In some such embodiments, the first set of parameter values specifies a first azimuth aperture value and the second set of parameter values specifies a second azimuth aperture value different from the first azimuth aperture value, and the control circuitry is configured to control the plurality of ultrasonic transducers to operate in the first operating mode at least in part by using the first azimuth aperture value and to operate in the second operating mode at least in part by using the second azimuth aperture value.

In some such embodiments, the first set of parameter values specifies a first elevation aperture value and the second set of parameter values specifies a second elevation aperture value different from the first elevation aperture value, and the control circuitry is configured to control the plurality of ultrasonic transducers to operate in the first operating mode at least in part by using the first elevation aperture value and to operate in the second operating mode at least in part by using the second elevation aperture value.

In some such embodiments, the first set of parameter values specifies a first azimuth focus value and the second set of parameter values specifies a second azimuth focus value different from the first azimuth focus value, and the control circuitry is configured to control the plurality of ultrasonic transducers to operate in the first operating mode at least in part by using the first azimuth focus value and to operate in the second operating mode at least in part by using the second azimuth focus value.

In some such embodiments, the first set of parameter values specifies a first elevation focus value and the second set of parameter values specifies a second elevation focus value different from the first elevation focus value, and the control circuitry is configured to control the plurality of ultrasonic transducers to operate in the first operating mode at least in part by using the first elevation focus value and to operate in the second operating mode at least in part by using the second elevation focus value.

In some such embodiments, the first set of parameter values specifies a first bias voltage value for at least one of the plurality of ultrasonic transducers and the second set of parameter values specifies a second bias voltage value for the at least one of the plurality of ultrasonic transducers, the second bias voltage value being different from the first bias voltage focus value, and the control circuitry is configured to control the plurality of ultrasonic transducers to operate in the first operating mode at least in part by using the first bias voltage value and to operate in the second operating mode at least in part by using the second bias voltage value.

In some such embodiments, the first set of parameter values specifies a first transmit peak-to-peak voltage value and the second set of parameter values specifies a second transmit peak-to-peak voltage value different from the first transmit peak-to-peak voltage focus value, and the control circuitry is configured to control the plurality of ultrasonic transducers to operate in the first operating mode at least in part by using the first transmit peak-to-peak voltage value and to operate in the second operating mode at least in part by using the second transmit peak-to-peak voltage value.

In some such embodiments, the first set of parameter values specifies a first transmit center frequency value and the second set of parameter values specifies a second transmit center frequency value different from the first transmit center frequency value, and the control circuitry is configured to control the plurality of ultrasonic transducers to operate in the first operating mode at least in part by using the first transmit center frequency value and to operate in the second operating mode at least in part by using the second transmit center frequency value.

In some such embodiments, the first set of parameter values specifies a first receive center frequency value and the second set of parameter values specifies a second receive center frequency value different from the first receive center frequency value, and the control circuitry is configured to control the plurality of ultrasonic transducers to operate in the first operating mode at least in part by using the first receive center frequency value and to operate in the second operating mode at least in part by using the second receive center frequency value.

In some such embodiments, the first set of parameter values specifies a first polarity value and the second set of parameter values specifies a second polarity value different from the first polarity value, and the control circuitry is configured to control the plurality of ultrasonic transducers to operate in the first operating mode at least in part by using the first polarity value and to operate in the second operating mode at least in part by using the second polarity value.

In some such embodiments, the hand-held ultrasound probe further comprises an analog-to-digital converter (ADC), the first set of parameter values specifies a first ADC clock rate value and the second set of parameter values specifies a second ADC clock rate value different from the first ADC clock rate value, and the control circuitry is configured to control the plurality of ultrasonic transducers to operate in the first operating mode at least in part by operating the ADC at the first ADC clock rate value and to operate in the second operating mode at least in part by operating the ADC at the second ADC clock rate value.

In some such embodiments, the first set of parameter values specifies a first decimation rate value and the second set of parameter values specifies a second decimation rate value different from the first decimation rate value, and the control circuitry is configured to control the plurality of ultrasonic transducers to operate in the first operating mode at least in part by using the first decimation rate value and to operate in the second operating mode at least in part by using the second decimation rate value.

In some such embodiments, the first set of parameter values specifies a first receive duration value and the second set of parameter values specifies a second receive value different from the first receive duration value, and the control circuitry is configured to control the plurality of ultrasonic transducers to operate in the first operating mode at least in part by using the first receive duration value and to operate in the second operating mode at least in part by using the second receive duration value.

In some embodiments, the multi-modal ultrasound probe is a hand-held ultrasound probe.

In some embodiments, the computing device is a mobile computing device.

According to some aspects of the present application a method is provided for controlling operation of a multi-modal ultrasound probe configured to operate in a plurality of operating modes associated with a respective plurality of configuration profiles, the method comprising: receiving, at a computing device, input indicating an operating mode selected by a user; and causing the multi-modal ultrasound probe to operate in the selected operating mode using parameter values specified by a configuration profile associated with the selected operating mode.

According to some aspects of the present application a system is provided, comprising: an ultrasound device, comprising: a plurality of ultrasonic transducers, and control circuitry; and a computing device having at least one computer hardware processor and at least one memory, the computing device communicatively coupled to a display and to the ultrasound device, the at least one computer hardware processor configured to: present, via the display, a graphical user interface (GUI) showing a plurality of GUI elements representing a respective plurality of operating modes for the ultrasound device, the plurality of operating modes comprising first and second operating modes; responsive to receiving, via the GUI, input indicating selection of either the first operating mode or the second operating mode, provide an indication of the selected operating mode to the ultrasound device, wherein the control circuitry is configured to: responsive to receiving an indication of the first operating mode, obtain a first configuration profile specifying a first set of parameter values associated with the first operating mode; and control, using the first configuration profile, the ultrasound device to operate in the first operating mode, and responsive to receiving an indication of the second operating mode, obtain a second configuration profile specifying a second set of parameter values associated with the second operating mode, the second set of parameter values being different from the first set of parameter values; and control, using the second configuration profile, the ultrasound device to operate in the second operating mode.

In some embodiments, the first set of parameter values specifies a first azimuth aperture value and the second set of parameter values specifies a second azimuth aperture value different from the first azimuth aperture value, and the control circuitry is configured to control the plurality of ultrasonic transducers to operate in the first operating mode at least in part by using the first azimuth aperture value and to operate in the second operating mode at least in part by using the second azimuth aperture value.

In some embodiments, the first set of parameter values specifies a first elevation aperture value and the second set of parameter values specifies a second elevation aperture value different from the first elevation aperture value, and the control circuitry is configured to control the plurality of ultrasonic transducers to operate in the first operating mode at least in part by using the first elevation aperture value and to operate in the second operating mode at least in part by using the second elevation aperture value.

In some embodiments, the first set of parameter values specifies a first azimuth focus value and the second set of parameter values specifies a second azimuth focus value different from the first azimuth focus value, and the control circuitry is configured to control the plurality of ultrasonic transducers to operate in the first operating mode at least in part by using the first azimuth focus value and to operate in the second operating mode at least in part by using the second azimuth focus value.

In some embodiments, the first set of parameter values specifies a first elevation focus value and the second set of parameter values specifies a second elevation focus value different from the first elevation focus value, and the control circuitry is configured to control the plurality of ultrasonic transducers to operate in the first operating mode at least in part by using the first elevation focus value and to operate in the second operating mode at least in part by using the second elevation focus value.

In some embodiments, the first set of parameter values specifies a first bias voltage value for at least one of the plurality of ultrasonic transducers and the second set of parameter values specifies a second bias voltage value for the at least one of the plurality of ultrasonic transducers, the second bias voltage value being different from the first bias voltage focus value, and the control circuitry is configured to control the plurality of ultrasonic transducers to operate in the first operating mode at least in part by using the first bias voltage value and to operate in the second operating mode at least in part by using the second bias voltage value.

In some embodiments, the first set of parameter values specifies a first transmit peak-to-peak voltage value and the second set of parameter values specifies a second transmit peak-to-peak voltage value different from the first transmit peak-to-peak voltage focus value, and the control circuitry is configured to control the plurality of ultrasonic transducers to operate in the first operating mode at least in part by using the first transmit peak-to-peak voltage value and to operate in the second operating mode at least in part by using the second transmit peak-to-peak voltage value.

In some embodiments, the first set of parameter values specifies a first transmit center frequency value and the second set of parameter values specifies a second transmit center frequency value different from the first transmit center frequency value, and the control circuitry is configured to control the plurality of ultrasonic transducers to operate in the first operating mode at least in part by using the first transmit center frequency value and to operate in the second operating mode at least in part by using the second transmit center frequency value.

In some such embodiments, a difference between the first and second center frequency values is at least 1 MHz.

In some such embodiments, the difference is at least 2 MHz.

In some such embodiments, the difference is between 5 MHz and 10 MHz.

In some such embodiments, the first center frequency value is within 1-5 MHz and the second center frequency value is within 5-9 MHz.

In some such embodiments, the first center frequency value is within 2-4 MHz and the second center frequency value is within 6-8 MHz.

In some such embodiments, the first center frequency value is within 6-8 MHz and the second center frequency value is within 12-15 MHz.

In some embodiments, the first set of parameter values specifies a first receive center frequency value and the second set of parameter values specifies a second receive center frequency value different from the first receive center frequency value, and the control circuitry is configured to control the plurality of ultrasonic transducers to operate in the first operating mode at least in part by using the first receive center frequency value and to operate in the second operating mode at least in part by using the second receive center frequency value.

In some such embodiments, the first set of parameter values further specifies a first transmit center frequency value that is equal to the first receive center frequency value.

In some such embodiments, the first set of parameter values further specifies a first transmit center frequency value that is not equal to the first receive center frequency value.

In some such embodiments, the first receive center frequency value is a multiple of the first transmit frequency value.

In some such embodiments, the first receive center frequency value is approximately two times the first transmit frequency value.

In some embodiments, the first set of parameter values specifies a first polarity value and the second set of parameter values specifies a second polarity value different from the first polarity value, and the control circuitry is configured to control the plurality of ultrasonic transducers to operate in the first operating mode at least in part by using the first polarity value and to operate in the second operating mode at least in part by using the second polarity value.

In some embodiments, the ultrasound device further comprises an analog-to-digital converter (ADC), the first set of parameter values specifies a first ADC clock rate value and the second set of parameter values specifies a second ADC clock rate value different from the first ADC clock rate value, and the control circuitry is configured to control the plurality of ultrasonic transducers to operate in the first operating mode at least in part by operating the ADC at the first ADC clock rate value and to operate in the second operating mode at least in part by operating the ADC at the second ADC clock rate value.

In some embodiments, the first set of parameter values specifies a first decimation rate value and the second set of parameter values specifies a second decimation rate value different from the first decimation rate value, and the control circuitry is configured to control the plurality of ultrasonic transducers to operate in the first operating mode at least in part by using the first decimation rate value and to operate in the second operating mode at least in part by using the second decimation rate value.

In some embodiments, the first set of parameter values specifies a first receive duration value and the second set of parameter values specifies a second receive value different from the first receive duration value, and the control circuitry is configured to control the plurality of ultrasonic transducers to operate in the first operating mode at least in part by using the first receive duration value and to operate in the second operating mode at least in part by using the second receive duration value.

In some embodiments, the plurality of GUI elements comprises GUI elements representing at least two of: an operating mode for cardiac imaging, an operating mode for abdominal imaging, an operating mode for small parts imaging, an operating mode for lung imaging, an operating mode for ocular imaging, an operating mode for vascular imaging, an operating mode for 3D imaging, an operating mode for shear imaging, or an operating mode for Doppler imaging.

In some embodiments, the display is a touch screen, and the computing device is configured to receive the input indicating the selection via the touch screen.

In some embodiments, the control circuitry is configured to obtain the first configuration profile by receiving it from the computing device.

In some embodiments, the control circuitry is configured to obtain the first configuration profile by accessing it in a memory of the ultrasound device.

In some embodiments, the control circuitry is configured to operate the ultrasound device in the first operating mode and provide, to the computing device, data obtained through operation of the ultrasound device in the first operating mode.

In some such embodiments, the at least one computer hardware processor is configured to: generate an ultrasound image from the data; and display the ultrasound image via the display.

In some embodiments, the computing device comprises the display.

In some embodiments, the computing device is a mobile device.

In some embodiments, the computing device is a smartphone.

In some embodiments, the ultrasound device is a handheld ultrasound probe.

In some embodiments, wherein the ultrasound device is a wearable ultrasound device.

In some embodiments, the plurality of ultrasonic transducers includes a plurality of metal oxide semiconductor (MOS) ultrasonic transducers.

In some embodiments, the plurality of MOS ultrasonic transducers includes a first MOS ultrasonic transducer including a cavity formed in a MOS wafer, with a membrane overlying and sealing the cavity.

In some embodiments, the plurality of ultrasonic transducers includes a plurality of micromachined ultrasonic transducers.

In some embodiments, the plurality of ultrasonic transducers includes a plurality of capacitive micromachined ultrasonic transducers.

In some embodiments, the plurality of ultrasonic transducers includes a plurality of piezoelectric ultrasonic transducers.

In some embodiments, the plurality of ultrasonic transducers comprises between 5000 and 15000 ultrasonic transducers arranged in a two-dimensional arrangement.

According to some aspects of the present application a method is provided, comprising: receiving, via a graphical user interface, a selection of an operating mode for an ultrasound device configured to operate in a plurality of modes including a first operating mode and a second operating mode; responsive to receiving a selection of a first operating mode, obtaining a first configuration profile specifying a first set of parameter values associated with the first operating mode; and controlling, using the first configuration profile, the ultrasound device to operate in the first operating mode, and responsive to receiving a selection of the second operating mode, obtaining a second configuration profile specifying a second set of parameter values associated with the second operating mode, the second set of parameter values being different from the first set of parameter values; and controlling, using the second configuration profile, the ultrasound device to operate in the second operating mode.

According to some aspects of the present application a handheld multi-modal ultrasound probe is provided, configured to operate in a plurality of operating modes associated with a respective plurality of configuration profiles, the handheld ultrasound probe comprising: a plurality of ultrasonic transducers; and control circuitry configured to: receive an indication of a selected operating mode; access a configuration profile associated with the selected operating mode; and control, using parameter values specified in the accessed configuration profile, the handheld multi-modal ultrasound probe to operate in the selected operating mode.

According to some aspects of the present application an ultrasound device is provided, capable of operating in a plurality of operating modes including a first operating mode and a second operating mode, the ultrasound device comprising: a plurality of ultrasonic transducers, and control circuitry configured to: receive an indication of a selected operating mode; responsive to determining that the selecting operating mode is the first operating mode, obtain a first configuration profile specifying a first set of parameter values associated with the first operating mode; and control, using the first configuration profile, the ultrasound device to operate in the first operating mode, and responsive to receiving an indication of the second operating mode, responsive to determining that the selecting operating mode is the second operating mode, obtain a second configuration profile specifying a second set of parameter values associated with the second operating mode, the second set of parameter values being different from the first set of parameter values; and control, using the second configuration profile, the ultrasound device to operate in the second operating mode.

In some embodiments, the ultrasound device comprises a mechanical control mechanism for selecting an operating mode among the plurality of operating modes.

In some embodiments, the ultrasound device comprises a display and the ultrasound device is configured to generate a graphical user interface (GUI) for selecting an operating mode among the plurality of modes and present the generated GUI through the display.

In some embodiments, the first set of parameter values specifies a first azimuth aperture value and the second set of parameter values specifies a second azimuth aperture value different from the first azimuth aperture value, and the control circuitry is configured to control the plurality of ultrasonic transducers to operate in the first operating mode at least in part by using the first azimuth aperture value and to operate in the second operating mode at least in part by using the second azimuth aperture value.

In some embodiments, the first set of parameter values specifies a first elevation aperture value and the second set of parameter values specifies a second elevation aperture value different from the first elevation aperture value, and the control circuitry is configured to control the plurality of ultrasonic transducers to operate in the first operating mode at least in part by using the first elevation aperture value and to operate in the second operating mode at least in part by using the second elevation aperture value.

In some embodiments, the first set of parameter values specifies a first azimuth focus value and the second set of parameter values specifies a second azimuth focus value different from the first azimuth focus value, and the control circuitry is configured to control the plurality of ultrasonic transducers to operate in the first operating mode at least in part by using the first azimuth focus value and to operate in the second operating mode at least in part by using the second azimuth focus value.

In some embodiments, the first set of parameter values specifies a first elevation focus value and the second set of parameter values specifies a second elevation focus value different from the first elevation focus value, and the control circuitry is configured to control the plurality of ultrasonic transducers to operate in the first operating mode at least in part by using the first elevation focus value and to operate in the second operating mode at least in part by using the second elevation focus value.

In some embodiments, the first set of parameter values specifies a first bias voltage value for at least one of the plurality of ultrasonic transducers and the second set of parameter values specifies a second bias voltage value for the at least one of the plurality of ultrasonic transducers, the second bias voltage value being different from the first bias voltage focus value, and the control circuitry is configured to control the plurality of ultrasonic transducers to operate in the first operating mode at least in part by using the first bias voltage value and to operate in the second operating mode at least in part by using the second bias voltage value.

In some embodiments, the first set of parameter values specifies a first transmit peak-to-peak voltage value and the second set of parameter values specifies a second transmit peak-to-peak voltage value different from the first transmit peak-to-peak voltage focus value, and the control circuitry is configured to control the plurality of ultrasonic transducers to operate in the first operating mode at least in part by using the first transmit peak-to-peak voltage value and to operate in the second operating mode at least in part by using the second transmit peak-to-peak voltage value.

In some embodiments, the first set of parameter values specifies a first transmit center frequency value and the second set of parameter values specifies a second transmit center frequency value different from the first transmit center frequency value, and the control circuitry is configured to control the plurality of ultrasonic transducers to operate in the first operating mode at least in part by using the first transmit center frequency value and to operate in the second operating mode at least in part by using the second transmit center frequency value.

In some embodiments, the first set of parameter values specifies a first receive center frequency value and the second set of parameter values specifies a second receive center frequency value different from the first receive center frequency value, and the control circuitry is configured to control the plurality of ultrasonic transducers to operate in the first operating mode at least in part by using the first receive center frequency value and to operate in the second operating mode at least in part by using the second receive center frequency value.

In some embodiments, the first set of parameter values specifies a first polarity value and the second set of parameter values specifies a second polarity value different from the first polarity value, and the control circuitry is configured to control the plurality of ultrasonic transducers to operate in the first operating mode at least in part by using the first polarity value and to operate in the second operating mode at least in part by using the second polarity value.

In some embodiments, the ultrasound device comprises an analog-to-digital converter (ADC), the first set of parameter values specifies a first ADC clock rate value and the second set of parameter values specifies a second ADC clock rate value different from the first ADC clock rate value, and the control circuitry is configured to control the plurality of ultrasonic transducers to operate in the first operating mode at least in part by operating the ADC at the first ADC clock rate value and to operate in the second operating mode at least in part by operating the ADC at the second ADC clock rate value.

In some embodiments, the first set of parameter values specifies a first decimation rate value and the second set of parameter values specifies a second decimation rate value different from the first decimation rate value, and the control circuitry is configure to control the plurality of ultrasonic transducers to operate in the first operating mode at least in part by using the first decimation rate value and to operate in the second operating mode at least in part by using the second decimation rate value.

In some embodiments, the first set of parameter values specifies a first receive duration value and the second set of parameter values specifies a second receive value different from the first receive duration value, and the control circuitry is configured to control the plurality of ultrasonic transducers to operate in the first operating mode at least in part by using the first receive duration value and to operate in the second operating mode at least in part by using the second receive duration value.

In some embodiments, the plurality of operating modes comprises an operating mode for cardiac imaging, an operating mode for abdominal imaging, an operating mode for small parts imaging, an operating mode for lung imaging, and an operating model for ocular imaging.

In some embodiments, the ultrasound device is a handheld ultrasound probe.

In some embodiments, the ultrasound device is a wearable ultrasound device.

In some embodiments, the plurality of ultrasonic transducers includes a plurality metal oxide semiconductor (MOS) ultrasonic transducers.

In some embodiments, the plurality of ultrasonic transducers includes a plurality of capacitive micromachined ultrasonic transducers.

According to some aspects of the present application a mobile computing device is provided, communicatively coupled to an ultrasound device, the mobile computing device comprising: at least one computer hardware processor; a display; and at least one non-transitory computer-readable storage medium storing an application program that, when executed by the at least one computer hardware processor causes the at least one computer hardware processor to: generate a graphical user interface (GUI) having a plurality of GUI elements representing a respective plurality of operating modes for the multi-modal ultrasound device; present the GUI via the display; receive, via the GUI, user input indicating selection of one of the plurality of operating modes; and provide an indication of the selected operating mode to the ultrasound device.

In some embodiments, the plurality of GUI elements comprises a GUI element representing an operating mode for cardiac imaging, an operating mode for abdominal imaging, an operating mode for small parts imaging, an operating mode for lung imaging, and an operating model for ocular imaging.

In some embodiments, the display is a touchscreen, and the mobile computing device is configured to receive the user input indicating the selection via the touchscreen.

In some embodiments, the at least one computer hardware processor is further configured to: receive data obtained by the ultrasound device during operation in the selected operating mode; generate at least one ultrasound image from the data; and display the at least one generated ultrasound image via the display.

What is claimed is:

1. A system, comprising:
   a multi-modal ultrasound probe having a substantially flat transducer array; and
   a computing device coupled to the multi-modal ultrasound probe; wherein:
   the computing device is configured, in response to receiving input indicating an operating mode selected by a user, to provide an indication of the operating mode selected by the user to the multi-modal ultrasound probe; and
   the multi-modal ultrasound probe having the substantially flat transducer array comprises control circuitry configured to:
   responsive to receiving an indication from the computing device of a first operating mode:
      obtain a first configuration profile specifying a first set of parameter values, wherein the first set of parameter values comprises a first azimuth aperture value and a first elevation aperture value; and
      control the substantially flat ultrasound transducer array to use a first aperture based on the first configuration profile to generate a first accumulation of azimuthal intensities comprising a linear beam shape;
   responsive to receiving an indication from the computing device of a second operating mode;
      obtain a second configuration profile specifying a second set of parameter values different from the first set of parameter values, wherein the second set of parameter values comprises a second azimuth aperture value and a second elevation aperture value; and
      control the substantially flat ultrasound transducer array to use a second aperture based on the second configuration profile to generate a second accumulation of azimuthal intensities comprising a sector beam shape; and
   responsive to receiving an indication from the computing device of a third operating mode;
      obtain a third configuration profile specifying a third set of parameter values different from the first and second sets of parameter values, wherein the third set of parameter values comprises a third azimuth aperture value and a third elevation aperture value; and
      control the substantially flat ultrasound transducer array to use a third aperture based on the third configuration profile to generate a third accumulation of azimuthal intensities comprising a convex beam shape.

2. The system of claim 1, wherein the first set of parameter values specifies a first azimuth focus value and the second set of parameter values specifies a second azimuth focus value different from the first azimuth focus value.

3. The system of claim 1, wherein the first set of parameter values specifies a first bias voltage value for at least one ultrasonic transducer of the substantially flat ultrasound transducer array and the second set of parameter values specifies a second bias voltage value for the at least one ultrasonic transducer, the second bias voltage value being different from the first bias voltage value.

4. The system of claim 1, wherein the first set of parameter values specifies a first transmit peak-to-peak voltage value and the second set of parameter values specifies a second transmit peak-to-peak voltage value different from the first transmit peak-to-peak voltage value.

5. The system of claim 1, wherein the first set of parameter values specifies a first transmit center frequency value and the second set of parameter values specifies a second transmit center frequency value different from the first transmit center frequency value.

6. The system of claim 1, wherein the first set of parameter values specifies a first receive center frequency value and the second set of parameter values specifies a second receive center frequency value different from the first receive center frequency value.

7. The system of claim 1,
wherein the first set of parameter values specifies a first polarity value and the second set of parameter values specifies a second polarity value different from the first polarity value.

8. The system of claim 1,
wherein the multi-modal ultrasound probe further comprises an analog-to-digital converter (ADC),
wherein the first set of parameter values specifies a first ADC clock rate value and the second set of parameter values specifies a second ADC clock rate value different from the first ADC clock rate value.

9. The system of claim 1,
wherein the first set of parameter values specifies a first decimation rate value and the second set of parameter values specifies a second decimation rate value different from the first decimation rate value.

10. The system of claim 1,
wherein the first set of parameter values specifies a first receive duration value and the second set of parameter values specifies a second receive duration value different from the first receive duration value.

11. The system of claim 1, wherein the multi-modal ultrasound probe is a hand-held ultrasound probe.

12. The system of claim 1, wherein the control circuitry is configured to control the substantially flat ultrasound transducer array to operate at a first frequency, and at least some ultrasonic transducers of the substantially flat transducer array have pitch less than or equal to lambda and greater than or equal to lambda/4 for the first frequency, and wherein lambda is a wavelength at the first frequency.

13. The system of claim 12, wherein the substantially flat transducer array has a fixed pitch of ultrasonic transducers.

14. The system of claim 1, wherein:
the first frequency is between about 1 MHz and about 5 MHz.

15. The system of claim 1, wherein the multi-modal ultrasound probe is configured to image a first depth between 10 cm and 25 cm.

16. The system of claim 1, wherein at least some ultrasonic transducers of the substantially flat transducer array have a pitch less than or equal to 500 μm and greater than or equal to 125 μm.

17. A method for controlling operation of a multi-modal ultrasound probe having a substantially flat transducer array, the method comprising:
receiving, at a computing device, input indicating an operating mode selected by a user;
providing, by the computing device in response to receiving the input indicating the operating mode selected by the user, an indication of the operating mode selected by the user to the multi-modal ultrasound probe;
responsive to receiving, by control circuitry in the multi-modal ultrasound probe, an indication from the computing device of a first operating mode;
obtaining, by the control circuitry, a first configuration profile specifying a first set of parameter values, wherein the first set of parameter values comprises a first azimuth aperture value and a first elevation aperture value; and
controlling, by the control circuitry, the substantially flat ultrasound transducer array to use a first aperture based on the first configuration profile to generate a first accumulation of azimuthal intensities comprising a linear beam shape;
responsive to receiving, by the control circuitry, an indication from the computing device of a second operating mode;
obtaining, by the control circuitry, a second configuration profile specifying a second set of parameter values different from the first set of parameter values, wherein the second set of parameter values comprises a second azimuth aperture value and a second elevation aperture value; and
controlling, by the control circuitry, the substantially flat ultrasound transducer array to use a second aperture based on the second configuration profile to generate a second accumulation of azimuthal intensities comprising a sector beam shape; and
responsive to receiving, by the control circuitry, an indication from the computing device of a third operating mode;
obtaining, by the control circuitry, a third configuration profile specifying a third set of parameter values different from the first and second sets of parameter values, wherein the third set of parameter values comprises a third azimuth aperture value and a third elevation aperture value; and
controlling, by the control circuitry, the substantially flat ultrasound transducer array to use a third aperture based on the third configuration profile to generate a third accumulation of azimuthal intensities comprising a convex beam shape.

* * * * *